US012612614B2

(12) United States Patent
Horlitz et al.

(10) Patent No.: US 12,612,614 B2
(45) Date of Patent: Apr. 28, 2026

(54) STABILIZATION OF RNA

(71) Applicant: QIAGEN GmbH, Hilden (DE)

(72) Inventors: Martin Horlitz, Hilden (DE); Uwe Oelmüller, Hilden (DE)

(73) Assignee: QIAGEN GMbH, Hilden (DE)

( * ) Notice: Subject to any disclaimer, the term of this patent is extended or adjusted under 35 U.S.C. 154(b) by 289 days.

(21) Appl. No.: 16/086,097

(22) PCT Filed: Mar. 16, 2017

(86) PCT No.: PCT/EP2017/056273
§ 371 (c)(1),
(2) Date: Sep. 18, 2018

(87) PCT Pub. No.: WO2017/162518
PCT Pub. Date: Sep. 28, 2017

(65) Prior Publication Data
US 2020/0291385 A1     Sep. 17, 2020

(30) Foreign Application Priority Data

Mar. 19, 2016   (EP) ..................................... 16161294
Mar. 19, 2016   (EP) ..................................... 16161295
May 25, 2016   (EP) ..................................... 16171321

(51) Int. Cl.
*C12Q 1/6806*     (2018.01)
*C12N 15/10*     (2006.01)

(52) U.S. Cl.
CPC ....... *C12N 15/1003* (2013.01); *C12Q 1/6806* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 6,204,375 B1 | 3/2001 | Lader | |
| 6,872,818 B2 | 3/2005 | Korfhage et al. | |
| 7,683,035 B1 | 3/2010 | Erbacher et al. | |
| 2008/0038782 A1* | 2/2008 | Borns .................... | C12Q 1/686 |
| | | | 536/23.1 |
| 2008/0187924 A1* | 8/2008 | Korfhage ............. | C12Q 1/6806 |
| | | | 435/6.1 |
| 2009/0081802 A1* | 3/2009 | Ritt ...................... | C12N 15/101 |
| | | | 436/94 |

FOREIGN PATENT DOCUMENTS

| | | |
|---|---|---|
| CN | 104032030 A | 9/2014 |
| EP | 1031626 B1 | 8/2000 |
| WO | 99/29703 A2 | 6/1999 |
| WO | 00/06780 A1 | 2/2000 |
| WO | 02/059360 A2 | 8/2002 |
| WO | 2007/065950 A1 | 6/2007 |
| WO | 2010/072821 A1 | 7/2010 |
| WO | 2010/072834 A1 | 7/2010 |
| WO | 2011/008553 A1 | 1/2011 |
| WO | 2014/066376 A1 | 5/2014 |
| WO | 2014/144767 A1 | 9/2014 |
| WO | 2016/198571 A1 | 12/2016 |

OTHER PUBLICATIONS

Wan, Genome-wide Measurement of RNA Folding Energies, Molecular Cell, 48: 169-181, 2012. (Year: 2012).*
Media Lab, LabCE—Reverse Transcriptase Polymerase Chain Reaction, 2001. (Year: 2001).*
Roche, Tth DNA Polymerase from Thermus thermophilus recombinant (E. coli), 2020. (Year: 2020).*
Oh et al., "Development of an Ammonium Sulfate DNA Extraction Method for Obtaining Amplifiable DNA in a Small Number of Cells and Its Application to Clinical Specimens," BioMed Research International, vol. 2013 (10 Pages) (2013).
Zlobina et al., "Efficient large-scale preparation and purification of short single-stranded RNA oligonucleotides," BioTechniques 60:75-83 (Feb. 2016).
Elliott et al., Molecular Biology of RNA, Oxford University Press, Oxford, United Kingdom, 2011, pp. 34-39. (3 pages).
Fabre et al., "An efficient method for long-term room temperature storage of RNA," European Journal of Human Genetics 22:379-385, 2014.
Fleige et al., "RNA integrity and the effect on the real-time qRT-PCR performance," Molecular Aspects of Medicine 27:126-139, 2006.
Bock, "[29] Alkaline Hydrolysis of RNA," in Grossman et al. (eds.), Methods in Enzymology vol. XII: Nucleic Acids Part A, Academic Press, New York, New York, USA, 1967, pp. 224-228. (7 pages).
Salehi et al., "RNA Preservation and Stabilization," Biochem Physiol 3(1):1000126, 2014. (4 pages).
Schroeder et al., "The RIN: an RNA integrity number for assigning integrity values to RNA measurements," BMC Molecular Biology 7:3, 2006. (14 pages).

* cited by examiner

*Primary Examiner* — Gary Benzion
*Assistant Examiner* — Carolyn L Greene
(74) *Attorney, Agent, or Firm* — Seed Intellectual Property Law Group LLP

(57) ABSTRACT

The present invention pertains to methods, uses, compositions and kits for treating RNA at conditions comprising a temperature of at least 70° C. and a pH of at least 8, preferably a pH of at least 9. It also pertains to methods, uses and compositions for stabilizing RNA at conditions comprising a temperature of at least 70° C. and a pH of at least 8, preferably a pH of at least 9. It based on the finding that RNA can be stabilized in the presence of ammonium sulfate. In particular, the present invention provides a method of processing RNA, comprising treating the RNA at conditions comprising a temperature of at least 70° C. and a pH of at least 8, preferably a pH of at least 9, in the presence of ammonium sulfate at a concentration of 10 mM or less.

18 Claims, 47 Drawing Sheets
Specification includes a Sequence Listing.

Buffer 1 | Full-length 18S rRNA vs. incubation time $y = 100e^{-0,536x}$

◆ Buffer 1 | 18S rRNA     ━━Expon. (Buffer 1 | 18S rRNA)

Buffer 2 | Full-length 18S rRNA vs. incubation time $y = 100e^{-0,282x}$

◆ Buffer 2 | 18S rRNA     ━━Expon. (Buffer 2 | 18S rRNA)

Buffer 3 | Full-length 18S rRNA vs. incubation time

$y = 100e^{-0,054x}$

■ Buffer 3 | 18S rRNA          ——Expon. (Buffer 3 | 18S rRNA)

Buffer 4 | Full-length 18S rRNA vs. incubation time

$y = 100e^{-0,004x}$

▲ Buffer 4 | 18S rRNA          ——Expon. (Buffer 4 | 18S rRNA)

Buffer 1 | Full-length 28S rRNA vs. incubation time

$y = 100e^{-0,641x}$

◆ Buffer 1 | 28S rRNA     ▬Expon. (Buffer 1 | 28S rRNA)

Buffer 2 | Full-length 28S rRNA vs. incubation time

$y = 100e^{-0,446x}$

◆ Buffer 2 | 28S rRNA     ▬Expon. (Buffer 2 | 28S rRNA)

Buffer 1 | Full-length 18S rRNA vs. incubation time

$$y = 144{,}71e^{-0{,}13x}$$

◆  Buffer 1 | 18S     ──Expon. (Buffer 1 | 18S)

Buffer 2 | Full-length 18S rRNA vs. incubation time

$$y = 101{,}35e^{-0{,}08x}$$

■  Buffer 2 | 18S     ──Expon. (Buffer 2 | 18S)

Buffer 3 | Full-length 18S rRNA vs. incubation time $y = 97{,}766e^{0{,}0044x}$

Buffer 1 | Full-length 28S rRNA vs. incubation time

$$y = 111{,}64e^{-0{,}234x}$$

◆ Buffer 1 | 28S   —— Expon. (Buffer 1 | 28S)

Buffer 2 | Full-length 28S rRNA vs. incubation time

$$y = 82{,}123e^{-0{,}168x}$$

■ Buffer 2 | 28S   —— Expon. (Buffer 2 | 28S)

Buffer 3 | Full-length 28S rRNA vs. incubation time

$y = 99{,}886e^{-0{,}03x}$ rel. amount of RNA time[min]

● Buffer 3 | 28S ——Expon. (Buffer 3 | 28S)

STABILIZATION OF RNA

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_483USPC_SEQUENCE_LISTING.txt. The text file is 1,600 bytes, was created on Sep. 10, 2018, and is being submitted electronically via EFS-Web.

The present invention pertains to methods, uses and compositions for processing RNA at conditions comprising a temperature of at least 70° C. and a pH of at least 8, preferably a pH of at least 9. In particular, it pertains to methods, uses and compositions for stabilizing RNA at conditions comprising a temperature of at least 70° C. and a pH of at least 8, preferably a pH of at least 9.

BACKGROUND OF THE INVENTION

For many molecular biology and diagnostic applications, it is desirable to isolate or purify ribonucleic acid (RNA) of good quality and with high yield. However, RNA is quite unstable and prone to degradation prior to and during RNA isolation or purification. Factors contributing to the degradation of RNA include degrading enzymes such as RNAses but also processing conditions including elevated temperature and high pH value. This instability poses a problem also for other methods that involve the processing of RNA.

Methods and reagents for preserving and protecting RNA in tissue samples prior to RNA isolation are known and have for example been described in U.S. Pat. No. 6,204,375 B1. Also, methods to mitigate the inhibitory or destroying effects of molecules binding to or cleaving RNA present in RNA containing samples or mixtures are known and have for example been described in U.S. Pat. No. 6,872,818 B2.

RNA is known to be subject to spontaneous hydrolysis under alkaline conditions. RNA hydrolysis under alkaline conditions ultimately leads to complete, sequence-independent degradation of RNA molecules to mononucleotides. This hydrolysis reaction is driven by deprotonation of the 2'—OH group of the ribose moiety under elevated concentrations of OH$^{(-)}$ ions in aqueous solutions. The phenomenon has been described previously (see e.g. Bock, R. M.: Alkaline hydrolysis of RNA, Methods in Enzymology, Volume 12, Part A, 1967, pages 224-228; Elliot, D., Ladomery, M.: Molecular Biology of RNA (1st ed. 2011). New York: Oxford University Press, pages 34-64).

Processing RNA at strongly alkaline conditions is, however, desirable for a number of applications. One example is the isolation of RNA from a sample using an anion exchange matrix. An alkaline pH of at least 8 may be used to release, in particular elute, bound RNA from an anion exchange matrix. An alkaline pH of at least 9 is usually needed to efficiently release, in particular elute, the bound RNA from the anion exchange matrix. This can lead to degradation of the RNA during the elution step. RNA isolation methods wherein the RNA is eluted from an anion exchange matrix using alkaline solutions are described in WO 2007/065950 and WO 2014/066376.

As is also demonstrated in the present examples, alkaline degradation of RNA is considerably accelerated at high temperatures. Therefore, the problem of RNA hydrolysis in alkaline aqueous solutions is particularly pronounced at high temperatures (such as e.g. temperatures of at least 70° C., at least 75° C., at least 80° C. or higher). Under these conditions, RNA is rapidly degraded. RNA becomes hydrolyzed to single nucleotides by de-protonation of the 2'-hydroxy group on the ribose moiety, followed by a reaction of the resulting —O$^{(-)}$ with the phosphorous of the 3' bound phosphate group which then leads to breakage of the phosphodiester bond. This susceptibility of RNA to degradation makes it difficult to ensure RNA integrity at conditions that involve a high temperature and an alkaline pH of in particular 9 or higher.

Therefore, there is a need for improved methods and compositions that protect the RNA from degradation during processing at conditions that involve a high temperature and a strongly alkaline pH. Ideally, such methods and compositions should not interfere with downstream applications such as e.g. downstream applications for the analysis or detection of RNA.

It is an object of the present invention to provide means to protect RNA from degradation during processing at high temperature and alkaline conditions. It is in particular an object of the present invention to provide a method for stabilizing RNA at high temperature and strongly alkaline conditions, in particular during release from an anion exchange matrix. Furthermore, it is an object to provide improved methods and compositions for isolating RNA using an anion exchange matrix, in particular for protecting the RNA from degradation during alkaline elution from the anion exchange matrix. Furthermore, it is an object to provide solutions, uses and compositions for the processing or stabilization of RNA at high temperature and strongly alkaline conditions.

SUMMARY OF THE INVENTION

The inventors found that unexpectedly, RNA is effectively stabilized during treatment conditions at high temperatures (≥70° C.) and high pH (≥8, preferably ≥9) in the presence of ammonium sulfate. Advantageously, RNA degradation is significantly inhibited in the presence of ammonium sulfate. Surprisingly, very low concentrations of ammonium sulfate of ≤10 mM, ≤5 mM and even ≤3.5 mM are sufficient and highly effective to achieve a pronounced stabilization effect. The presence of ammonium sulfate at these low concentrations advantageously protects the RNA from degradation even when the RNA is incubated for prolonged periods at high temperatures and at high pH as is demonstrated by the examples. These advantageous effects of ammonium sulfate can be used in order to protect the RNA during release, in particular elution, from an anion exchange matrix under conditions involving a temperature of at least 70° C. and a pH of at least 8, preferably a pH of at least 9. The present invention thus allows to use such harsh conditions when processing RNA. The obtained RNA is due to its quality suitable for highly sensitive and quantitative analysis and detection methods, such as e.g. PCR-based analysis and detection. Furthermore, low concentrations of ammonium sulfate as can be used according to the present invention do not interfere with such downstream applications and the obtained RNA can be used without further purification to remove excess salt. Thus, the present invention provides methods of processing RNA which comprise treating the RNA at high temperature and strongly alkaline conditions that are compatible with sensitive downstream applications of the RNA, such as the use of the RNA in diagnostics assays, e.g. for the detection of viral RNA. Therefore, the present invention offers important advantages and provides a notable progress over the prior art.

The term "ammonium sulfate" as used herein refers to diammonium sulfate ((NH$_4$)$_2$SO$_4$) as well as to ammonium bisulfate (NH$_4$HSO$_4$; also referred to as ammonium hydrogen sulfate). Thus, any disclosure presented herein for "ammonium sulfate" in general specifically applies and refers to the embodiment diammonium sulfate as well as to the embodiment ammonium bisulfate. Particularly preferred is the use of diammonium sulfate ((NH$_4$)$_2$SO$_4$) as ammonium sulfate. Thus, all disclosures described in this application for ammonium sulfate in general, specifically apply and particularly refer to the preferred embodiment diammonium sulfate ((NH$_4$)$_2$SO$_4$) even if not explicitly stated.

According to a first aspect, the present invention provides a method of processing RNA, comprising treating the RNA at conditions comprising a temperature of at least 70° C. and a pH of at least 8 in the presence of ammonium sulfate, preferably at a concentration of 10 mM or less. The present invention in particular provides a method of processing RNA, comprising treating the RNA at conditions comprising a temperature of at least 70° C. and a pH of at least 9 in the presence of ammonium sulfate, preferably at a concentration of 10 mM or less.

Also provided is a method of releasing RNA from an anion exchange matrix to which the RNA is bound, said method comprising treating the RNA at conditions comprising a temperature of at least 70° C. and a pH of at least 8 in the presence of ammonium sulfate at a concentration of 10 mM or less to release the RNA from the anion exchange matrix. The present invention in particular provides a method of releasing RNA from an anion exchange matrix to which the RNA is bound, said method comprising treating the RNA at conditions comprising a temperature of at least 70° C. and a pH of at least 9 in the presence of ammonium sulfate at a concentration of 10 mM or less to release the RNA from the anion exchange matrix.

Also provided is a method of isolating RNA from a sample, said method comprising binding the RNA to an anion exchange matrix;
treating the RNA at conditions comprising a temperature of at least 70° C. and a pH of at least 8 in the presence of ammonium sulfate, preferably at a concentration of 10 mM or less to release the RNA from the anion exchange matrix.

In particular, the present invention provides a method of isolating RNA from a sample, said method comprising binding the RNA to an anion exchange matrix;
treating the RNA at conditions comprising a temperature of at least 70° C. and a pH of at least 9 in the presence of ammonium sulfate, preferably at a concentration of 10 mM or less to release the RNA from the anion exchange matrix.

According to a further aspect, the invention provides for the use of ammonium sulfate at a concentration of 10 mM or less for stabilizing RNA at conditions comprising a temperature of at least 70° C. and a pH of at least 8. The invention in particular provides for the use of ammonium sulfate at a concentration of 10 mM or less for stabilizing RNA at conditions comprising a temperature of at least 70° C. and a pH of at least 9.

According to a further aspect, the invention provides for the use of a solution for releasing RNA from an anion exchange matrix, the solution having a temperature of at least 70° C. and a pH of at least 8 and the solution comprising ammonium sulfate, preferably at a concentration of 10 mM or less. The invention in particular provides for the use of a solution for releasing RNA from an anion exchange matrix, the solution having a temperature of at least 70° C. and a pH of at least 9 and the solution comprising ammonium sulfate, preferably at a concentration of 10 mM or less.

According to a further aspect, the invention provides for an RNA containing composition, the composition comprising ammonium sulfate at a concentration of 10 mM or less, the composition having a temperature of at least 70° C. and a pH of at least 8. The invention in particular provides for an RNA containing composition, the composition comprising ammonium sulfate at a concentration of 10 mM or less, the composition having a temperature of at least 70° C. and a pH of at least 9.

Other aspects, objects, features, and advantages of the present application will become apparent to those skilled in the art from the following description and appended claims. It should be understood, however, that the following description, appended claims, and specific examples, while indicating preferred embodiments of the application, are given by way of illustration only.

BRIEF DESCRIPTION OF THE FIGURES

FIG. 7A shows the RNA integrity versus time for RNA incubated at 75° C. for up to 10 min at pH 10, 11 or 12. Values for samples incubated for 10 min at 75° C. followed by incubation at room temperature are also shown. FIG. 7B shows the RNA integrity versus time for the first 10 minutes of RNA incubation at 75° C. at pH 10, 11 or 12. FIG. 7C shows the RNA integrity versus time for RNA incubated at 85° C. for up to 10 min at pH 10, 11 or 12. Values for samples incubated for 10 min at 85° C. followed by incubation at room temperature are also shown. FIG. 7D shows the RNA integrity versus time for the first 10 minutes of RNA incubation at 85° C. at pH 10, 11 or 12.

FIG. 12A shows the RNA integrity versus time for RNA incubated at 75° C. for up to 10 min at pH 10, 11 or 12, and for RNA incubated at 75° C. for up to 10 min at pH 11 in the presence of 2.5 mM ammonium sulfate. FIG. 12 B shows the RNA integrity versus time for RNA incubated at 85° C. for up to 10 min at pH 10, 11 or 12, and for RNA incubated at 85° C. for up to 10 min at pH 11 in the presence of 2.5 mM ammonium sulfate.

FIG. 13A is a gel-like image of RNA incubated with 20 mM NaOH, buffered to pH 11 (Buffer 1 of Example 4); FIG. 13B is a gel-like image of RNA incubated with 20 mM NaOH, buffered to pH 11, plus 0.01 mM (10 μM) EDTA (Buffer 2 of Example 4); FIG. 13C is a gel-like image of RNA incubated with 20 mM NaOH buffered to pH 11, plus 0.01 mM (10 μM) EDTA, plus 1 mM $(NH_4)_2SO_4$ (Buffer 3 of Example 4); FIG. 13D is a gel-like image of RNA incubated with 20 mM NaOH buffered to pH 11, plus 0.01 mM (10 μM) EDTA, plus 2.5 mM $(NH_4)_2SO_4$ (Buffer 4 of Example 4).

FIG. 18A is a gel-like image of RNA incubated with 20 mM NaOH, buffered to pH 10 (Buffer 1 of Example 5); FIG. 18B is a gel-like image of RNA incubated with 20 mM NaOH, buffered to pH 10, plus 2.5 mM $(NH_4)_2SO_4$ (Buffer 2 of Example 5); FIG. 18C is a gel-like image of RNA incubated with 20 mM NaOH buffered to pH 10, plus 2.5 mM $(NH_4)_2SO_4$, plus 1 mM EDTA, (Buffer 3 of Example 5).

DETAILED DESCRIPTION OF THE INVENTION

Figure 1A:
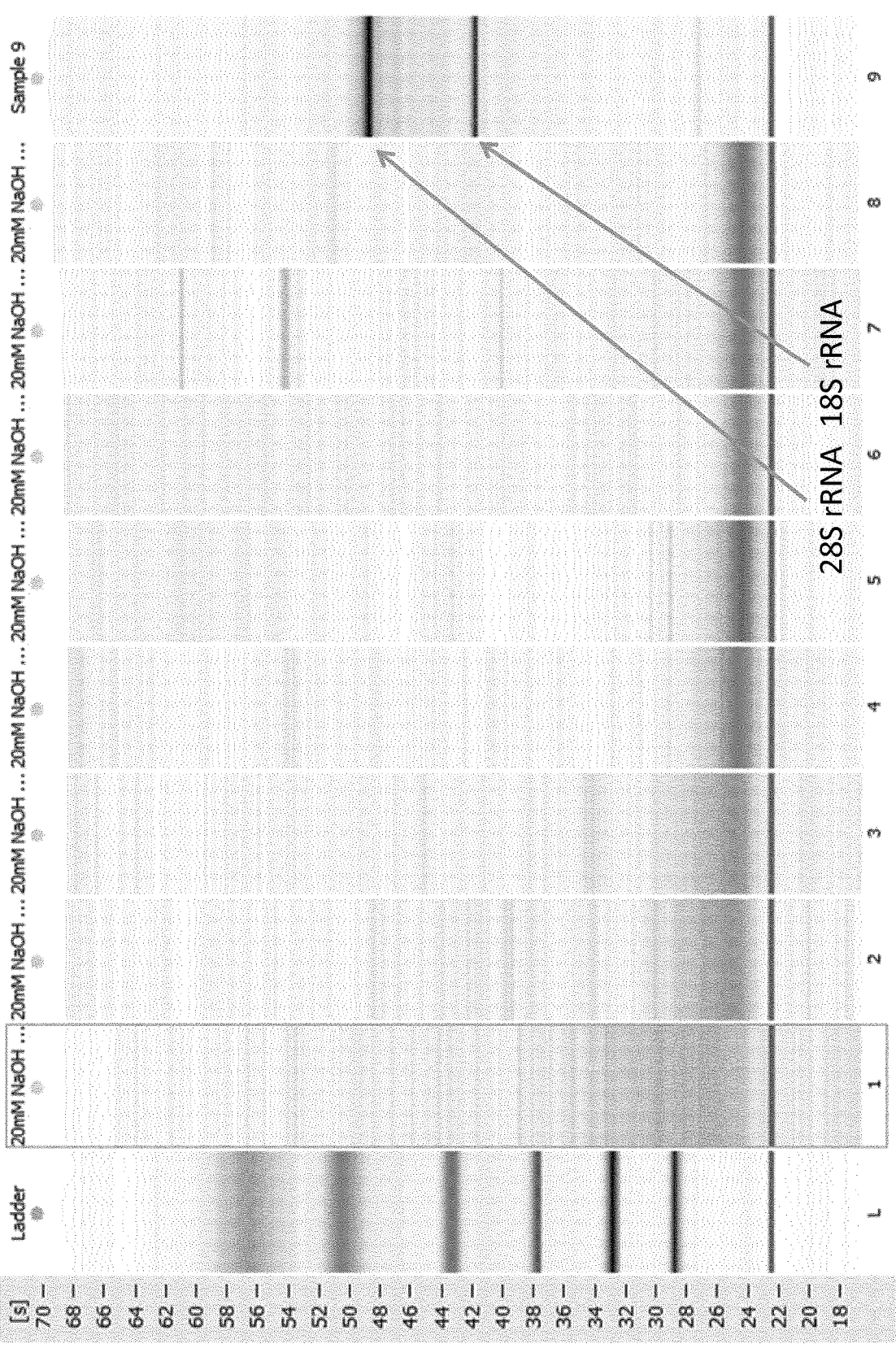
FIGS. 1A and 1B show Agilent BioAnalyzer images (gel-like image and electropherogram) of human total RNA incubated at 75° C. with solution 1, comprising 20 mM NaOH, ca. pH 12.

The present invention pertains inter alia to methods, uses and compositions that allow the processing of RNA at conditions comprising a temperature of at least 70° C. and a pH of at least 8, preferably a pH of at least 9. It in particular pertains to methods, uses and compositions for stabilizing RNA at conditions comprising a temperature of at least 70° C. and a pH of at least 8, preferably a pH of at least 9. It is based on the finding that ammonium sulfate protects even in very low concentrations the RNA from degradation at treatment conditions that involve a temperature of at least 70° C. and a pH of at least 8, preferably a pH of at least 9. The different aspects and non-limiting embodiments are described in the following.

As has been explained above, term "ammonium sulfate" as used herein refers to diammonium sulfate $((NH_4)_2SO_4)$ as well as to ammonium bisulfate $(NH_4HSO_4)$. As has likewise been explained above, all disclosures described in this application for ammonium sulfate in general, specifically apply and particularly refer to the preferred embodiment diammonium sulfate $((NH_4)_2SO_4)$ even if not explicitly stated.

Method of Processing RNA at High Temperature and High pH According to a first aspect, the present invention provides a method of processing RNA, said method comprising a step of treating the RNA at conditions comprising a temperature of at least 70° C. and a pH of at least 8, preferably a pH of at least 9, in the presence of ammonium sulfate, preferably at a concentration of 10 mM or less. The presence of ammonium sulfate surprisingly and advantageously ensures that the RNA is efficiently stabilized and thus protected against degradation at harsh temperature and pH conditions. More surprisingly, ammonium sulfate exerts a respective RNA stabilizing effect at a very low concentration of e.g. 10 mM or less as is demonstrated by the examples. Ammonium sulfate can stabilize the RNA at the temperature and pH used by inhibiting or preventing RNA degradation. Thereby, an RNA integrity can be maintained that allows for the subsequent analysis of the RNA using standard methods such as e.g. RT-PCR. As is demonstrated by the examples, the RNA integrity is considerably improved if the RNA is treated at high temperature and high pH conditions in the presence of ammonium sulfate.

The method may comprise contacting the RNA with the ammonium sulfate to establish the desired ammonium sulfate concentration such as 10 mM or less. The method of processing RNA may comprise stabilizing the RNA at treatment conditions comprising a temperature of at least 70° C. and a pH of at least 8, preferably a pH of at least 9, by contacting the RNA with ammonium sulfate, preferably at a concentration of 10 mM or less. The method may comprise stabilizing RNA at conditions involving a temperature of at least 70° C. and a pH of at least 8, preferably a pH of at least 9, the method comprising bringing the RNA into contact with ammonium sulfate, preferably at a concentration of 10 mM or less.

The ammonium sulfate can stabilize the RNA at the temperature and pH used during treatment. As used herein, "stabilizing RNA" can comprise inhibiting or preventing RNA degradation. In particular, "stabilizing RNA" can comprise inhibiting or preventing degradation of RNA molecules to mononucleotides. The RNA can in particular be protected from temperature-induced degradation or from temperature- and pH-induced degradation. "Stabilizing RNA" can in particular comprise protecting RNA from hydrolysis, more particular from spontaneous hydrolysis. "Stabilizing RNA" may comprise protecting RNA from breakage of phosphodiester bonds. The RNA integrity is substantially improved in the presence of ammonium sulfate as is demonstrated by the examples. The precise mechanism how ammonium sulfate exerts these surprising protective effects is not understood. Stabilization by ammonium sulfate could be effected via a direct or indirect interaction, e.g. by interacting directly with the RNA or by interacting with a different component that without such interaction would degrade or promote degradation of the RNA.

According to one embodiment, "stabilizing RNA" results in a reduction of RNA degradation, preferably in a reduction of RNA degradation by hydrolysis, by at least 50%, at least 60%, at least 70%, at least 80% or at least 90%. The reduction can be a reduction compared to the degradation observed for RNA treated under identical conditions but in the absence of ammonium sulfate.

According to one embodiment, "stabilizing RNA" results in an improved integrity of RNA by at least 100%, at least 150% or at least 200%. RNA integrity can be improved by 200-300% as is demonstrated by the examples. The improvement can be an improvement compared to the integrity observed for RNA treated under identical conditions but in the absence of ammonium sulfate.

Methods of determining RNA degradation and RNA integrity are well known and include the use of gel electrophoresis under denaturing conditions as well as methods based on the use of microfluidics instruments (such as the Agilent 2100 Bioanalyzer; Agilent Technologies). According to one embodiment, RNA degradation and RNA integrity can be determined by determining the RNA integrity number (RIN). The RIN is an algorithm for assigning integrity values to RNA measurements. RIN values range from 10 (intact) to 1 (totally degraded). The RIN is for example discussed in Schroeder et al. "The RIN: an RNA integrity number for assigning integrity values to RNA measurements" (BMC Molecular Biology 2006; 7:3). Typically, RNA having a RIN value of at least 5 is considered suitable for standard methods such as e.g. RT-PCR applications, including qPCR applications (see e.g. S. Fleige, M. W. Pfaffl/Molecular Aspects of Medicine 27 (2006) 126-139).

After treatment of the RNA at high temperature and high pH in the presence of ammonium sulfate as defined herein, RNA can be obtained having a RIN of at least 5, at least 6, or at least 7. As is demonstrated by the examples, this can be influenced e.g. by the temperature and pH used and the incubation time. Still higher RIN values such as at least 8 or at least 9 can be achieved, as can be seen from the examples. According to one embodiment, "stabilizing RNA" results in an RIN that is at least 100%, at least 150%, at least 200% or 200-400% higher than a RIN obtained for RNA processed under identical conditions but in the absence of ammonium sulfate.

Ammonium Sulfate

The ammonium sulfate concentration during treatment can be 50 mM or less, 40 mM or less, 30 mM or less, 25 mM or less, 20 mM or less, 15 mM or less and preferably is 10 mM or less. As mentioned above, ammonium sulfate according to the invention can be diammonium sulfate ($(NH_4)_2SO_4$) and/or ammonium bisulfate ($NH_4HSO_4$), with diammonium sulfate being preferred. Surprisingly, very low concentrations of ammonium sulfate are sufficient and efficient to achieve a stabilizing effect. According to one embodiment, the concentration of ammonium sulfate during treatment at high temperature and high pH is 9 mM or less, 8 mM or less, 7 mM or less, 6 mM or less, 5 mM or less, 4 mm or less, 3.5 mM or less or 3 mM or less. As is demonstrated by the examples, even concentrations of 2.5 mM or less are sufficient to achieve a pronounced stabilization effect. As treatment of the RNA occurs in the presence of ammonium sulfate, the concentration is above 0 mM. According to one embodiment, the concentration of ammonium sulfate is at least 0.25 mM, preferably at least 0.5 mM, at least 0.75 mM or at least 1 mM. As discussed, diammonium sulfate is preferred.

The concentration of ammonium sulfate as described herein is usually the concentration in a liquid composition that comprises the RNA during treatment. Said liquid composition has at least during treatment a pH of at least 8, preferably a pH of at least 9, and a temperature of at least 70° C. Different options to provide such a liquid composition are described herein. The concentration is in one embodiment calculated without considering the volume and/or weight of a solid phase such as an anion exchange matrix that may in embodiments be present when the RNA is treated, e.g. in order to elute the RNA from the anion exchange matrix.

According to one embodiment, the ammonium sulfate is present at a concentration of from 0.1 mM to 10 mM, from 0.25 mM to 10 mM, from 0.5 mM to 9 mM, from 0.7 mM to 8 mM, from 1 mM to 7 mM, from 1.5 mM to 6 mM, from 1.75 mM to 5 mM or from 2 mM to 4 mM when treating the RNA at conditions comprising a temperature of at least 70° C. and a pH of at least 8, preferably a pH of at least 9. Even after prolonged incubation at such high temperature and strongly alkaline conditions, a strong stabilization of the RNA was observed as is demonstrated in the examples. An exemplary concentration of ammonium sulfate may fall within the range of from 2 mM to 3.5 mM.

Thus, the method can comprise treating the RNA at conditions comprising a temperature of at least 70° C. and a pH of at least 8, preferably a pH of at least 9, in the presence of ammonium sulfate and therefore the presence of diammonium sulfate and/or ammonium bisulfate, preferably diammonium sulfate at a concentration value or concentration range described above.

As can be seen from the examples, ammonium sulfate at such very low concentrations ensured RNA stabilization at temperatures of e.g. 75° C., and even 85° C. and under strongly alkaline conditions. This effect was observed even during prolonged incubation. Ammonium sulfate in particular at such low concentrations as can be used in the method of the invention advantageously does not interfere with typical and important downstream applications of the processed RNA, such as PCR or qPCR applications.

pH

Since ammonium sulfate confers a strong RNA protective effect, the RNA can be treated at a temperature of at least 70° C. and strongly alkaline conditions. The method comprises treating the RNA at conditions comprising a pH of at least 8, preferably a pH of at least 9. In embodiments, the pH during treatment can be at least 8.2, at least 8.5, or at least 8.7. In embodiments, the pH during treatment can be at least 9, at least 9.2, at least 9.5, at least 9.8, at least 10, at least 10.2 or at least 10.5. According to embodiments, the pH is 14 or less, 13.5 or less, preferably 13 or less, 12.8 or less, 12.5 or less, 12.2 or less, 12 or less, or 11.75 or less.

The pH can be in a range of from 8 to 14, from 8.2 to 13.5, from 8.5 to 13, or from 8.7 to 12.5. The pH can be in a range of from 9 to 14, from 9.2 to 13.5, from 9.4 to 13, from 9.6 to 12.5, from 9.8 to 12.25, or from about 10 to about 12. pH values of from about 10 to about 12 include in particular pH values of about 10.5, about 11 and about 11.5. For example, a pH of 11 was tested in the examples and ammonium sulfate exerts a strong stabilizing effect at this high pH value. A particularly preferred pH range is 10 to 11.5.

Thus, the method can comprise treating the RNA at conditions comprising a temperature of at least 70° C. and a pH value or range as described above in the presence of ammonium sulfate, preferably at a concentration of 10 mM or less. Preferred concentration ranges and values for ammonium sulfate, including the preferred diammonium sulfate, were described above and can be combined with any of the preferred pH ranges and values.

The pH as described herein is usually the pH in a liquid composition that comprises the RNA during treatment. Said liquid composition has at least during treatment a pH as described and a temperature of at least 70° C. Different options to provide such a liquid composition are described herein.

Temperature

As described, the method comprises treating the RNA at conditions comprising a temperature of at least 70° C. The temperature can be at least 70° C., at least 72° C., at least 74° C., at least 75° C., at least 77° C., at least 78° C., at least 80° C., at least 82° C. or at least 85° C. According to one embodiment, the temperature is 95° C. or less or 90° C. or less.

The temperature can be in a range of from 70° C. to 100° C., from 70° C. to 95° C., from 73° C. to 93° C., from 75° C. to 90° C. or from about 75° C. to 85° C. (values of 76° C., 77° C., 78° C., 79° C., 80° C., 81° C., 82° C., 83° C., and 84° C. being included). A further suitable range is 72° C. to 88° C. As can be seen from the examples, ammonium sulfate even at a very low concentration provides excellent stabilization of RNA at high temperatures of e.g. 75° C. or 85° C.

Thus, the method can comprise treating the RNA at conditions comprising a temperature or temperature range as described above and a pH of at least 8, preferably a pH of at least 9, in the presence of ammonium sulfate, preferably at a concentration of 10 mM or less. Preferred concentration ranges and values for ammonium sulfate, including the preferred diammonium sulfate, and the pH were described above and can be combined with any of the preferred temperature ranges and values.

The temperature as described herein is usually the temperature in a liquid composition that comprises the RNA during treatment. Said liquid composition has at least during treatment a temperature as described. Different options to provide such a liquid composition and such temperature are described herein.

Chelating Agent

According to one embodiment, treatment at conditions comprising a temperature of at least 70° C. and a pH of at least 8, preferably a pH of at least 9, additionally occurs in the presence of a chelating agent, preferably EDTA. The chelating agent can be contacted with the RNA prior to, during or after establishing the high temperature and pH treatment conditions. The chelating agent can be an agent for complexing bivalent cations. It was surprisingly found that the chelating agent can assist and further enhance RNA stabilization during treatment at high temperature and high pH. Moreover, the chelating agent allows using particularly low concentrations of ammonium sulfate, such as e.g. 2 mM or less while maintaining a stabilization effect as was demonstrated by the inventors in examples. According to one embodiment, the chelating agent is selected from the group consisting of ethylenediaminetetraacetic acid (EDTA), ethylene glycol tetraacetic acid (EGTA), 1,2-bis-(o-Aminophenoxy)-ethane-N',N',-N',N'-tetraacetic acid tetraacetoxy-Methyl ester (BAPTA-AM), dietyldithiocarbamate (DEDTC), dicarboxymethyl-glutamic acid, nitrilotriacetic acid (NTA), ethylenediaminedisuccinic acid (EDDS) and any combination thereof. Further examples of chelating agents are acetylacetone, ethylendiamine, 2-(2-aminoethylamino)ethanol, diethylentriamine, iminodiacetate, triethylentetramine, triaminotriethylamine, nitrilotriacetate, bis(salicyliden)ethylendiamine, ethylendiaminotriacetate, ethylendiamintetraacetate (EDTA), diethylentriaminpentaacetate, 1,4,7,10-tetraazacyclododecan-1,4,7,10-tetraacetate, carboxylates such as oxalate, tartrate and citrate, dimethylglyoxime, 8-hydroxychinoline, 2,2'-bipyridine, 1,10-phenanthroline, dimercaptosuccinic acide and 1,2-bis(diphenylphosphino) ethane. In advantageous embodiments, the chelating agent is EDTA. Preferably, EDTA or other chelating agents are used at comparably low concentrations in order to avoid that they potentially interfere with certain enzymatic reactions in downstream applications of RNA such as e.g. PCR. According to one embodiment, the concentration of the one or more chelating agents during treatment is 5 mM or less, 3 mM or less, 2 mM or less, 1 mM or less, 0.8 mM or less, 0.5 mM or less, 0.25 mM or less, or 0.1 mM or less. The concentration of EDTA is preferably 1 mM or less. The chelating agent is used in a concentration where it supports the protective effects of ammonium sulfate such as in particular diammonium sulfate. The suitable concentration for an individual chelating agent can be determined by the skilled person. The concentration can be in a range of from 0.001 mM to 1 mM, from 0.005 mM to 0.8 mM, from 0.0075 mM to 0.7 mM or from 0.01 mM to 0.5 mM. These concentrations are particularly suitable for EDTA as was found by the inventors in experiments. According to one embodiment, the concentration of the chelating agent, such as EDTA, is from 0.005 mM to 0.015 mM. According to one embodiment, the concentration is the total concentration of added chelating agents present during treatment.

Preparation of the Treatment Composition and Further Embodiments

As explained above, the method of processing RNA according to the first aspect comprises treating the RNA at conditions comprising a temperature of at least 70° C. and a pH of at least 8, preferably a pH of at least 9, in the presence of ammonium sulfate, preferably at a concentration of 10 mM or less. It will be understood that the order in which the ammonium sulfate concentration, the temperature of at least 70° C. and the pH of at least 8, preferably a pH of at least 9, are achieved/provided is not limited, as long as at some point during RNA processing ammonium sulfate is present in the composition at the desired concentration at treatment conditions comprising a temperature of at least 70° C. and pH of at least 8, preferably a pH of at least 9.

The ammonium sulfate concentration of e.g. 10 mM or less may be provided for or be present first, followed by establishing the temperature of at least 70° C. and/or the pH of at least 8, preferably a pH of at least 9 (temperature and pH being provided for simultaneously or subsequently, with pH being provided for prior to or after the temperature). Also, the ammonium sulfate concentration and pH can be provided for or be present first (simultaneously or one after the other), followed by establishing the temperature. Of course, it is also possible that the ammonium sulfate concentration and the temperature are provided for or are present first (simultaneously or one after the other), followed by providing the pH. That the pH can be provided for or is present first or that the temperature can be provided for or is present first, followed by the other two conditions (simultaneously or one after the other) can also be desirable, depending on the envisaged application.

The method may comprise adjusting the temperature to at least 70° C. or any one of the aforementioned suitable temperature values or ranges prior to, simultaneously or after establishing the ammonium sulfate concentration. This can be an active step in the present method. Means and methods for achieving or adjusting the temperature as described herein are known to the skilled person and do not need detailed description here. They include the use of heating devices such as but not limited to heating plates (with or without stirring means), heating mantles, water baths, heating blocks, thermocyclers, and the like.

The method may comprise adjusting the pH to at least 8, preferably to at least 9, or any one of the aforementioned suitable pH values or ranges prior to, simultaneously or after establishing the ammonium sulfate concentration. This can be an active step in the present method. Means and methods for adjusting the pH are known to the skilled person and do not need detailed description here. They include in particular the use of strong bases such as but not limited to alkali hydroxide bases, buffer systems or alkaline organic compounds to provide the desired pH. Also, alkaline buffering agents can be used; examples include but are not limited to TAPS, AMPD, TABS, AMPSO, CHES, CAPSO, AMP, CAPS and CABS.

The method may comprise adjusting the concentration of ammonium sulfate to establish the desired concentration of e.g. ≤10 mM and/or adjusting any one of the aforementioned suitable pH values or ranges. The method may comprise contacting the RNA with the ammonium sulfate to establish a concentration of 10 mM or less.

According to one embodiment, the RNA is contacted with ammonium sulfate at a concentration effective to stabilize the RNA at the applied treatment conditions. For example the RNA can be contacted with a solution, which preferably is an aqueous solution, comprising ammonium sulfate at a concentration effective to stabilize the RNA during the high temperature and pH treatment conditions.

According to one embodiment, the RNA is contacted with ammonium sulfate (e.g. with a solution comprising ammonium sulfate) in a concentration that does not precipitate proteins.

Preferably, the method comprises adding ammonium sulfate to establish the desired concentration of e.g. 10 mM or less. This can be done by adding solid ammonium sulfate to a liquid composition comprising the RNA.

However, preferably, a solution comprising ammonium sulfate is contacted with the RNA to establish the desired ammonium sulfate concentration. Exemplary and preferred solutions are described in further detail below and it is referred to such solutions. They can be advantageously used to establish the desired ammonium sulfate concentration of e.g. 10 mM or less.

According to one embodiment, ammonium sulfate is added to establish the ammonium sulfate concentration, wherein no ammonium sulfate or only trace amounts of ammonium sulfate are present before the ammonium sulfate is added. According to one embodiment, ammonium sulfate is added wherein the RNA is not in contact with ammonium sulfate or is only in contact with trace amounts of ammonium sulfate before the ammonium sulfate is added. Ammonium sulfate is preferably added using an ammonium sulfate containing solution.

Since ammonium sulfate as used herein refers to the preferred diammonium sulfate as well as to ammonium bisulfate, it will be understood that therefore, according to one embodiment, no diammonium sulfate or only trace amounts of diammonium sulfate are present before the diammonium sulfate is added. According to one embodiment, diammonium sulfate and ammonium bisulfate are not present or only are present in trace amounts before diammonium sulfate is added.

Contacting the RNA with ammonium sulfate to establish a concentration of 10 mM or less can comprise contacting the RNA with a solution comprising ammonium sulfate at a concentration of 10 mM or less, wherein in one embodiment the pH is adjusted to at least 8, preferably to at least 9, prior to or after contacting the RNA with the solution and wherein the temperature is adjusted to at least 70° C. prior to or after contacting the RNA with the solution. It is preferred that the ammonium sulfate is already present when the RNA is exposed to the high temperature of at least 70° C. and pH conditions, because then ammonium sulfate can exert its stabilizing effect immediately when the conditions occur that can lead to degradation of the RNA. The same applies in case other ammonium sulfate concentrations are used.

Contacting the RNA with ammonium sulfate to establish a concentration of 10 mM or less can comprise contacting the RNA with a solution comprising ammonium sulfate at a concentration of 10 mM or less and having a pH of at least 8, preferably a pH of at least 9, wherein the temperature is adjusted to at least 70° C. prior to or after contacting the RNA with the solution. This is a preferred embodiment of the present method and is very useful e.g. if RNA is bound to an anion exchange matrix and said treatment conditions are used to release the RNA from the anion exchange matrix. In particular, the temperature can be raised to at least 70° C. after contacting the RNA with the ammonium sulfate containing solution which preferably has a pH of at least 8, preferably a pH of at least 9. However, contacting the RNA with ammonium sulfate to establish a concentration of 10 mM or less can comprise contacting the RNA with a solution having a temperature of at least 70° C., a pH of at least 8, preferably a pH of at least 9, and comprising ammonium sulfate at a concentration of 10 mM or less, and contacting the RNA with the heated solution. This is also a preferred embodiment of the present method and is also particularly suitable for releasing RNA from an anion exchange matrix, e.g. using a column based anion exchange matrix. The same applies in case other ammonium sulfate concentrations are used.

Contacting the RNA with ammonium sulfate to establish a concentration of 10 mM or less can comprise contacting the RNA with a solution comprising ammonium sulfate at a concentration of 10 mM or less and having a temperature of at least 70° C., wherein the pH is adjusted to at least 8, preferably to at least 9, prior to or after contacting the RNA with the solution. The pH can be adjusted to at least 8, preferably to at least 9, after contacting the RNA with the solution. Also, contacting the RNA with ammonium sulfate to establish a concentration of 10 mM or less can comprise contacting the RNA with a solution comprising ammonium sulfate at a concentration of 10 mM or less, wherein the pH is adjusted to at least 8, preferably to at least 9, after contacting the RNA with the solution and wherein the temperature is adjusted to at least 70° C. after contacting the RNA with the solution. The same applies in case other ammonium sulfate concentrations are used. Adjusting the pH to at least 8, preferably to at least 9, after contacting the RNA with the solution may be desirable for example if it is intended to release both DNA and RNA that is bound to an anion exchange matrix.

It will be understood that contacting the RNA with ammonium sulfate to establish a concentration of e.g. 10 mM or less can also comprise contacting the RNA with a solution having a temperature of at least 70° C., a pH of at least 8, preferably a pH of at least 9, or both, followed by contacting the RNA with ammonium sulfate to provide the desired concentration of e.g. 10 mM or less. In this embodiment, RNA stabilization is attained once ammonium sulfate is present. Albeit the RNA initially is exposed to high temperature and/or high pH conditions in the absence of ammonium sulfate, it is efficiently stabilized once the ammonium sulfate is added. As can be seen from the examples, RNA degradation is particularly pronounced after an initial incubation period of 1 or 2 min, and RNA therefore also profits from ammonium sulfate even if it is contacted with the ammonium sulfate after the temperature and/or pH conditions are already established. This contacting preferably occurs within 2 min or less, 1 min or less, 45 sec or less, or 30 sec or less upon treating the RNA under conditions involving a temperature of at least 70° C. and a pH of at least 8, preferably a pH of at least 9. Such embodiments can be e.g. used in case the treatment conditions are used to elute the RNA from an anion exchange matrix. The elution can comprise at least 2 steps, wherein the bound RNA is contacted with an alkaline elution solution first, followed by contacting with ammonium sulfate (preferably comprised in a solution) to protect the RNA.

According to one embodiment, the RNA containing composition that is treated at conditions comprising a temperature of at least 70° C. has a pH of from 9.5 to 12.5, preferably 10 to 12 and comprises ammonium sulfate in a concentration of from 0.5 mM to 7 mM, preferably 0.75 mM to 5 mM. The RNA containing composition that is treated at conditions comprising a temperature of at least 70° C. has in embodiments a pH of from 10 to 12 and comprises ammonium sulfate in a concentration of from 0.5 mM to 5 mM, preferably 0.75 mM to 3 mM. As described above, the RNA containing composition may also comprise a chelating agent, preferably EDTA. Thus, the RNA containing composition that is treated at conditions comprising a temperature of at least 70° C. has in embodiments a pH of from 9.5 to 12.5, preferably 10 to 12, comprises ammonium sulfate in a concentration of from 0.5 mM to 7 mM, preferably 0.75 mM to 5 mM and additionally comprises EDTA. In embodiments, EDTA is comprised in a concentration of from 0.005 mM to 1 mM, preferably 0.01 mM to 0.5 mM. EDTA can be comprised in a concentration of from 0.005 mM to 0.015 mM. The treatment temperature is in embodiments in a range of 70° C. to 90° C., 72° C. to 88° C. or 75° C. to 85° C. As described herein, said composition may comprise an anion exchange matrix, e.g. in the form of magnetic particles, if the technology of the invention is used in order to release/elute RNA from an anion exchange matrix.
Incubation According to one embodiment, treating the RNA comprises incubating the RNA. In particular, treating the RNA can comprise incubating the RNA at the temperature and pH conditions described in detail above.

The RNA can be incubated for at least 1 min, at least 2 min, at least 3 min, at least 5 min, at least 7 min, or at least 10 min. It can be incubated for up to 60 min, up to 30 min, up to 20 min, up to 18 min, up to 15 min, up to 12 min, up to 10 min, up to 7 min, up to 5 min, up to 3 min, or up to 2 min. According to preferred embodiments, the RNA is incubated for 1 min to 20 min, 2 min to 15 min, 5 min to 12 min or 7 min to 10 min.

When ammonium sulfate at a concentration described in detail above is present during RNA incubation, it protects the RNA from degradation. This is because RNA ammonium sulfate already at concentration of 10 mM or less confers stabilization of the RNA at the temperature and pH conditions defined above. However, as described it is also contemplated to shortly incubate RNA in the absence of ammonium sulfate first, followed by the addition of ammonium sulfate to prevent degradation.

Incubation at the temperature and pH conditions defined above can be followed by an incubation period at a temperature of below 70° C., such as in particular at room temperature. "Room temperature" as used herein in particular can mean a temperature of 15° C. to 28° C. Furthermore, the RNA containing composition can be cooled after applying the treatment conditions of 70° C. or higher, e.g. at a temperature if 0° C. to 20° C. or 2° C. to 10° C. For example, incubation at the temperature and pH conditions defined above can be followed by an incubation period of up to 60 min, up to 50 min, up to 40 min, up to 30 min, up to 20 min, or at least 10 min at a temperature of below 70° C., such as in particular at room temperature or below. Ammonium sulfate at a concentration defined above is preferably also present in this case.

As indicated above, while preferably ammonium sulfate at a concentration defined above is present during the whole period of RNA incubation, it is also contemplated that treating the RNA can comprise incubating the RNA shortly in the absence of ammonium sulfate first, followed by the addition of ammonium sulfate during or after the incubation. Thus, it is contemplated to incubate the RNA at the temperature and pH conditions defined above first, followed by establishing an ammonium sulfate concentration of 10 mM or less. The ammonium sulfate concentration can for example be established after a short incubation of 2 min, 1 min or 45 sec or less. As can be seen from the examples, the RNA-degrading effect of high temperature and pH is particularly pronounced after this period. Therefore, RNA can also profit from the stabilizing effect of ammonium sulfate if the ammonium sulfate concentration is established after a short incubation at high temperature and pH. However, it is preferred that the ammonium sulfate is present during the whole time period where the RNA is exposed to a temperature of at least 70° C. and a pH of at least 8, preferably a pH of at least 9.

According to one embodiment, the incubation occurs in the presence of one or more proteolytic enzymes or other enzymatic compounds, wherein the one or more proteolytic enzymes or other enzymatic compounds are inactivated during incubation at the treatment conditions involving a temperature of at least 70° C. and a pH of at least 8, preferably a pH of at least 9. The one or more proteolytic enzymes or other enzymatic compounds can be inactivated by heat, by alkaline pH or both. One or more of such enzymes and enzymatic compounds are often used when isolating RNA from a sample, in particular a biological sample. They can be carried over during the isolation process into the purified RNA. As described herein, the temperature and pH treatment conditions used in the method of the invention can be advantageously utilized to release, in particular elute, RNA from an anion exchange matrix. The presence of ammonium sulfate protects and stabilizes the RNA during said release process. Thus, these conditions can be advantageously used in a RNA isolation method. In case a proteolytic enzyme or other enzymatic compound was used during said isolation process, the incubation at the high temperature and pH conditions defined above can advantageously inactivate any proteases or other enzymatic compounds that were carried over and accordingly, may still be present when treating or incubating the RNA, e.g. in order to elute the RNA from an anion exchange matrix. The presence of ammonium sulfate protects the RNA and thus allows to apply harsh conditions as are required for the inactivation in particular of robust enzymes such as proteinase K (which may include a temperature of about 75° C. or higher).

A proteolytic enzyme is an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K.

Proteolytic enzymes such as in particular proteinase K are frequently used in RNA processing methods, e.g. for lysis or digestion of RNA-containing samples. It is desirable to inactivate proteolytic enzymes such as proteinase K that were not removed during purification in such methods at some point (e.g., during release of RNA from an anion exchange matrix), because they can interfere with downstream applications. For example, proteinase K is active at 50° C. and therefore can interfere with reverse transcription of RNA or other downstream applications involving the use of enzymes.

Other enzymatic compounds that can be present and can be inactivated comprise nucleases. Examples of nucleases are DNAses and RNAses, in particular RNAses.

Ammonium Sulfate Containing Solution

As described above, the ammonium sulfate is preferably comprised in a solution that is contacted with the RNA. Said solution can be accordingly used to establish the ammonium sulfate concentration in the RNA containing composition that is subjected to the treatment conditions.

In line with the above disclosure that ammonium sulfate as used herein refers to diammonium sulfate as well as to ammonium bisulfate, the ammonium sulfate containing solution can be a solution comprising diammonium sulfate, ammonium bisulfate, or both, with diammonium sulfate being preferred.

Hence, according to one embodiment a method for processing RNA is provided, comprising contacting the RNA with a solution comprising ammonium sulfate and treating the RNA at conditions comprising a temperature of at least 70° C. and a pH of at least 8, preferably a pH of at least 9, in the presence of ammonium sulfate. Suitable ammonium sulfate concentrations are described above. Preferably, the RNA is treated in the presence of ammonium sulfate at a concentration of 10 mM or less.

The solution can comprise ammonium sulfate at a concentration of 50 mM or less, 40 mM or less, 30 mM or less, 25 mM or less, 20 mM or less, 15 mM or less or preferably 10 mM or less.

It can comprise ammonium sulfate at a concentration value or range described above when discussing the ammonium sulfate concentrations that can be present when treating the RNA at a temperature of at least 70° C. and a pH of at least 8, preferably a pH of at least 9. It is referred to the above disclosure which also applies here. According to one embodiment, the solution comprises ammonium sulfate at a concentration of from 0.1 mM to 10 mM, from 0.25 mM to 10 mM, from 0.5 mM to 9 mM, from 0.7 mM to 8 mM, from 1 mM to 7 mM, from 1.5 mM to 6 mM, from 1.75 mM to 5 mM or from 2 mM to 4 mM, from 2 mM to 3.5 mM, or about 2.5 mM. Preferably, it comprises diammonium sulfate at one of the aforementioned concentrations.

According to one embodiment, the solution has a pH of at least 8, preferably a pH of at least 9. The solution can be advantageously used to establish the alkaline pH value desired for the treatment conditions. It can have a pH value or pH range described above when discussing the pH conditions that can be present when treating the RNA at a temperature of at least 70° C. It is referred to the above disclosure which also applies here. The solution can have a pH in a range from 8 to 14, from 8.2 to 13.5, from 8.5 to 13, or from 8.7 to 12.5. According to one embodiment, the solution has a pH in a range from 9 to 14, from 9.2 to 13.5, from 9.4 to 13, from 9.6 to 12.5, from 9.8 to 12.25 or from 10 to 12. A particularly preferred pH range is 10 to 11.5.

The alkaline pH of the solution can be achieved by including at least one base. According to one embodiment, the solution comprises one or more salts and/or other compounds to provide for a pH of at least 8, preferably a pH of at least 9. Typical salts that can be comprised in the solution to provide for the alkaline pH are one or more alkali hydroxide salts, such as sodium hydroxide (NaOH) and/or potassium hydroxide (KOH). Thus, according to one embodiment, the solution can comprise one or more alkali hydroxide salts. The solution can comprise NaOH, KOH, or both.

For example the solution can comprise NaOH and/or KOH at a concentration sufficient to provide a pH of at least 8, preferably a pH of at least 9, or any of the pH values and ranges discussed above, in particular a pH in a range from 9 to 14, from 9.2 to 13.5, from 9.4 to 13, from 9.6 to 12.5, from 9.8 to 12.25 or from 10 to 12.

According to one embodiment the solution comprises from 10 mM to 50 mM, from 12 mM to 40 mM, from 15 mM to 35 mM or about 20 mM to 30 mM of NaOH, KOH or both. According to one embodiment, the indicated concentrations are the total concentrations of alkali hydroxide salts comprised in the solution.

Preferably, the solution is aqueous. According to one embodiment, the solution is a solution for releasing RNA from an anion exchange matrix. Thus, the solution can be an elution solution, in particular an elution buffer.

The solution can comprise further ingredients such as one or more salts. Salts can be comprised e.g. in a concentration of 100 mM or less each (such as 90 mM or less, 80, 70, 60 or 50 mM or less or from 10 to 100 mM, from 20 to 80 mM or from 30 to 70 mM). The solution can comprise one or more alkali metal halides, such as NaCl and/or KCl. It can comprise one or more alkali metal halides, in particular KCl, at a concentration of 100 mM or less each (such as 90 mM or less, 80, 70, 60 or 50 mM or less or from 10 to 100 mM, from 20 to 80 mM or from 30 to 70 mM). According to one embodiment, the total concentration or ionic strength of alkali metal halides is 100 mM or less (such as 90 mM or less, 80, 70, 60 or 50 mM or less or from 10 to 100 mM, from 20 to 80 mM or from 30 to 70 mM). According to one embodiment, salts are comprised in a total concentration or ionic strength of 100 mM or less (such as 90 mM or less, 80, 70, 60 or 50 mM or less or from 10 to 100 mM, from 20 to 80 mM or from 30 to 70 mM).

The solution can be a low salt solution. It is preferred that the solution is a low salt solution, because high salt concentrations or high ionic strength can interfere with downstream applications of RNA. A low salt solution can in particular be a solution is a solution having an ionic strength of <100 mM.

Therefore, according to one embodiment, the solution is a solution having an ionic strength of ≤100 mM, ≤80 mM or ≤50 mM.

According to one embodiment, the solution is buffered. The solution can comprise one or more buffering agents, e.g. a buffering agent selected from Tris-HCl, MOPS, HEPES PIPES, and MES. Hence, treating of the RNA at conditions comprising a temperature of at least 70° C. and a pH of at least 8, preferably a pH of at least 9, in the presence of ammonium sulfate can occur in the presence of a buffering agent. Suitable alkaline buffering agents were also described above and it is referred to the above disclosure. As described, the buffering agent can be comprised in the solution that is contacted with the RNA. However, the buffering agent can also be carried over from a previous step, e.g. a washing step, resulting in a buffered, or partially buffered, RNA containing composition that is then treated using the conditions of the invention.

According to one embodiment, the solution comprises a chelating agent. Details and advantages were described above and it is referred to the above disclosure. According to one embodiment, the chelating agent is selected from the group consisting of ethylenediaminetetraacetic acid (EDTA), ethylene glycol tetraacetic acid (EGTA), 1,2-bis-(o-Aminophenoxy)-ethane-N',N',-N',N'-tetraacetic acid tetraacetoxy-Methyl ester (BAPTA-AM), diethyldithiocarbamate (DEDTC), dicarboxymethyl-glutamic acid, nitrilotriacetic acid (NTA), ethylenediaminedisuccinic acid (EDDS) and any combination thereof. Further suitable chelating agents were also described above. In advantageous embodiments, the solution comprises EDTA as chelating agent. According to one embodiment, the solution comprises the one or more chelating agents at a concentration of 5 mM or less, 3 mM or less, 2 mM or less, 1 mM or less, 0.8 mM or less, 0.5 mM or less, 0.25 mM or less, or 0.1 mM or less. The concentration of EDTA is preferably 1 mM or less. The solution may comprise EDTA or other chelating agents at a concentration of e.g. from 0.001 mM to 1 mM, from 0.005 mM to 0.8 mM, from 0.0075 mM to 0.7 mM or from 0.01 mM to 0.5 mM. These concentrations are particularly suitable for EDTA. According to one embodiment, the concentration of the chelating agent, such as EDTA, is from 0.005 mM to 0.015 mM. According to one embodiment, the concentration is the total concentration of chelating agents present in the solution.

The solution can comprise components assisting downstream applications of RNA such as PCR applications, e.g. polyethylene glycol (PEG).

The solution can be a solution that is suitable for application, e.g. as a buffer, in PCR. The solution can be a solution that is suitable for application, e.g. as a buffer, in PCR directly or after lowering the pH of the solution to a pH at which enzymes used during PCR are active.

According to one embodiment, the solution does not comprise non-complexed $Mg^{2+}$ and/or does not comprise non-complexed $Ca^{2+}$. According to one embodiment, the solution does not comprise non-complexed bi-valent cations. According to one embodiment, the solution does not comprise $Mg^{2+}$ and/or does not comprise $Ca^{2+}$. According to one embodiment, the solution does not comprise bi-valent cations at all.

According to one embodiment, the solution does not comprise an organic solvent.

After contacting the ammonium sulfate containing solution with the RNA, the resulting composition can be heated to a temperature of at least 70° C. As described above, the solution preferably has a pH of at least 8, preferably a pH of at least 9, as this avoids additional steps for adjusting the pH value to at least 8, preferably a pH to at least 9 (other suitable and preferred pH values and ranges were described above). Thus, the ammonium sulfate containing solution can have a pH of at least 8, preferably a pH of at least 9, and wherein after contacting the RNA with the solution, the temperature is adjusted to a temperature of at least 70° C.

However, also contemplated are embodiments wherein a heated ammonium sulfate containing solution is contacted with the RNA. The solution can have a temperature of at least 70° C., at least 75° C., at least 80° C. or at least 85° C. It can have a temperature value or range described above when discussing what temperature conditions can be present when treating the RNA. The solution can have a temperature in a range from 70° C. to 100° C., from 70° C. to 95° C., from 75° C. to 90° C. or from about 75° C. to 85° C.

According to one embodiment, the solution has a pH of from 9.5 to 12.5, preferably 10 to 12 and comprises ammonium sulfate in a concentration of from 0.5 mM to 7 mM, preferably 0.75 mM to 5 mM. The solution has in embodiments a pH of from 10 to 12 and comprises ammonium sulfate in a concentration of from 0.5 mM to 5 mM, preferably 0.75 mM to 3 mM. As described above, the solution may furthermore comprise a chelating agent, preferably EDTA. Thus, the solution has in embodiments a pH of from 9.5 to 12.5, preferably 10 to 12, comprises ammonium sulfate in a concentration of from 0.5 mM to 7 mM, preferably 0.75 mM to 5 mM and additionally comprises EDTA. In embodiments, EDTA is comprised in the solution in a concentration of from 0.005 mM to 1 mM, preferably 0.01 mM to 0.5 mM. According to one embodiment, EDTA is comprised in the solution in a concentration of from 0.005 mM to 0.015 mM. As discussed, the solution preferably is an aqueous solution. It may comprise one or more alkali hydroxide salts, such as NaOH, to achieve the high pH values. As described, such solutions can be used for releasing RNA from an anion exchange matrix.

Release of RNA Bound to an Anion Exchange Matrix

According to one embodiment the RNA is present bound to an anion exchange matrix and the RNA is released from said anion exchange matrix during the treatment. Thus, the treatment conditions used in the method according to the present invention are particularly useful to release RNA from an anion exchange matrix. These conditions therefore can be advantageously used to elute RNA from an anion exchange matrix. Preferably, the ammonium sulfate containing solution described in detail above is contacted with an anion exchange matrix to which RNA is bound in order to release/elute the RNA from the anion exchange matrix, wherein release/elution occurs at a pH of at least 8, preferably a pH of at least 9, and a temperature of at least 70° C. As described above, preferably a solution is used that has the desired pH value of at least 8, preferably of at least 9. The solution can be heated to at least 70° C. prior to contacting the solution with the anion exchange matrix for elution and/or heating to at least 70° C. can occur after the solution has been contacted with the anion exchange matrix to which the RNA is bound.

"Releasing" RNA from an anion exchange matrix as used herein in particular refers to the process wherein the RNA is set free from the anion exchange matrix. The RNA can be set free from the anion exchange matrix into a solution. "Releasing" RNA in particular refers to eluting RNA from an anion exchange matrix, preferably using an ammonium sulfate containing solution as described in detail above. The anion exchange matrix (e.g. particles comprising an anion exchange surface) can be separated from the RNA containing solution to provide an eluate that does not contain the anion exchange matrix.

RNA can be released from an anion exchange matrix at a pH of at least 8. Typically, RNA is released very quickly from an anion exchange matrix at a pH of at least or above 9 and the release is further facilitated by applying a temperature of at least 70° C. The high temperature and pH conditions contribute to and facilitate the release of RNA from the anion exchange matrix. Moreover, as described above, they also allow to inactivate, e.g. denature, any undesirable enzymes that may be present, such as in particular RNAses and proteinases such as proteinase K. As described above, the ammonium sulfate stabilizes and thus protects the RNA during harsh elution conditions that involve a temperature of at least 70° C. and a pH of at least 8, preferably a pH of at least 9, thereby inhibiting RNA degradation. Thus, the presence of ammonium sulfate ensures that the high temperature and pH conditions can be applied and at the same time, RNA quality can be preserved.

Thus, also provided is a method of releasing RNA from an anion exchange matrix to which the RNA is bound, said method comprising treating the RNA at conditions comprising a temperature of at least 70° C. and a pH of at least 8, preferably a pH of at least 9, in the presence of ammonium sulfate (preferably at a concentration of 10 mM or less) to release the RNA from the anion exchange matrix.

The treatment conditions for releasing the RNA from the anion exchange matrix can be as described in detail above. Thus, in particular the temperature and pH conditions as well as the concentration of ammonium sulfate can be as described above and it is referred to said description for the sake of conciseness. Preferably, the anion exchange matrix with the bound RNA is contacted with the ammonium sulfate containing solution (described in detail above) in order to effectuate the release of the RNA. As described above, said solution preferably has a pH of at least 8, preferably a pH of at least 9, further suitable and preferred pH values and ranges are also described above. The solution can be pre-heated to a temperature of at least 70° C. or heating to at least 70° C. can occur after the ammonium sulfate containing solution, which preferably has a pH of at least 8, preferably a pH of at least 9, has been contacted with the anion exchange matrix to which the RNA is bound.

Ammonium sulfate can in particular be present during release of the RNA at a concentration of 50 mM or less, 40 mM or less, 30 mM or less, 25 mM or less, 20 mM or less, 15 mM or less and preferably 10 mM or less. It can be present during release of the RNA at a concentration of from 0.25 mM to 10 mM, from 0.5 mM to 9 mM, from 0.7 mM to 8 mM, from 1 mM to 7 mM, from 1.5 mM to 6 mM, from 1.75 mM to 5 mM, from 2 mM to 4 mM, from 2 mM to 3.5 mM, or about 2.5 mM.

According to one embodiment, the RNA is not exposed to or contacted with ammonium sulfate containing reagents prior to releasing the RNA from the anion exchange matrix, which preferably occurs using the ammonium sulfate containing solution that is described in detail above.

The pH used for releasing/eluting the RNA can be in a range from 8 to 14, from 8.2 to 13.5, from 8.5 to 13, or from 8.7 to 12.5. The pH used for releasing/eluting the RNA can in particular be in a range from 9 to 14, from 9.2 to 13.5, from 9.4 to 13, from 9.6 to 12.5, from 9.8 to 12.25 or from 10 to 12. A particularly preferred pH range is 10-11.5.

The temperature used to release/elute the RNA can in particular be in a range from 70° C. to 100° C., from 70° C. to 95° C., from 75° C. to 90° C. or from about 75° C. to 85° C.

The anion exchange matrix with the bound RNA can be contacted with a solution to release the RNA from the anion exchange matrix. The solution preferably is an ammonium sulfate solution as has been described above and again, it is referred to said description for the sake of conciseness. Thus, also a method for releasing RNA from an anion exchange matrix to which the RNA is bound is provided, said method comprising contacting the anion exchange matrix with the bound RNA with a solution comprising ammonium sulfate (preferably at a concentration of 10 mM or less) and treating the RNA at conditions comprising a temperature of at least 70° C. and a pH of at least 8, preferably a pH of at least 9, in the presence of ammonium sulfate (preferably at a concentration of 10 mM or less) to release the RNA from the anion exchange matrix. Preferably, the ammonium sulfate containing solution is a solution as described above. The pH can be adjusted to a pH of at least 8, preferably to a pH of at least 9, prior to or after contacting the RNA with the solution. However, preferably, the pH used during release/ elution is established by the ammonium sulfate containing solution to avoid adjustment steps. Thus, in one embodiment the anion exchange matrix with the bound RNA is contacted with a solution comprising ammonium sulfate (preferably at a concentration of 10 mM or less) and having a pH of at least 8, preferably a pH of at least 9. The temperature can be adjusted to at least 70° C. prior to or after contacting the RNA with the solution, or by adding a heated solution to the anion exchange matrix.

Adjusting the temperature to at least 70° C. after contacting the RNA with the ammonium sulfate containing solution is particularly preferred if particles, such as magnetic particles, comprising an anion exchange surface are used as anion exchange matrix. Using such particles, the temperature can very conveniently be adjusted after the solution has been added and in the presence of the particles. If desired, the particles can be agitated or stirred while adjusting the temperature. Alternatively, the solution contacted with the RNA can have a temperature of at least 70° C. Thus, a pre-heated solution can be used. Using a pre-heated solution is particularly feasible if the RNA is bound to a resin or membrane or to an anion exchange matrix comprised in a column.

Adjusting the pH to at least 8, preferably to at least 9, after contacting the RNA with a solution comprising ammonium sulfate (preferably at a concentration of 10 mM or less) and optionally having a temperature of at least 70° C. may be desirable for example if it is intended to release both DNA and RNA that is bound to an anion exchange matrix. In this case, DNA can be released from the anion exchange matrix first at a first pH below 8, preferably a pH below 9, and the pH can then be raised to a second pH of at least 8, preferably to a second pH of at least 9, thereafter to release the RNA from the anion exchange matrix at the second pH.

According to one embodiment, the method comprises treating the RNA, preferably when being in contact with ammonium sulfate, at a temperature of at least 70° C. and a pH of at least 8, preferably a pH of at least 9, to release the RNA bound to an anion exchange matrix. As described, it is advantageous if ammonium sulfate is present when the RNA is released or separated from the matrix using such harsh conditions. However, using the high temperature and pH conditions described herein, RNA is typically released very quickly. Thus, RNA can also be released from an anion exchange matrix first, and the obtained RNA containing solution or eluate can then be stabilized with the ammonium sulfate thereafter. Adding ammonium sulfate after an initial short treatment in the absence of ammonium sulfate has also been described above and it is referred to this description. As described above, ammonium sulfate should be added quickly, to avoid RNA degradation.

Anion Exchange Matrix

The anion exchange matrix used is capable of binding RNA under appropriate conditions. The type of anion exchange matrix to which the RNA is bound is not particularly limited. Suitable anion exchange matrices and RNA binding conditions are known to the skilled person. It can be a resin, a membrane or a particle. The anion exchange matrix can be a solid support comprising an anion exchange surface. The term "surface" as used herein in particular refers to the portion of a solid support which comes into contact with a liquid when the solid support is contacted therewith. The solid support provides a surface that provides, e. g. carries, anion exchange moieties.

Suitable formats of the solid support include but are not limited to particles such as beads, membranes, filters, plates, columns, vessels and dipsticks. According to one embodiment, the surface comprising anion exchange moieties is provided by a vessel, for example the inner surface of a vessel. The inner surface of the surface or portions thereof can be functionalized, e.g. coated, with anion exchange moieties. Examples of respective vessels that can be functionalized with anion exchange moieties include but are not limited to microtubes and wells of a microplate. The anion exchange surface can be provided in form of a coating that provides anion exchange groups, e.g. as a coating on a vessel or other device such as a coating on a microfluidic channel or a coating on particles or other solid support. The anion exchange matrix can also be comprised in a column. When particles are used, the particles are according to one embodiment not comprised in a column or other device that would prevent the particles from moving in a solution. The particles preferably can move, e.g. when being agitated.

The anion exchange matrix can in particular be provided by magnetic particles that provide an anion exchange surface. For many applications, particles, in particular magnetic particles, comprising an anion exchange surface are convenient, and are therefore preferred herein. Using magnetic particles simplifies the processing of the particles because they can be processed and in particular separated by the aid of a magnet which is advantageous for automation. The particles may have ferrimagnetic, ferromagnetic, paramagnetic or superparamagnetic properties and preferably are superparamagnetic. Such properties can be achieved by incorporating a suitable magnetic material into the particles. Suitable methods are known to the skilled person. Preferably, the magnetic material is completely encapsulated e.g. by the silica, polysilicic acid, glass or polymeric material that is used as base material for the particles.

In particular, particles, especially magnetic particles, can very easily and conveniently be exposed to and incubated at high temperatures of above 70° C., for example in a reaction vessel, beaker or similar device. In particular, when the particles are not comprised in a column or other device that would prevent the particles from moving, it is advantageously also possible to agitate the particles and this can support a uniform exposure to heat.

The anion exchange matrix comprises anion exchange moieties that provide anion exchange groups that can interact with the RNA. Anion exchange moieties comprise one or more groups capable of anion exchange such as e.g. amine groups. Under appropriate conditions, in particular appropriate pH conditions, anion exchange moieties are capable of binding anions. However, they do not need to be associated with an anion. The anion exchange groups may be of the same type, however, different types of anion exchange groups may also be used. The anion exchange moieties can be selected from monoamines, diamines, polyamines, nitrogen-containing aromatic or aliphatic heterocyclic groups, cyclic amines, aromatic amines and heterocyclic amines. According to one embodiment, the anion exchange moieties comprise at least one primary, secondary and/or tertiary amino group. Quaternary amines are also known as anion exchange moieties.

In preferred embodiments, the anion exchange group comprises an amino group selected from the group consisting of primary, secondary and tertiary amines. In one embodiment said amine has the formula $$R_3N, R_2NH, RNH_2 \text{ and/or } X—(CH_2)_n—Y$$

wherein

X is $R_2N$, RNH or $NH_2$,

Y is $R_2N$, RNH or $NH_2$,

R is independently of each other a linear, branched or cyclic alkyl, alkenyl, alkynyl or aryl substituent which may comprise one or more heteroatoms, preferably selected from O, N, S and P, and n is an integer in the range of from 0 to 20, preferably 0 to 18.

Hence, the anion exchange groups may have a protonatable group and optionally may have more than one protonatable group which may be the same or different. A protonatable group preferably is a chemical group which is neutral or uncharged at a high pH value and is protonated at a low pH value, thereby having a positive charge. In particular, the protonatable group is positively charged at the binding pH at which binding of the RNA occurs. Preferably, the pKa value of the (protonated) protonatable group is in the range of from about 8 to about 13, more preferably from about 8.5 to about 12 or from about 9 to about 11.5.

Examples of suitable anion exchange groups are in particular amino groups such as primary, secondary and tertiary amino groups as well as cyclic amines, aromatic amines and heterocyclic amines, preferably tertiary amino groups. The amino groups preferably bear alkyl, alkenyl, alkynyl and/or aromatic substituents, including cyclic substituents and substituents which together with the nitrogen atom form a heterocyclic or heteroaromatic ring. The substituents preferably comprise 1 to 20 carbon atoms, more preferably 1 to 12, 1 to 8, 1 to 6, 1 to 5, 1 to 4, 1 to 3 or 1 or 2 carbon atoms. They may be linear or branched and may comprise heteroatoms such as oxygen, nitrogen, sulfur, silicon and halogen (e.g. fluorine, chlorine, bromine) atoms. Preferably, the substituents comprise not more than 4, more preferably not more than 3, not more than 2 or not more than 1 heteroatom. In one embodiment the anion exchange group preferably carries 1 to 10 amino groups. More preferably the anion exchange groups carries 2 to 8, and particularly the anion exchange group carries 2 to 6 amino groups.

Examples of suitable amine functions are primary amines such as aminomethyl (AM), aminoethyl (AE), aminoalkyl, alkylaminoalkyl, dialkylaminoalkyl such as diethylamino-ethyl (DEAE), ethylendiamine, diethylentriamine, triethyl-entetraamine, tetraethylenpentaamine, pentaethylen-hexaamine, trimethylamino (TMA), triethylaminoethyl (TEAE), linear or branched polyethylenimine (PEI), car-boxylated or hydroxyalkylated polyethylenimine, jeffamine, spermine, spermidine, 3-(propylamino)propylamine, polyamidoamine (PAMAM) dendrimers, polyallylamine, polyvinylamine, N-morpholinoethyl, polylysine, and tet-raazacycloalkanes. According to one embodiment, the pri-mary amine is a polyallylamine. Furthermore, a polypropyl-enimine tetramine dendrimer (DABAM) can be used.

Suitable anion exchange matrices and anion exchange groups and in particular also anion exchange particles are also disclosed in EP 15 171 466.4 to which it is referred. Examples of suitable particles and anion exchange groups are also described in WO 2010/072834 A1, DE10 2008 063 001A1, WO2010072821A1, DE 10 2008 063 003 and WO 99/29703 to which it is referred. Suitable anion exchange matrices that can be used for binding RNA are also known as charge switch materials.

Suitable anion exchange matrices and anion exchange groups, in particular poly(allylamines), are also disclosed in WO 2014/066376 A1 to which it is referred.

Method for Isolating RNA from a Sample

The method of processing RNA according to the present invention can be advantageously used for isolating RNA from a sample. Thus, a method of isolating RNA from a sample is provided, the method comprising:

optionally releasing the RNA from the sample;

binding the RNA to an anion exchange matrix;

optionally washing the bound RNA;

treating the RNA at conditions comprising a temperature of at least 70° C. and a pH of at least 8, preferably a pH of at least 9, in the presence of ammonium sulfate (preferably at a concentration of 10 mM or less) to release the RNA from the anion exchange matrix.

Thus, the method comprises a step of releasing the RNA from the anion exchange matrix at conditions comprising a temperature of at least 70° C. and a pH of at least 8, preferably a pH of at least 9, in the presence of ammonium sulfate. As mentioned above, ammonium sulfate as used herein refers to diammonium sulfate as well as to ammo-nium bisulfate. Since all disclosures described in this appli-cation for ammonium sulfate in general specifically and particularly apply to the preferred embodiment diammo-nium sulfate, the RNA can in particular also be treated with diammonium sulfate in a method of isolating RNA accord-ing to the invention.

Suitable and preferred ammonium sulfate concentrations were described above. The ammonium sulfate concentration is preferably 10 mM or less. The RNA can be treated at conditions comprising a temperature of at least 70° C. and a pH of at least 8, preferably a pH of at least 9, in the presence of ammonium sulfate at a concentration of 10 mM or less to elute the RNA from the anion exchange matrix. The treatment conditions described herein can thus be advantageously used within an RNA isolation method in order to elute RNA that is bound to an anion exchange matrix. Details regarding the release conditions, the anion exchange matrix and the associated advantages were described above and it is referred to the respective disclo-sure.

According to one embodiment, the method comprises:

preparing from a sample, preferably a biological sample, a binding mixture comprising i) RNA;

ii) an anion exchange matrix, preferably particles such as magnetic particles providing an anion exchange surface;

iii) optionally at least one salt, wherein the binding mixture has a pH so that RNA binds to the anion exchange matrix, separating the anion exchange matrix with the bound RNA from the remaining binding mixture;

optionally washing the bound RNA; and releasing the RNA from the anion exchange matrix at conditions comprising a temperature of at least 70° C. and a pH of at least 8, preferably a pH of at least 9, in the presence of ammonium sulfate, the ammonium sulfate preferably being present at a concentration of 10 mM or less.

According to one embodiment, the RNA is isolated from a sample that has not been contacted with ammonium sulfate for precipitating protein. According to one embodiment, the RNA is isolated from a sample that has not been contacted with or stored in a solution comprising ammonium sulfate. According to one embodiment, the RNA is isolated from a sample that has not been contacted with ammonium sulfate.

The individual steps are now described in more detail.

The sample containing the RNA can be treated in order to release the RNA or remove impurities. Such methods are known in the art and do not need further detailed description here. Releasing the RNA from the sample can comprise lysing the sample, homogenizing the sample, digesting the sample or a combination thereof. Suitable sample types are described below. In particular, the sample can be a biological sample. According to one embodiment, said treatment step involves the use of one or more enzymes, in particular protein degrading enzymes, e.g. hydrolases or proteases. Using a proteolytic enzyme was found to improve the purity of the obtained eluate. In particular, the amount of protein contaminations is significantly reduced. Exemplary prote-olytic enzymes have been described above and include but are not limited to proteinases and proteases such as in particular subtilisins, subtilases, and alkaline serine pro-teases. A proteolytic enzyme commonly used in RNA iso-lation methods is proteinase K. It may also be desirable to e.g. digest DNA from the sample with one or more nucleases such as DNAses.

As described above, even though such enzymes have advantages during preparation of the RNA, it is desirable to remove them in the course of the isolation process to provide pure RNA. In particular, it is advantageous to ensure that no active enzymes are comprised in the purified RNA. The present method advantageously allows to efficiently inacti-vate such enzymes if still present. In particular, the present method advantageously allows to inactivate (e.g. denature) such enzymes when releasing the RNA from the anion exchange matrix at the treatment conditions comprising a temperature of at least 70° C. and a pH of at least 8, preferably a pH of at least 9. The RNA is preserved at these harsh conditions due to the presence of the ammonium sulfate. With the present method, also enzymes that are active at and resistant to rather high temperatures such as proteinase K can efficiently be inactivated while at the same the RNA is stabilized and is protected from degradation.

The RNA can be released from the sample in the presence or absence of an anion exchange matrix. Releasing the RNA and binding the RNA to the anion exchange matrix can occur simultaneously.

The method comprises binding the RNA to the anion exchange matrix. If the method comprises releasing the RNA from the sample, the RNA can be bound to the anion exchange matrix subsequently to or simultaneous with releasing the RNA. According to one embodiment, the RNA is bound to the anion exchange matrix after releasing the RNA from the sample.

Exemplary and preferred anion exchange matrices for binding the RNA have been described above and it is referred to this description. In particular, the anion exchange matrix can be provided by particles, such as magnetic particles, comprising or coated with an anion exchange surface. Exemplary anion exchange surfaces and anion exchange groups have also been described above and are referred to.

According to one embodiment, binding the RNA to an anion exchange matrix comprises preparing a binding mixture from the sample that contains the released RNA. The binding mixture comprises an anion exchange matrix such as anion exchange particles for binding the RNA. The term "binding mixture" as used herein refers to the composition that is prepared for the RNA binding step and which allows to bind RNA comprised in the sample to the anion exchange matrix. By preparing the binding mixture, conditions are established so that RNA comprised in the binding mixture binds to the anion exchange matrix. Suitable conditions to achieve RNA binding to an anion exchange surface are well-known to the skilled person.

The binding mixture has a pH that allows binding of the RNA to the anion exchange surface of the particles. The pH that is suitable for binding in particular depends on the nature of the anion exchange groups. Suitable pH values for the binding pH can be determined by the skilled person. The binding mixture may have a pH selected from $\leq 8$, $\leq 7.5$, $\leq 7$, $\leq 6.5$, $\leq 6.25$ and $\leq 6$. According to one embodiment, the binding pH is in the range of from 3 to $\leq 8$, more preferably is in a range selected from 3.5 to 7.5; 3.75 to 7; 4 to 6.5 and 4.25 to 6 and 4.5 to 5.75.

The binding mixture may comprise a salt. Incorporating a salt into the binding mixture improves the isolation results. According to one embodiment, the salt is an alkali metal salt. The alkali metal salt is according to one embodiment an alkali metal halide. Suitable examples include sodium chloride, potassium chloride and lithium chloride, wherein sodium and potassium chloride being preferred. According to one embodiment, the binding mixture does not comprise a chaotropic salt such as guanidinium salts, iodides, thiocyanates, perchlorates or other chaotropic salts of equal or stronger chaotropic nature in a concentration of 500 mM or more, 200 mM or more or 100 mM or more. Preferably, the binding mixture lacks such chaotropic salt.

According to one embodiment, RNA is not exposed to or contacted with ammonium sulfate prior to or during binding RNA to the anion exchange matrix. According to one embodiment, the binding mixture does not comprise ammonium sulfate.

Once RNA is bound to the anion exchange matrix, the anion exchange matrix with the bound RNA can be separated from the remaining binding mixture. Suitable means for separation are known to the skilled person.

The bound RNA can optionally be washed by performing one or more washing steps after binding the RNA. According to one embodiment, at least one washing solution, preferably a washing buffer, is contacted with the anion exchange matrix, such as the particles, to which the RNA is bound. In order to ensure maximum recovery of the bound RNA, the washing conditions should be chosen such that no significant amount of RNA bound to the anion exchange matrix is removed therefrom during washing.

Washing is particularly recommended, if the isolated RNA is e.g. supposed to be directly analysed and/or detected e.g. in a diagnostic assay without further purification. If the isolated RNA is supposed to be directly analysed using methods that are e.g. sensitive to potential impurities (such as e.g. PCR methods), it is recommended to perform at least two washing steps. According to one embodiment, preferably two different volumes of wash solutions are used. Here, the volume of the first washing solution is preferably larger than the volume of the second washing solution. Washing is, however, not necessary if subsequently a detection and/or analysis method is used that is rather insensitive to impurities.

The washing solution may contain a surfactant. Suitable surfactants include but are not limited to non-ionic surfactants, such as polyoxyethylene-based non-ionic surfactants, preferably selected from the group consisting of polyoxyethylene fatty alcohol ethers, polyoxyethylene alkylphenyl ethers, and polyoxyethylene-polyoxypropylene block copolymers. Preferred examples are TritonX-100 or Brij58, for example at a concentration of about 0.01%-1%.

Suitable washing solutions and buffers are also known in the prior art (see e.g. WO 2013/045432) and thus, do not need any further description here.

According to one embodiment, the washing solution or buffer does not comprise ammonium sulfate. According to one embodiment, the washing solution or buffer does not comprise diammonium sulfate.

The step of releasing the bound RNA from the anion exchange matrix at conditions comprising a temperature of at least 70° C. and a pH of at least 8, preferably a pH of at least 9, in the presence of ammonium sulfate (preferably at a concentration of 10 mM or less) has been described in detail above and it is referred to said description for the sake of conciseness. In particular, the treatment conditions suitable for releasing the RNA from the anion exchange matrix can be as described above. There, suitable and preferred ammoniums sulfate concentrations, pH values and temperatures were described in detail. As discussed, treatment to release the RNA can occur in the presence of a chelating agent, preferably EDTA. Details were described above and it is referred to the respective disclosure. According to one embodiment, the step of releasing the bound RNA from the anion exchange matrix occurs at conditions comprising a temperature of at least 70° C. and a pH of from 9.5 to 12.5, preferably 10 to 12 and in the presence of ammonium sulfate in a concentration of from 0.5 mM to 7 mM, preferably 0.75 mM to 5 mM. According to one embodiment, the step of releasing the bound RNA from the anion exchange matrix occurs at conditions comprising a temperature of at least 70° C. and a pH of from 10 to 12 and in the presence of ammonium sulfate in a concentration of from 0.5 mM to 5 mM, preferably 0.75 mM to 3 mM. As described above, the release may occur in the presence of a chelating agent, preferably EDTA. Thus, the step of releasing the bound RNA from the anion exchange matrix may occur at conditions comprising a temperature of at least 70° C. and a pH of from 9.5 to 12.5, preferably 10 to 12, in the presence of ammonium sulfate in a concentration of from 0.5 mM to 7 mM, preferably 0.75 mM to 5 mM and additionally in the presence of EDTA. In embodiments, EDTA is present in a concentration of from 0.005 mM to 1 mM, preferably 0.01 mM to 0.5 mM. According to one embodiment, EDTA is present in a concentration of from 0.005 mM to 0.015 mM. The treatment temperature is in embodiments in a range of 70° C. to 90° C., 72° C. to 88° C. or 75° C. to 85° C.

As described above, the anion exchange matrix with the bound RNA is preferably contacted with an ammonium sulfate containing solution having one or more of the characteristics as described in detail above. It is referred to the above disclosure and the above described solutions can be used for releasing/eluting the RNA from the anion exchange matrix.

According to one embodiment, RNA is not exposed to or contacted with ammonium sulfate prior to releasing the RNA from the anion exchange matrix. According to one embodiment, RNA is not exposed to or contacted with diammonium sulfate prior to releasing the RNA from the anion exchange matrix.

The released RNA can be further analyzed and/or detected. RNA is efficiently stabilized with the method according to the invention by ammonium sulfate thereby reducing degradation effects that otherwise occur when using treatment conditions at a temperature of at least 70° C. and a pH of at least 8, preferably a pH of at least 9. As can be seen from the examples, this effect was observed even for a very low ammonium sulfate concentration of 10 mM or less, such as about 2.5 mM. Advantageously, the used ammonium sulfate concentrations can be very low and such low concentrations do not interfere even with sensitive applications. Also, because ammonium sulfate exerts even at such low concentrations a strong stabilizing effect on the RNA, it is also possible to efficiently inactivate enzymes that otherwise could interfere with downstream applications. Hence, the present method yields RNA with excellent quality that is suitable also for highly sensitive and quantitative detection, such as for example in qPCR-based detection of viral RNA (e.g., HCV, HIV) in diagnostics assays.

The isolated RNA can be analysed and/or detected using suitable assay and/or analytical methods. Hence, according to one embodiment, the released or isolated RNA is analysed and or detected. The analysis can be performed in order to identify, detect, screen for, monitor or exclude a disease, an infection and/or at least one fetal characteristic.

An eluate comprising the released or isolated RNA can optionally be neutralized, e.g. if a respective neutral pH value is beneficial for the intended downstream applications.

The isolated RNA and/or a specific target RNA comprised or suspected of being comprised in the isolated RNA can be identified, quantified, modified, contacted with at least one enzyme, amplified, reverse transcribed, cloned, sequenced, contacted with a probe and/or be detected. Respective methods are well-known in the prior art and are commonly applied in the medical, diagnostic and/or prognostic field in order to analyse RNA, such as total RNA or extracellular RNA.

The analysis/further processing of the RNA can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

Exemplary and preferred methods are further described below.

Provided is a method of isolating RNA from a sample, the method comprising:

optionally releasing the RNA from the sample;

binding the RNA to an anion exchange matrix;

optionally washing the bound RNA;

treating the RNA at conditions comprising a temperature of at least 70° C. and a pH of from 9.5 to 12.5, preferably 10 to 12, in the presence of ammonium sulfate at a concentration of 10 mM or less to release the RNA from the anion exchange matrix.

Provided is a method of isolating RNA from a sample, the method comprising:

optionally releasing the RNA from the sample;

binding the RNA to an anion exchange matrix;

optionally washing the bound RNA;

treating the RNA at conditions comprising a temperature of at least 70° C. and a pH of from 9.5 to 12.5, preferably 10 to 12, in the presence of ammonium sulfate at a concentration of from 0.5 mM to 7 mM, preferably 0.75 mM to 5 mM to release the RNA from the anion exchange matrix.

Provided is a method of isolating RNA from a sample, the method comprising:

optionally releasing the RNA from the sample;

binding the RNA to an anion exchange matrix;

optionally washing the bound RNA;

treating the RNA at conditions comprising a temperature of at least 70° C. and a pH of from 10 to 12 in the presence of ammonium sulfate at a concentration of from 0.5 mM to 5 mM, preferably 0.75 mM to 3 mM to release the RNA from the anion exchange matrix.

As described above, treatment may occur in the presence of a chelating agent, preferably EDTA. In embodiments, EDTA Is present in a concentration of from 0.005 mM to 1 mM, preferably 0.01 mM to 0.5 mM. EDTA can be present in a concentration of from 0.005 mM to 0.015 mM. The treatment temperature is in embodiments in a range of 70° C. to 90° C., 72° C. to 88° C. or 75° C. to 85° C.

Provided is a method of isolating RNA from a sample, the method comprising:

optionally releasing the RNA from the sample;

binding the RNA to an anion exchange matrix;

optionally washing the bound RNA;

releasing the bound RNA from the anion exchange matrix by contacting the bound RNA with a solution comprising ammonium sulfate and having a pH of at least 8, preferably a pH of at least 9, and treatment at a temperature of at least 70° C., wherein the temperature is adjusted to at least 70° C. prior to or after contacting the RNA with the solution.

As discussed above, the RNA can be incubated in the solution; details were described above. Suitable and preferred ammonium sulfate containing solutions that can be used to release the bound RNA were also described in detail above and it is referred to the above disclosure. The anion exchange matrix is in an embodiment provided by particles, preferably magnetic particles. The use of particles such as magnetic particle allows to conveniently provide for a temperature of 70° C. after the RNA has been contacted with the solution. However, it is also possible to use a solution pre-heated to at least 70° C. and to contact the bound RNA with such a pre-heated solution instead of adjusting the temperature to 70° C. only after the RNA has been contacted with the solution. Adjusting the temperature of the solution to at least 70° C. prior to contacting the RNA with the solution is preferable e.g. if the RNA is bound to an anion exchange matrix provided in form of a resin or column. Providing a pre-heated solution is convenient in this case, because this way, heating the resin or column which may be inconvenient or difficult due to the format and/or material of the column used is not required.

The eluted RNA is preferably separated from the anion exchange matrix.

Furthermore, the method of isolating RNA from a sample according to the present invention can also be used as a pre-treatment protocol for isolating and thus concentrating RNA from a sample for a subsequent purification protocol. This has the advantage that the RNA can be concentrated from a large sample volume to a small sample volume. It allows the use of subsequent standard nucleic acid isolation, respectively purification protocols that can be run e.g. on established automated systems which have limitations with respect to the sample volume they can handle. Time and costs can be saved and the yield of RNA can be increased because larger initial sample volumes can be processed.

Thus, a method of isolating RNA from a sample is provided, the method comprising:

optionally releasing the RNA from the sample;

binding the RNA to an anion exchange matrix;

optionally washing the bound RNA;

treating the RNA at conditions comprising a temperature of at least 70° C. and a pH of at least 8, preferably a pH of at least 9, in the presence of ammonium sulfate, in particular in the presence of ammonium sulfate at a concentration of 10 mM or less, to elute the RNA from the anion exchange matrix;

isolating the RNA from the eluate.

Details with respect to the optional releasing, the binding, the optional washing and the treating of the RNA to release/elute the RNA are disclosed above and it is referred to the above disclosure. Accordingly, the anion exchange matrix can in particular be provided by particles, such as magnetic particles, that provide an anion exchange surface, or can be comprised in a column. According to a preferred embodiment, a chelating agent such as EDTA is additionally present when treating the RNA. Particular preferred concentrations of chelating agents such as EDTA are provided above and apply. Enzymes, such as proteases, in particular proteinase K, and/or nucleases, in particular RNAses, advantageously can be denatured and hence inactivated if present when treating the RNA at conditions comprising a temperature of at least 70° C. and a pH of at least 8, preferably a pH of at least 9, in the presence of ammonium sulfate (preferably at a concentration of 10 mM or less) to elute the RNA from the anion exchange matrix. Inactivating nucleases such as RNAses that may be present when treating the RNA advantageously contributes to maintaining RNA integrity. Likewise, inactivating proteases and other enzymes that may be present has the advantageous effect that the inactivated enzymes do not exhibit undesirable enzymatic activity in downstream applications such as e.g. PCR.

Basically any standard nucleic acid isolation or purification protocol can be used subsequently to further isolate or purify the RNA from the eluate that was concentrated using the method of isolating RNA from a sample according to the present invention as a pre-treatment protocol. Examples for respective isolation or purification methods that can be used to isolate the RNA from the eluate include but are not limited to extraction, solid-phase extraction, polysilicic acid-based purification, magnetic particle-based purification, phenol-chloroform extraction, anion-exchange chromatography (using anion-exchange surfaces), electrophoresis, precipitation and combinations thereof. Also any other nucleic acid isolating technique known by the skilled person can be used. According to one embodiment, the RNA, such as in particular extracellular RNA, is isolated and hence further purified from the eluate using at least one chaotropic agent and/or at least one alcohol. Preferably, the RNA is isolated by binding it to a solid phase, preferably a solid phase comprising silicon, preferably polysilicic acid.

The pretreatment protocol can be performed manually or in an automated manner. Likewise, the isolation from the eluate can be performed manually or in an automated manner, in particular in a robotic system. According to one embodiment, the pretreatment protocol is performed manually and the isolation from the eluate is performed in an automated manner.

When using the present method as a pre-treatment protocol in order to concentrate RNA, the sample can be a sample as described herein, in particular a liquid and/or biological sample. The samples can be body fluids and samples derived from body fluids, in particular samples that are derived from body fluids by removing cells from the body fluids. The sample in particular can be selected from blood, plasma or serum and urine. The sample can be a liquid biopsy sample and/or a sample of or derived from liquid biopsy testings. Concentrating RNA from a large sample volume to a small sample volume with the present pre-treatment protocol is in particular desirable if the sample comprises RNA at low concentrations.

The RNA can in particular be extracellular RNA, in particular from a liquid and/or biological sample. Accordingly, in one embodiment a method of isolating extracellular RNA from a sample which is or is derived from a body fluid, preferably selected from blood, plasma, serum, and urine is provided, the method comprising:

optionally releasing the extracellular RNA from the sample;

binding the extracellular RNA to an anion exchange matrix;

optionally washing the bound extracellular RNA;

treating the extracellular RNA at conditions comprising a temperature of at least 70° C. and a pH of at least 8, preferably a pH of at least 9, in the presence of ammonium sulfate (preferably ammonium sulfate at a concentration of 10 mM or less) to elute the extracellular RNA from the anion exchange matrix;

isolating the extracellular RNA from the eluate.

It is also within the scope of the present invention to specifically isolate specific target extracellular RNA from the obtained enriched extracellular RNA, e.g. by using appropriate probes that enable a sequence specific binding and are coupled to a solid support.

As was also explained above, in embodiments DNA in addition to RNA is released/eluted, from the anion exchange matrix. Thus, the present method can also be used as a pre-treatment protocol in order to concentrate RNA, in particular extracellular RNA, and further to concentrate DNA, in particular extracellular DNA, from a large sample volume to a smaller sample volume. It is then possible to also isolate DNA from the eluate by basically any standard nucleic acid isolation or purification protocol, such as the protocols referred to above.

Nucleic acids, in particular RNA, isolated from the eluate, can then be further analyzed, detected and/or processed as was described above.

RNA and Samples

The type of RNA that can be processed or stabilized according to the present invention is not particularly limited. The RNA can be or can comprise prokaryotic or eukaryotic RNA, preferably mammalian RNA, more preferably human RNA. It can be or comprise fungal RNA. It can be or comprise pathogen and/or viral RNA (e.g. HCV, or HIV RNA).

The RNA can be total RNA. Advantageously, the present invention allows to protect total RNA including RNA of large size from degradation. The stabilizing properties of ammonium sulfate were discussed in detail above. The RNA can be or can comprise messenger RNA (mRNA), ribosomal RNA (rRNA), transfer RNA (tRNA) or other types of RNA. The RNA may comprise small RNA, such as small RNAs shorter than 300 nucleotides, in particular shorter than 100 nucleotides. Examples of small RNAs include micro RNAs (miRNAs), small interfering RNAs (siRNAs), small nuclear RNAs (snRNAs) and small nucleolar RNAs (snoRNAs). The RNA can be or comprise extracellular RNA. The term "extracellular RNA" as used herein in particular refers to RNA that is not contained in cells. Respective extracellular RNA is also often referred to as cell-free RNA. Hence, extracellular RNA usually is present exterior of a cell or exterior of a plurality of cells within a sample, preferably a biological sample. Extracellular RNA can be e.g. present in exosomes. Preferably, when the RNA is an extracellular RNA, the sample is not an artificial sample with synthetically produced RNA but is obtained from a biological source. Examples of extracellular RNA comprise extracellular tumor-associated or tumor-derived RNA, other extracellular disease-related RNA, fetal RNA, small interfering RNA such as e.g. miRNA and siRNA, and non-mammalian RNA, such as non-mammalian extracellular RNA, such as e.g. viral RNA, pathogenic RNA released e.g. from prokaryotes (e.g. bacteria), viruses or fungi.

The processed RNA can be derived from or can be isolated from a sample, such as an artificial sample or in particular a biological sample, wherein a biological sample is a sample obtained from a biological source. Biological samples usually have a complex composition and comprise many different components. The biological sample can be derived from prokaryotes as well as from eukaryotes. The biological sample can be a cell containing sample such as a tissue sample. It can also be selected from the group consisting of body fluids, whole blood, plasma, serum, sputum, lachrymal fluid, lymphatic fluid, synovial fluid, pleural effusion, urine, sweat, liquor, cerebrospinal fluid, ascites, milk, stool, bronchial lavage, saliva, amniotic fluid, nasal secretions, vaginal secretions, a surface biopsy, sperm, semen/seminal fluid, wound secretions and excretions, and cell culture supernatants and supernatants obtained from other swab samples. According to one embodiment, the sample is a liquid biopsy sample and/or a sample of or derived from liquid biopsy testings. According to one embodiment, the sample is a body fluid, a body secretion or body excretion. According to one embodiment, the sample is whole blood, plasma or serum. Other examples of RNA containing samples include but are not limited to biological samples such as cell suspensions, cell cultures, supernatant of cell cultures and the like. A biological sample in particular is a natural sample, e.g. obtained from a human or animal or derived from cell culture. Cells may have been removed from the original sample. Respective cell-depleted or cell-free samples are also encompassed by the term biological sample and also by the term natural sample. Typical examples of respective natural samples are body fluids such as blood and samples derived from a body fluid, in particular samples that derive from a body fluid by removing cells from the body fluid.

According to one embodiment, the sample is a liquid sample.

According to one embodiment, the sample is a sample that has not been contacted with ammonium sulfate for precipitating protein. According to one embodiment, the sample is a sample that has not been contacted with or stored in a solution comprising ammonium sulfate. According to one embodiment, the sample is a sample that has not been contacted with ammonium sulfate prior to performing a method according to the present invention. According to one embodiment, ammonium sulfate is not part of the RNA containing sample. According to one embodiment, ammonium salt is only added when putting the present invention into practice, preferably by adding the ammonium sulfate containing solution. Accordingly and as has been explained above, e.g. a sample that "has not been contacted with ammonium sulfate" can be a sample that has not been contacted with diammonium sulfate, a sample that has not been contacted with ammonium bisulfate, or a sample that has not been contacted with both.

Further Methods

The detailed disclosure provided above when discussing the method of processing RNA according to the first aspect of the invention is referred to and fully applies also for the further methods disclosed herein that are based on the above method and findings. This includes in particular the disclosure regarding temperature, pH, ammonium sulfate concentrations, incubation conditions, steps, solutions and materials, all of which can also be applied to and used in the further methods discussed below. The ammonium sulfate comprising solution described in detail above can be used to establish the treatment conditions in said methods.

As has been explained above when discussing the method of processing RNA according to the first aspect, stabilizing RNA can comprise inhibiting or preventing RNA degradation. Stabilizing RNA can result in retained, or substantially retained, RNA integrity. Details were explained above.

Thus, the present invention also provides a method of inhibiting or preventing RNA degradation at conditions comprising a temperature of at least 70° C. and a pH of at least 8, preferably a pH of at least 9, by contacting the RNA with ammonium sulfate. Suitable concentrations and concentration ranges for ammonium sulfate were described above. The ammonium sulfate is preferably present in a concentration of 10 mM or less in the reaction mixture.

Also provided is a method of retaining RNA integrity at conditions comprising a temperature of at least 70° C. and a pH of at least 8, preferably a pH of at least 9, by contacting the RNA with ammonium sulfate. Suitable concentrations and concentration ranges for ammonium sulfate were described above. The ammonium sulfate is preferably present in a concentration of 10 mM or less in the reaction mixture.

Also provided herein is a method of releasing RNA bound to an anion exchange matrix from said matrix, the method comprising treating the RNA at conditions comprising a temperature of at least 70° C. and a pH of at least 8, preferably a pH of at least 9, in the presence of ammonium sulfate. This results in an elution of the bound RNA. Suitable concentrations and concentration ranges for ammonium sulfate were described above. The concentration is preferably 10 mM or less.

Further provided herein is a method of analyzing and/or detecting RNA, the method comprising isolating RNA from a sample by binding RNA to an anion exchange matrix and treating the RNA at conditions comprising a temperature of at least 70° C. and a pH of at least 8, preferably a pH of at least 9, in the presence of ammonium sulfate (preferably at a concentration of 10 mM or less) to release the RNA from the anion exchange matrix, and analyzing and/or detecting released RNA. The method can be used to detect or diagnose a disease or infection, such as a viral disease or infection.

Also provided herein is a method of inactivating an enzyme in the presence of RNA, the method comprising treating the enzyme in the presence of RNA at conditions comprising a temperature of at least 70° C. and a pH of at least 8, preferably a pH of at least 9, in the presence of ammonium sulfate, preferably at a concentration of 10 mM or less. The enzyme can be an enzyme as described above. It can be a nuclease such as a DNAse or RNAse, or a protease, in particular proteinase K. Treating can comprise incubating as described above. It can comprise incubating for at least 1 min, at least 2 min or at least 5 min, for 15 min or less, 12 min or less, or 10 min or less. The enzyme can be inactivated by heat, by alkaline pH or both. The enzyme can be inactivated by denaturation. The method of inactivating an enzyme in the presence of RNA can comprise treating the enzyme in the presence of RNA at conditions comprising a temperature of at least 70° C. and a pH of at least 8, preferably a pH of at least 9, in the presence of ammonium sulfate, wherein RNA is released from an anion exchange matrix to which the RNA is bound. Suitable concentrations and concentration ranges for ammonium sulfate were described above.

Uses

The detailed disclosure provided above when discussing the method of processing RNA according to the first aspect of the invention is referred to and fully applies also for the uses disclosed herein. Again, this includes in particular the disclosure regarding temperature, pH, ammonium sulfate concentrations, incubation conditions, steps, ammonium sulfate containing solutions and materials, all of which can also be applied to and used in the uses discussed below.

According to a further aspect, the invention provides for the use of ammonium sulfate (preferably at a concentration of 10 mM or less) for stabilizing RNA at conditions comprising a temperature of at least 70° C. and a pH of at least 8, preferably a pH of at least 9. Details were described above.

According to a further aspect, the invention provides for the use of a solution for releasing RNA from an anion exchange matrix, the solution having a temperature of at least 70° C. and a pH of at least 8, preferably a pH of at least 9, and the solution comprising ammonium sulfate (preferably at a concentration of 10 mM or less). Details were described above.

According to a further aspect, provided herein is the use of ammonium sulfate (preferably at a concentration of 10 mM or less) for processing RNA, wherein processing comprises treating the RNA at conditions comprising a temperature of at least 70° C. and a pH of at least 8, preferably a pH of at least 9. Details were described above.

According to a further aspect, provided herein is the use of ammonium sulfate (preferably at a concentration of 10 mM or less) when inactivating enzymes in the presence of RNA, wherein inactivating comprises treating the enzyme in the presence of RNA at conditions comprising a temperature of at least 70° C. and a pH of at least 8, preferably a pH of at least 9. Details were described above.

Compositions and Kits

The detailed disclosure provided above when discussing the method of processing RNA according to the first aspect of the invention is referred to and fully applies also for the compositions disclosed herein. This applies in particular to the ammonium sulfate concentrations, pH values and ranges as well as temperature values and ranges described above. As was explained above, ammonium sulfate in a preferred embodiment is diammonium sulfate, and this also applies in relation with the compositions and kits disclosed herein.

According to a further aspect, the invention provides an RNA containing composition, the composition comprising ammonium sulfate (preferably at a concentration of 10 mM or less) and having a temperature of at least 70° C. and a pH of at least 8, preferably a pH of at least 9. Such RNA containing composition can be provided in the methods according to the first aspect during the high temperature and high pH treatment conditions. Details were described above in conjunction with the treatment of the RNA in the presence of ammonium sulfate and it is referred to the above disclosure. Again, according to a preferred embodiment the ammonium sulfate is diammonium sulfate. According to one embodiment, the RNA and ammonium sulfate containing composition additionally comprises a chelating agent, preferably EDTA. Details were described above. The composition in particular can be or can comprise a solution as described above, however, comprising RNA. Suitable and preferred solutions have been described above and are referred to. The composition can further comprise an anion exchange matrix, such as a solid support comprising an anion exchange surface. The anion exchange matrix can be provided by magnetic particles coated with or comprising an anion exchange surface. The composition can be an RNA eluate. Details were described above and it is referred to the above disclosure.

Also provided herein according to a further aspect is a kit, the kit comprising an anion exchange matrix, preferably magnetic particles providing an anion exchange surface, and a solution for releasing RNA from an anion exchange matrix, the solution having a pH of at least 8, preferably a pH of at least 9, characterized in that the solution comprises ammonium sulfate, preferably at a concentration of 10 mM or less, with diammonium sulfate being preferred. The kit may comprise further components for processing or isolating RNA. It may in particular comprise a proteolytic enzyme such as proteinase K. Details, in particular regarding the solution and the anion exchange matrix, were described above when describing the method of processing RNA according to the first aspect of the invention and the solution used therein. It is referred to the above disclosure which also applies here in full. This invention is not limited by the exemplary methods, uses, compositions, kits and materials disclosed herein, and any methods, uses, compositions, kits and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification, the singular forms "a", "an" and "the" include plural aspects unless the context clearly dictates otherwise. Thus, for example, reference to "a protease" includes a single type of protease, as well as two or more proteases. Likewise, reference to "a" "salt", "additive", "buffer" and the like includes single entities and combinations of two or more of such entities. Reference to "the disclosure" and "the invention" and the like includes single or multiple aspects taught herein; and so forth. Aspects taught herein are encompassed by the term "invention".

As used in the subject specification, the term "about" can mean the indicated value±10%, in particular the term "about" can mean the indicated value±5%.

The term "solution" as used herein in particular refers to a liquid composition, preferably an aqueous composition, in particular to an aqueous composition having an alkaline pH. The solution can be a mixture. It may be a homogenous mixture of only one phase but it is also within the scope of the present invention that a solution comprises solid additives such as e.g. anion exchange matrices and/or precipitates. Thus, the solution can also be an inhomogeneous mixture.

According to one embodiment, subject matter described herein as comprising certain steps in the case of methods or as comprising certain ingredients in the case of compositions, solutions and/or buffers refers to subject matter consisting of the respective steps or ingredients. According to one embodiment, subject matter described herein as comprising certain steps refers to subject matter consisting of the respective steps and wherein the steps are performed in the order presented. It is preferred to select and combine preferred embodiments described herein and the specific subject-matter arising from a respective combination of preferred embodiments also belongs to the present disclosure.

The following examples are not intended to be limiting to the scope of the invention.

EXAMPLES

The present inventors found that unexpectedly, the presence of ammonium sulfate at low concentrations strongly stabilizes RNA at high temperatures in aqueous solution and under strongly alkaline conditions. RNA degradation is inhibited. Without wishing to be bound by theory, this may be attributable to an inhibition and slowing of the process of hydrolysis as can be seen from the following examples.

Example 1—RNA Degradation in Alkaline Solution at High Temperature (75° C.)

Human total RNA from tissue samples was obtained by purification using the RNeasy Mini Kit according to the kit handbook. The concentration of the extracted human total RNA was adjusted to 800 ng/µl. Then 1 µl of this RNA solution was mixed with 19 µl of an alkaline solution or buffer as described below.

The solutions or buffers used were: solution 1 (comprising 20 mM NaOH, ca. pH 12); solution 2 (comprising 20 mM NaOH, buffered to pH 11 with Tris-HCl); and solution 3 (comprising 20 mM NaOH, buffered to pH 10 with Tris-HCl).

A 2 µl aliquot was immediately removed and mixed with 3 µl of 100 mM sodium acetate, pH 5 to stop any RNA degradation and was used as reference. The remainder of the mixture was then incubated at 75° C. At certain time points, 2 µl were removed and mixed with 3 µl of 100 mM sodium acetate, pH 5, in order to stop any further degradation.

Aliquots were removed from the mixture and were mixed with sodium acetate after 1 min, 2 min, 3 min, 5 min, 7 min, and 10 min of incubation at 75° C. In addition, an aliquot was removed after 10 min of incubation at 75° C. and was then placed on the lab bench at 20-25° C. for additional 20 min (total incubation time 30 min). Also, an aliquot was removed after 10 min of incubation at 75° C. and was then placed on the lab bench at 20-25° C. for additional 50 min (total incubation time 60 min).

The incubation time course thus was:
+1 min|+2 min|+3 min|+5 min|+7 min|+10 min|+30 min|+60 min, wherein for the time points +30 min and +60 min, the RNA was incubated for 10 min at 75° C., followed with an incubation at room temperature for additional 20 min (total incubation time 30 min) or for additional 50 min (total incubation time 60 min).

After completion of the time course, the RNA degradation time point samples (1 µl each) were separated on an Agilent BioAnalyzer system, using the RNA Nano Chip and the RNA Nano Kit. RNA integrity was analysed for the different incubation times and the RNA integrity number (RIN) was determined. The RIN is an algorithm for assigning integrity values to RNA measurements. RIN values range from 10 (intact) to 1 (totally degraded). Typically, RNA having a RIN value of 5 is considered as suitable for RT-PCR applications, but higher RIN values may be desirable for more sensitive applications.

Figure 1B:
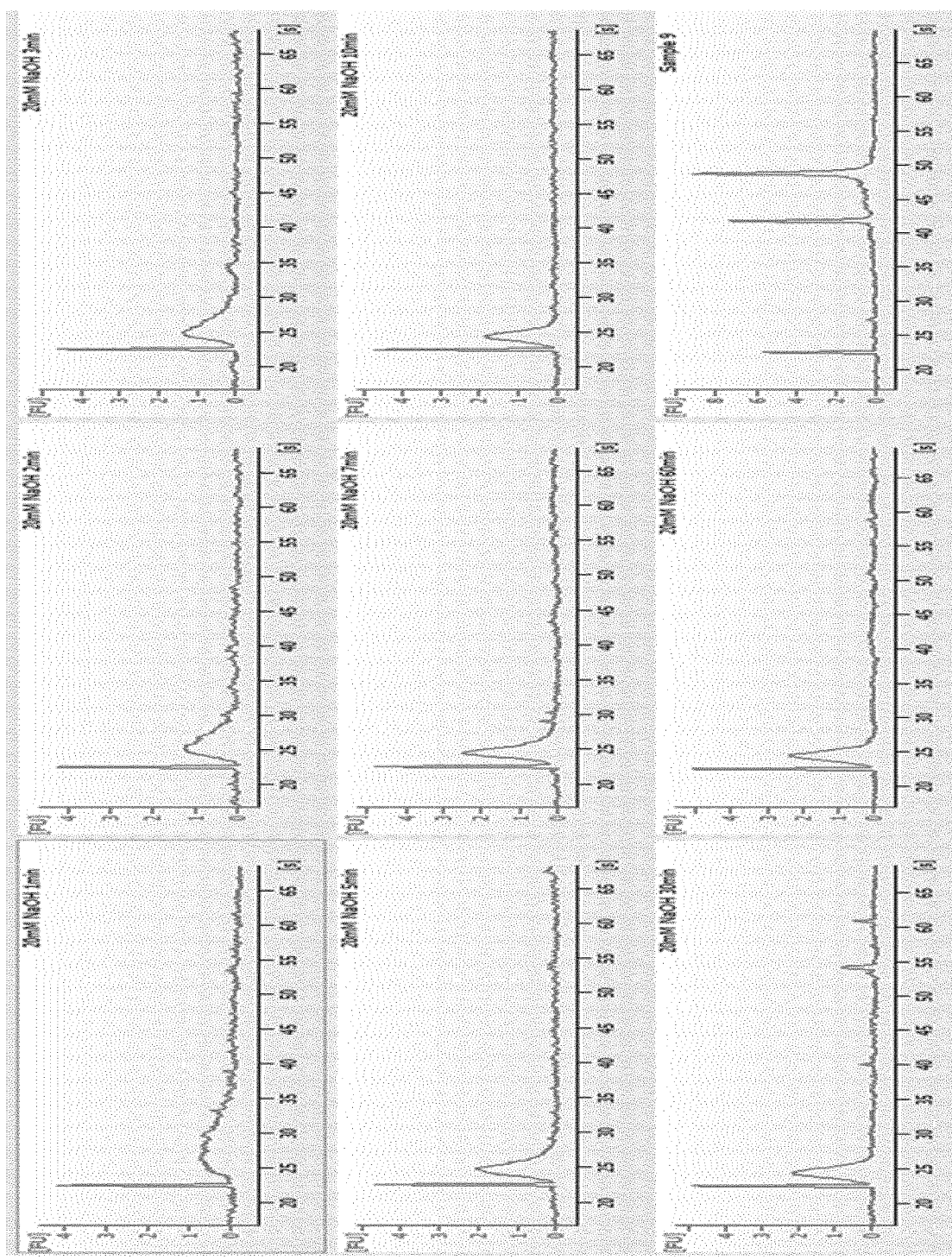
Figure 2A:
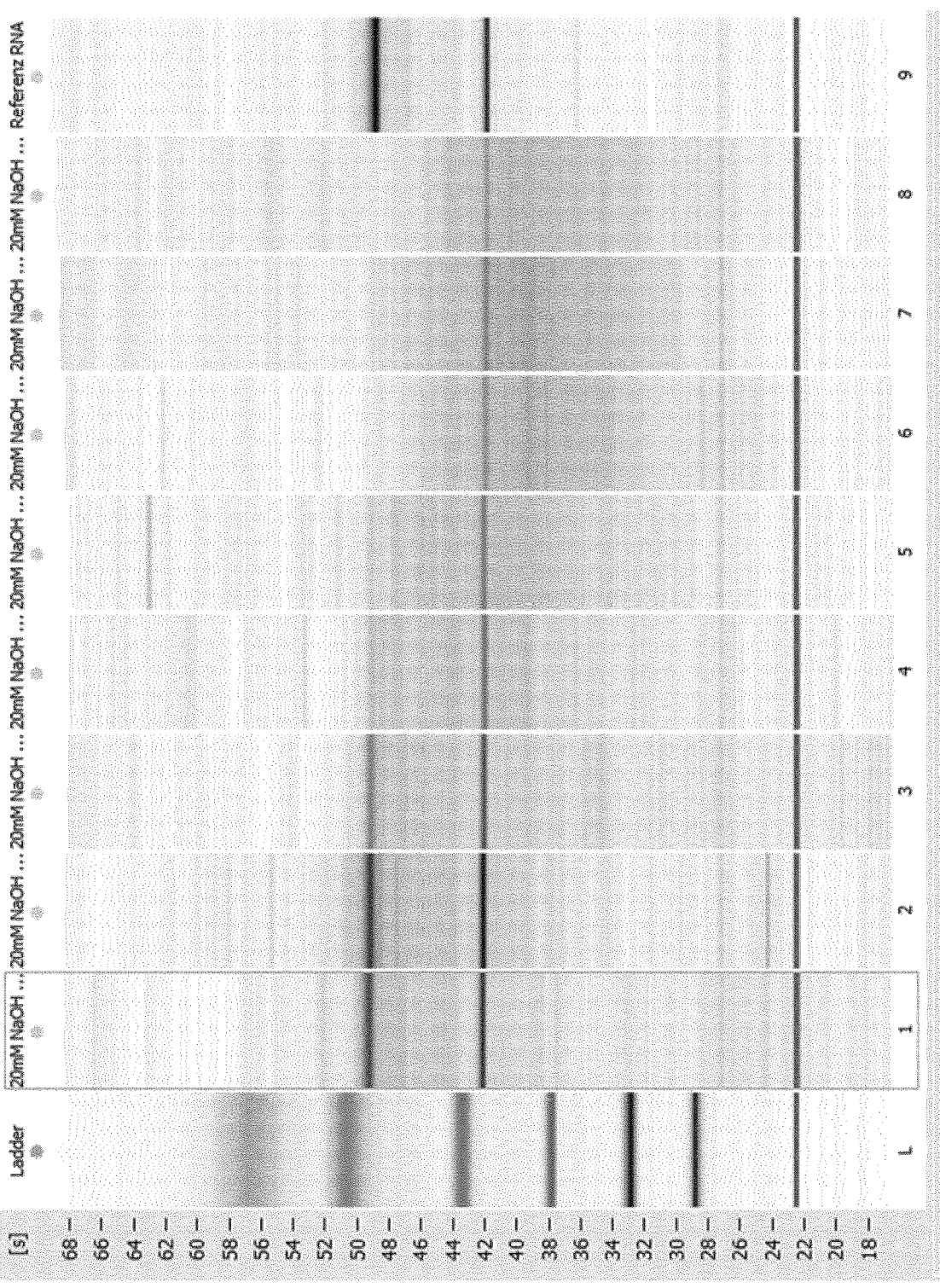
FIGS. 2A and 2B show Agilent BioAnalyzer images (gel-like image and electropherogram) of human total RNA incubated at 75° C. with solution 2, comprising 20 mM NaOH, buffered to pH 11 with Tris-HCl.
Figure 2B:
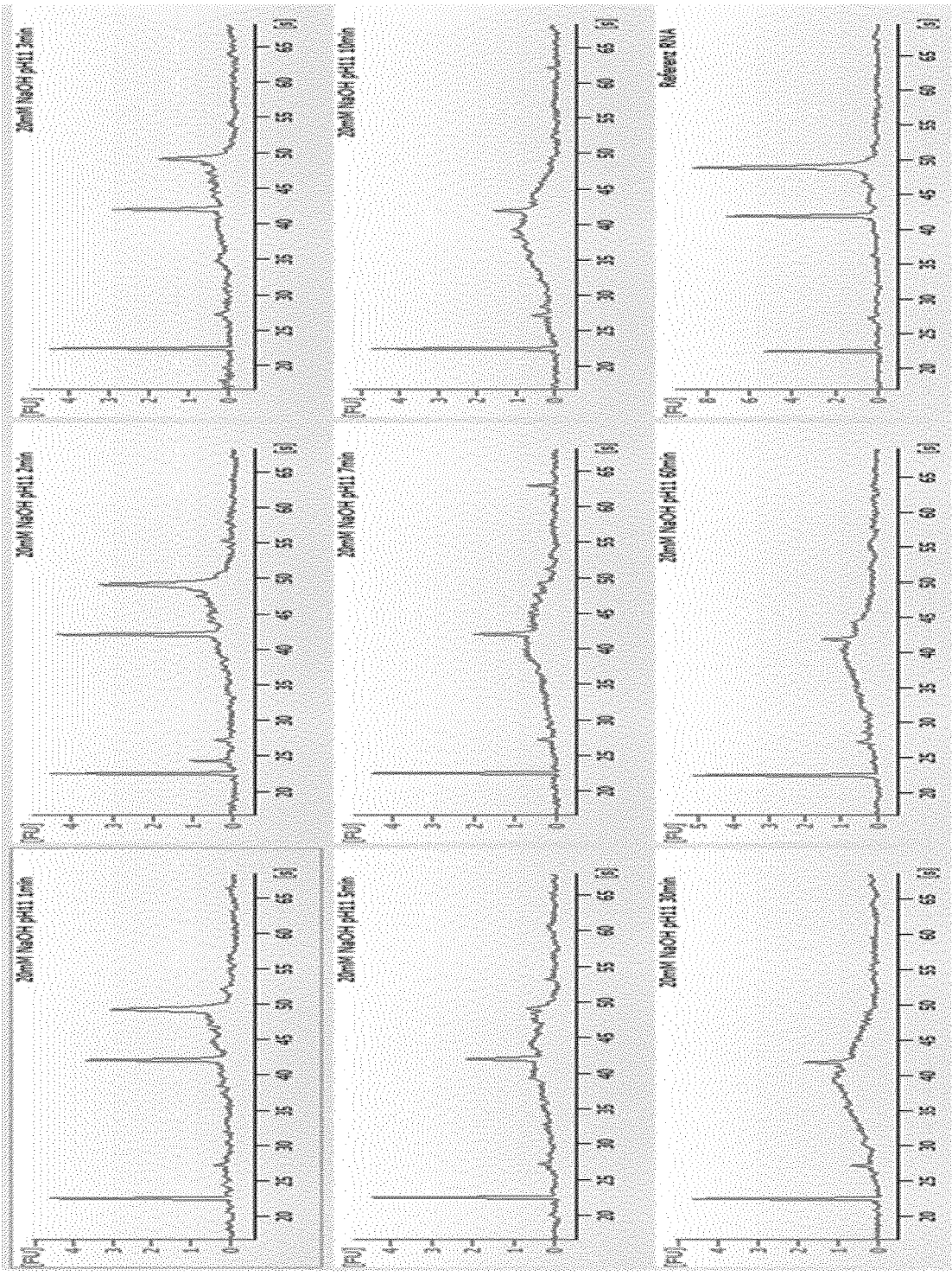
Figure 3A:
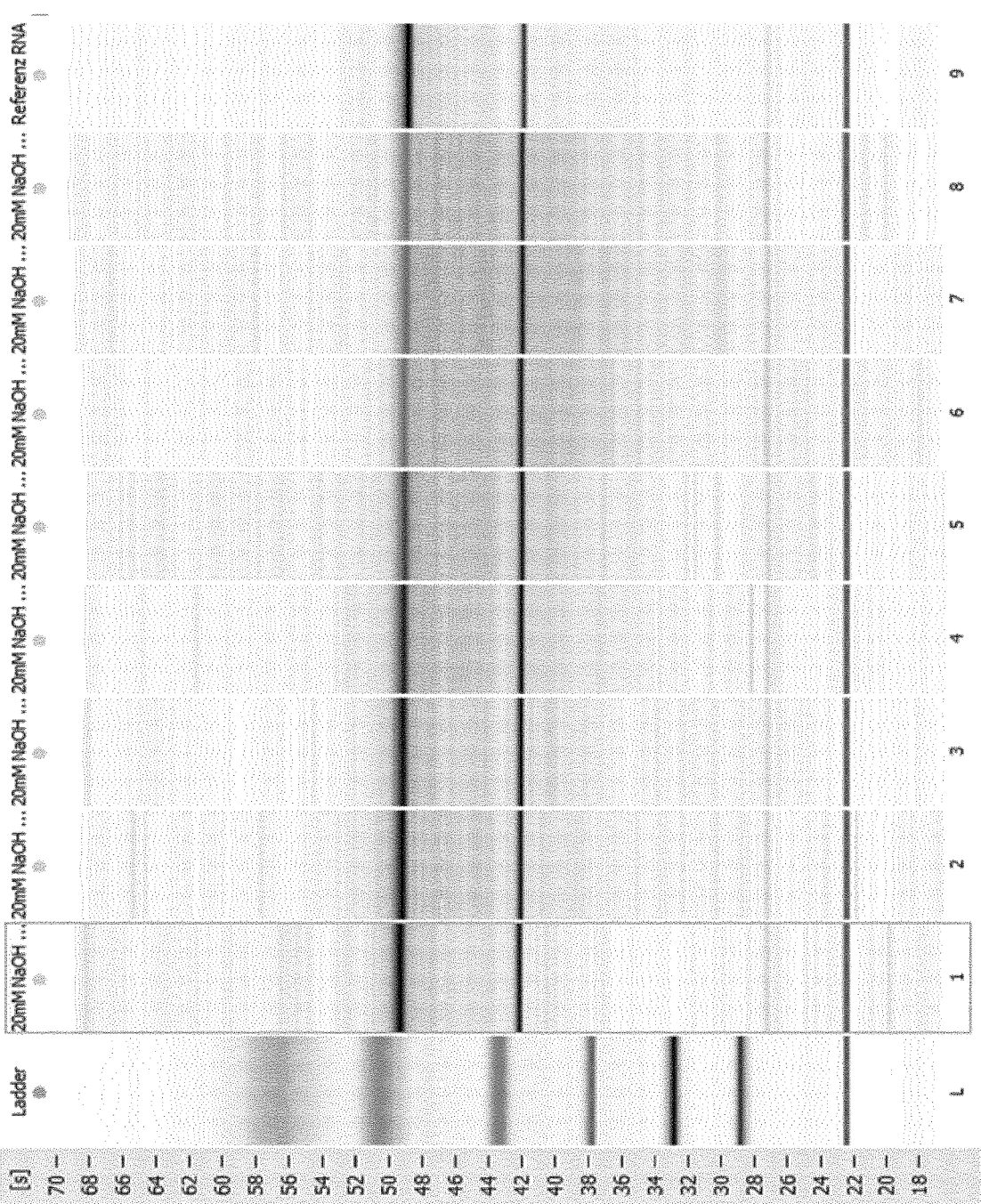
FIGS. 3A and 3B show Agilent BioAnalyzer images (gel-like image and electropherogram) of human total RNA incubated at 75° C. with solution 3, comprising 20 mM NaOH, buffered to pH 10 with Tris-HCl.
Figure 3B:
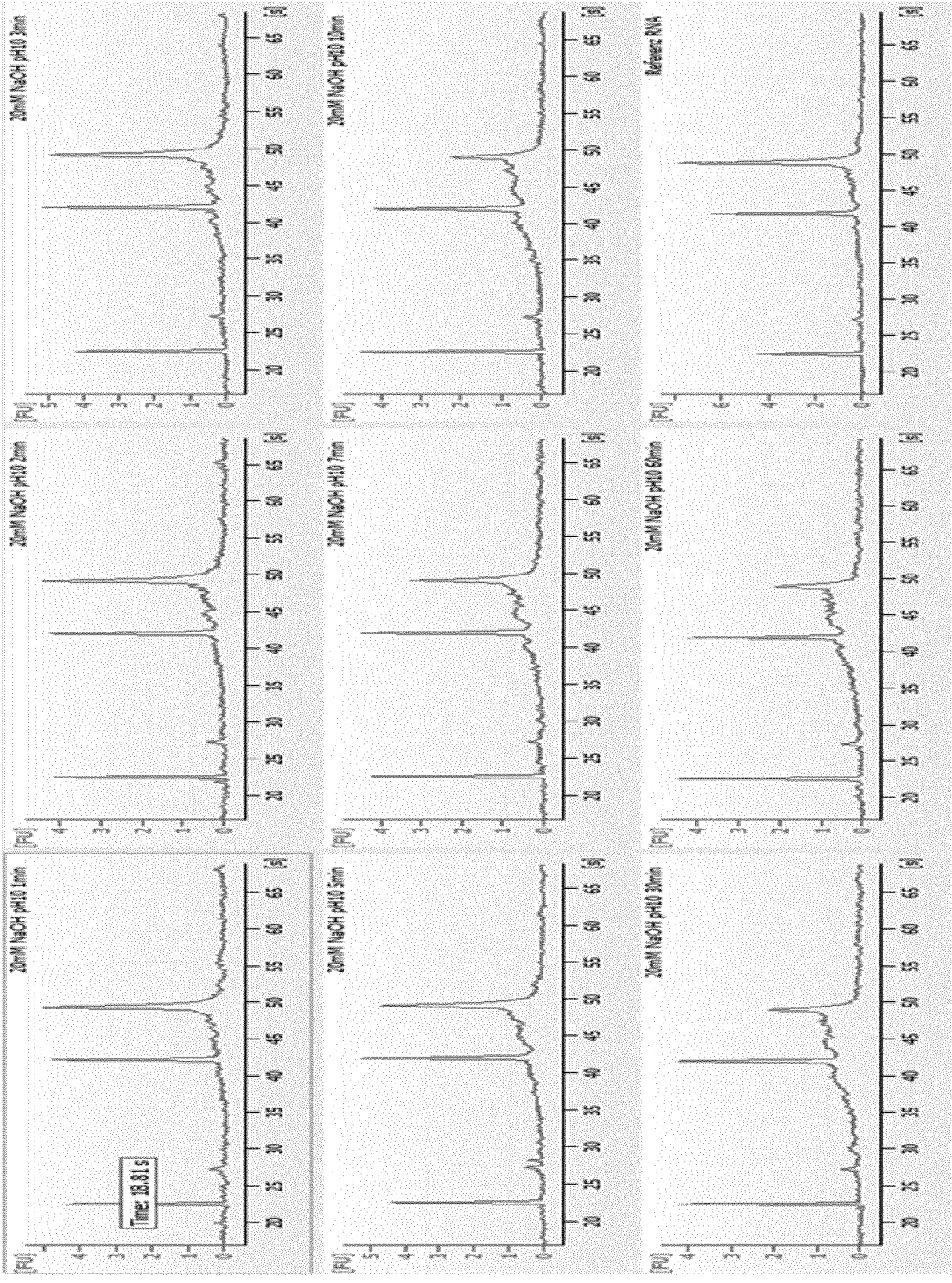

Results:

The results obtained for the solutions 1-3 are shown in FIGS. 1-3 and Tables 1-3 below and comprise the representation of results obtained with the Agilent BioAnalyzer system as gel-like images (FIGS. 1A, 2A, 3A), as electropherograms (FIGS. 1B, 2B and 3B), and in tabular format (Tables 1-3).

(a) Results for Solution 1

FIG. 1 shows Agilent BioAnalyzer images of human total RNA incubated at 75° C. with solution 1, comprising 20 mM NaOH, ca. pH 12. FIG. 1A shows a gel-like image. The y axis shows the size of the RNA, here expressed as time required to pass through the gel chip. A higher number indicates a larger molecular size. The figure shows the ladder (L) as well as samples 1-9, wherein the samples are as indicated below:

| | |
|---|---|
| Sample 1: 20 mM NaOH | 1 min |
| Sample 2: 20 mM NaOH | 2 min |
| Sample 3: 20 mM NaOH | 3 min |
| Sample 4: 20 mM NaOH | 5 min |
| Sample 5: 20 mM NaOH | 7 min |
| Sample 6: 20 mM NaOH | 10 min |
| Sample 7: 20 mM NaOH | 30 min |
| Sample 8: 20 mM NaOH | 60 min |
| Sample 9: Reference RNA | |

The 28S and 18S ribosomal RNAs are showing as distinct bands in the reference sample 9 and are indicated by arrows. As can be seen from the gel-like image, the 28S and 18S ribosomal RNAs are not readily detectable for samples 1-8, indicating that strong RNA degradation occurred. FIG. 1B shows the results in form of an electropherogram. The y axis shows the relative intensity of the fluorescence signal that is proportional to the RNA concentration at any given size. The x axis shows the relative RNA size as migration time through the gel chip (higher number=larger molecule size). Again, the 28S and 18S ribosomal RNAs are visible as distinct peaks in the reference sample 9 but are not readily detectable for samples 1-8, indicating that strong RNA degradation occurred in those samples.

Table 1 below also shows the degradation of RNA in samples 1-8. The degradation is indicated by low RIN values:

TABLE 1

| Sample Name | RIN Value |
|---|---|
| 20 mm NaOH 1 min | RIN: 1.90 |
| 20 mm NaOH 2 min | RIN: 2.30 |
| 20 mm NaOH 3 min | RIN: 2.40 |
| 20 mm NaOH 5 min | RIN: 2.60 |
| 20 mm NaOH 7 min | RIN: 2.60 |
| 20 mm NaOH 10 min | RIN: 2.50 |
| 20 mm NaOH 30 min | RIN: 2.70 |
| 20 mm NaOH 60 min | RIN: 2.60 |

(b) Results for Solution 2

FIG. 2 shows Agilent BioAnalyzer images of human total RNA incubated at 75° C. with solution 2, comprising 20 mM NaOH, buffered to pH 11 with Tris-HCl. FIG. 2A shows a gel-like image. The y axis shows the size of the RNA, here expressed as time required to pass through the gel chip. The figure shows the ladder (L) as well as samples 1-9, wherein the samples are as indicated below:

| | |
|---|---|
| Sample 1: pH 11 | 1 min |
| Sample 2: pH 11 | 2 min |
| Sample 3: pH 11 | 3 min |
| Sample 4: pH 11 | 5 min |
| Sample 5: pH 11 | 7 min |
| Sample 6: pH 11 | 10 min |
| Sample 7: pH 11 | 30 min |
| Sample 8: pH 11 | 60 min |
| Sample 9: Reference RNA | |

The 28S and 18S ribosomal RNAs are showing as distinct bands in the reference sample 9. Both, the 28S and 18S ribosomal RNA bands are visible also for samples 1-3, but there is a trend towards declining visibility (corresponding to increasing RNA degradation) with increasing incubation times. FIG. 2B shows the results in form of an electrophero-gram. The y axis shows the relative intensity of the fluorescence signal that is proportional to the RNA concentration at any given size. The x axis shows the relative RNA size as migration time through the gel chip (higher number=larger molecule size). Again, the 28S and 18S ribosomal RNAs are visible as distinct peaks in the reference sample 9. The corresponding peaks are also visible for samples 1-3, but there is a trend towards declining visibility for samples 1-8 with increasing incubation time. Samples 4-8 do not show the 28S peak.

Table 2 below shows the degradation of RNA by a declining trend of the RIN values. In particular, for incubation times of 5 min or higher, RIN values are below 5.

TABLE 2

| Sample Name | RIN Value |
|---|---|
| 20 mm NaOH pH 11 1 min | RIN: 7.50 |
| 20 mm NaOH pH 11 2 min | RIN: 7.50 |
| 20 mm NaOH pH 11 3 min | RIN: 6.60 |
| 20 mm NaOH pH 11 5 min | RIN: 4.90 |
| 20 mm NaOH pH 11 7 min | RIN: 4.30 |
| 20 mm NaOH pH 11 10 min | RIN: 3.60 |
| 20 mm NaOH pH 11 30 min | RIN: 3.80 |
| 20 mm NaOH pH 11 60 min | RIN: 3.80 |
| Reference RNA | RIN: 9 |

(c) Results for Solution 3

FIG. 3 shows Agilent BioAnalyzer images of human total RNA incubated at 75° C. with solution 3, comprising 20 mM NaOH, buffered to pH 10 with Tris-HCl. FIG. 3A shows a gel-like image. The y axis shows the size of the RNA, here expressed as time required to pass through the gel chip. The figure shows the ladder (L) as well as samples 1-9, wherein the samples are as indicated below:

| | |
|---|---|
| Sample 1: pH 10 | 1 min |
| Sample 2: pH 10 | 2 min |
| Sample 3: pH 10 | 3 min |
| Sample 4: pH 10 | 5 min |
| Sample 5: pH 10 | 7 min |
| Sample 6: pH 10 | 10 min |
| Sample 7: pH 10 | 30 min |
| Sample 8: pH 10 | 60 min |
| Sample 9: Reference RNA | |

As can be seen from the gel-like image, the 28S and 18S ribosomal RNAs are showing as distinct bands for all samples. Bands tend to get fainter for the 28S ribosomal RNAs with increasing incubation times.

FIG. 3B shows the results in form of an electropherogram. The y axis shows the relative intensity of the fluorescence signal that is proportional to the RNA concentration at any given size. The x axis shows the relative RNA size as migration time through the gel chip (higher number=larger molecule size). Again, the 28S and 18S ribosomal RNAs are showing as distinct peaks. Degradation of 28S RNA is visible by a decreasing peak height for increasing incubation times.

Table 3 below shows the degradation of RNA by a declining trend of the RIN values.

TABLE 3

| Sample Name | RIN Value |
|---|---|
| 20 mm NaOH pH 10 1 min | RIN: 9.30 |
| 20 mm NaOH pH 10 2 min | RIN: 8.20 |
| 20 mm NaOH pH 10 3 min | RIN: 8.20 |
| 20 mm NaOH pH 10 5 min | RIN: 7.60 |
| 20 mm NaOH pH 10 7 min | RIN: 7.60 |
| 20 mm NaOH pH 10 10 min | RIN: 6.50 |
| 20 mm NaOH pH 10 30 min | RIN: 6.10 |
| 20 mm NaOH pH 10 60 min | RIN: 6.60 |
| Reference RNA | RIN: 8.60 |

Example 2—RNA Degradation in Alkaline Solution at High Temperature (85° C.)

Experimental Setup:

Human total RNA from tissue samples was obtained by purification using the RNeasy Mini Kit according to the kit handbook. The concentration of the extracted human total RNA was adjusted to 800 ng/μl. Then 1 μl of this RNA solution was mixed with 19 μl of an alkaline solution or buffer as described below.

The solutions or buffers used were: solution 1 (comprising 20 mM NaOH, ca. pH 12); solution 2 (comprising 20 mM NaOH, buffered to pH 11 with Tris-HCl); and solution 3 (comprising 20 mM NaOH, buffered to pH 10 with Tris-HCl).

A 2 μl aliquot was immediately removed and mixed with 3 μl of 100 mM sodium acetate, pH 5 to stop any RNA degradation. The remainder of the mixture was then incubated at 85° C. At certain time points, 2 μl were removed and mixed with 3 μl of 100 mM sodium acetate, pH 5.

Aliquots were removed from the mixture and were mixed with sodium acetate after 1 min, 2 min, 3 min, 5 min, 7 min, and 10 min of incubation at 85° C. In addition, an aliquot was removed after 10 min of incubation at 85° C. and was then placed on the lab bench at 20-25° C. for additional 20 min (total incubation time 30 min). Also, an aliquot was removed after 10 min of incubation at 85° C. and was then placed on the lab bench at 20-25° C. for additional 50 min (total incubation time 60 min).

The incubation time course thus was:

+1 min|+2 min|+3 min|+5 min|+7 min|+10 min|+30 min|+60 min, wherein for the time points +30 min and +60 min, the RNA was incubated for 10 min at 85° C., followed with an incubation at room temperature for additional 20 min (total incubation time 30 min) or for additional 50 min (total incubation time 60 min).

After completion of the time course, the RNA degradation time point samples (1 μl each) were separated on an Agilent BioAnalyzer system, using the RNA Nano Chip and the RNA Nano Kit. RNA integrity (RIN value) was analysed versus incubation time.

Figure 4A:
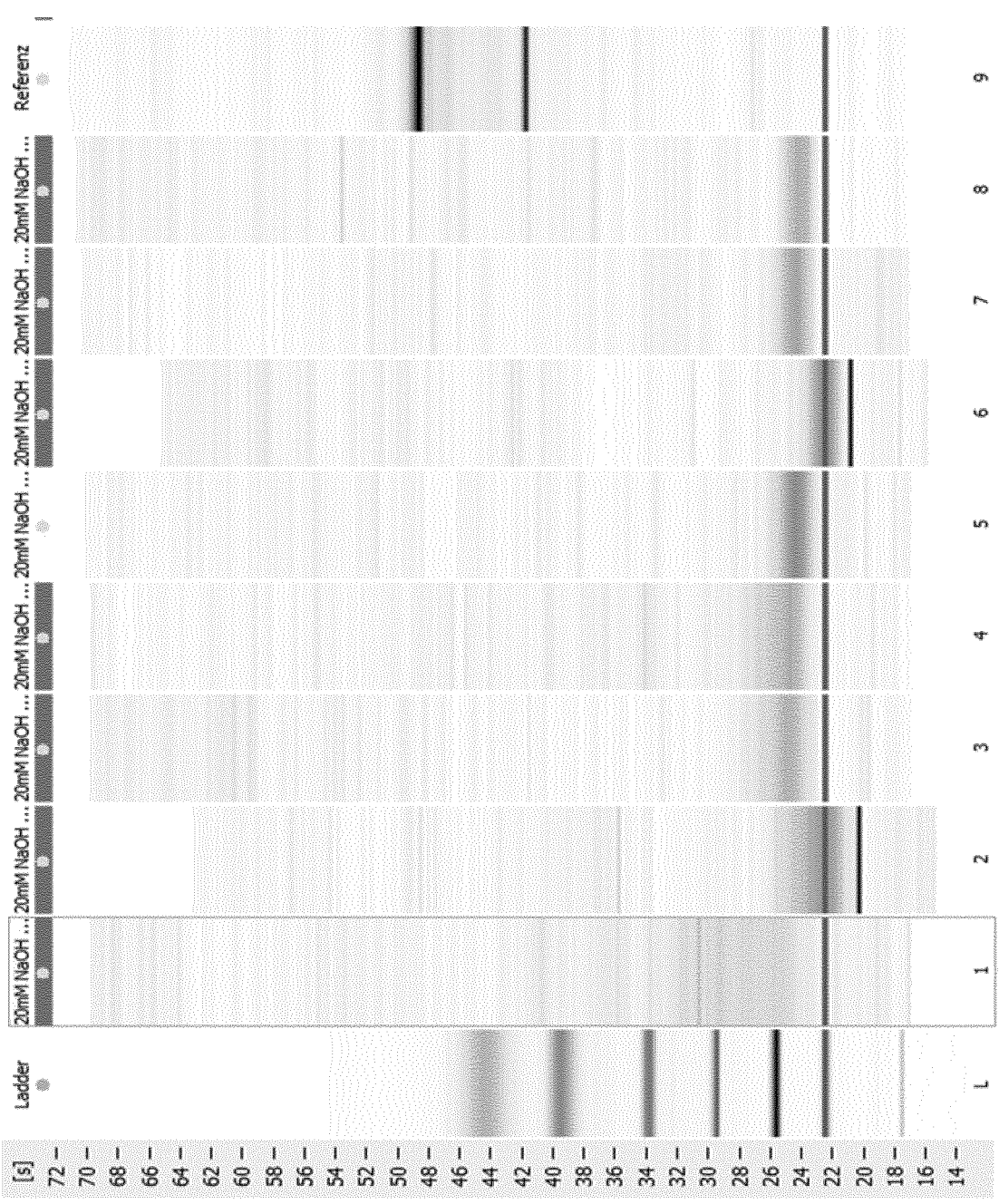
FIGS. 4A and 4B show Agilent BioAnalyzer images (gel-like image and electropherogram) of human total RNA incubated at 85° C. with solution 1, comprising 20 mM NaOH, ca. pH 12.
Figure 4B:
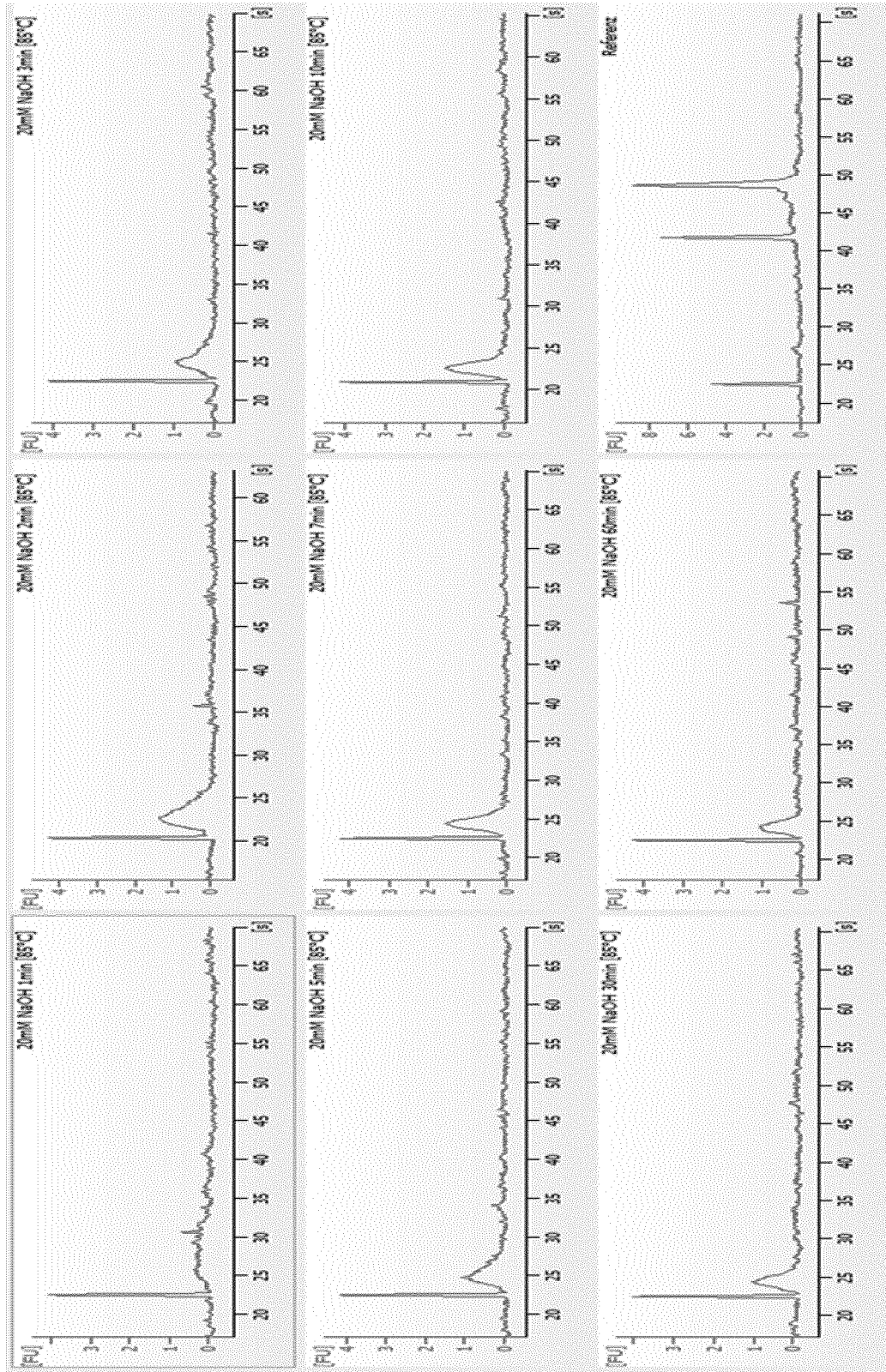
Figure 5A:
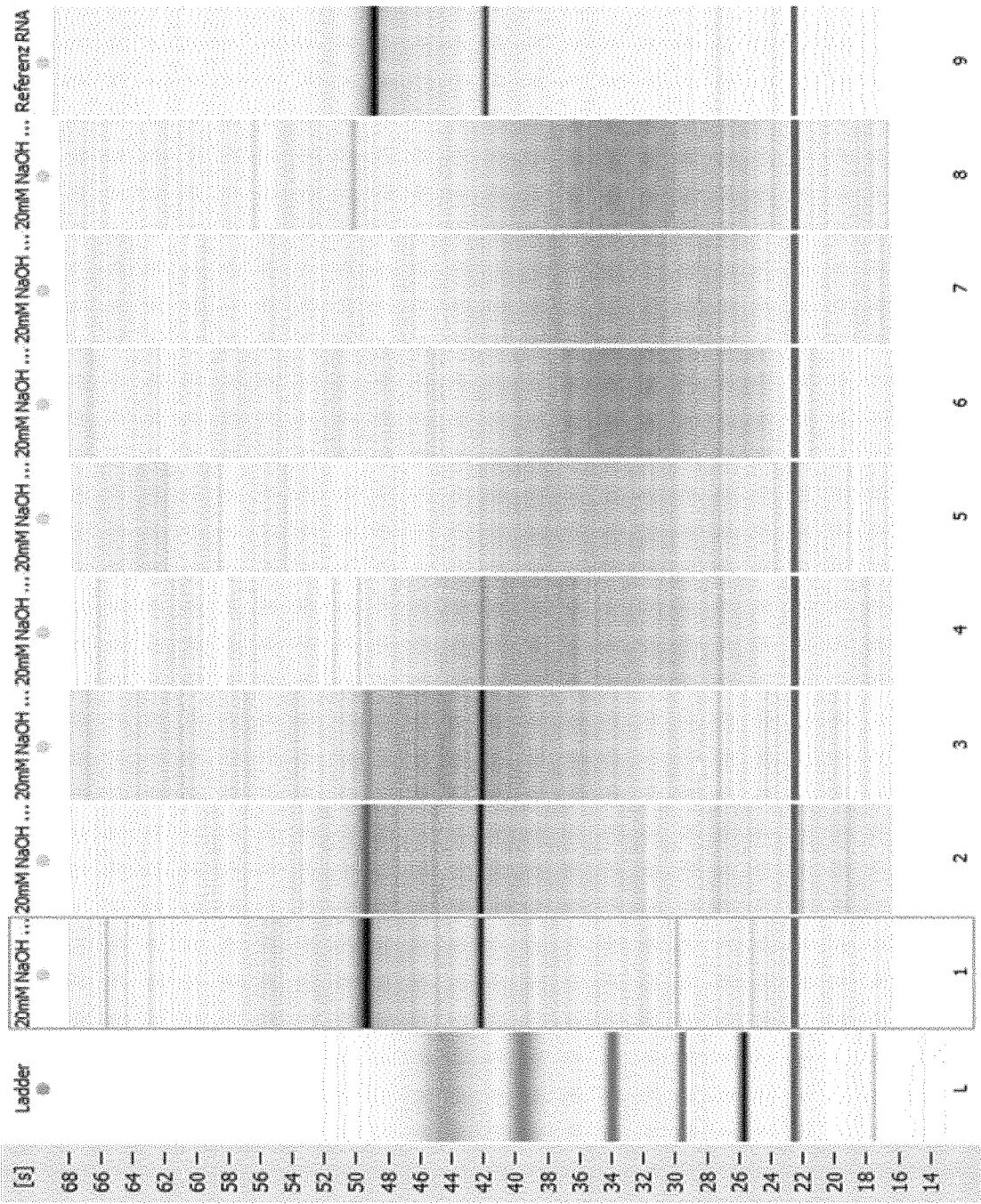
FIGS. 5A and 5B show Agilent BioAnalyzer images (gel-like image and electropherogram) of human total RNA incubated at 85° C. with solution 2, comprising 20 mM NaOH, buffered to pH 11 with Tris-HCl.
Figure 5B:
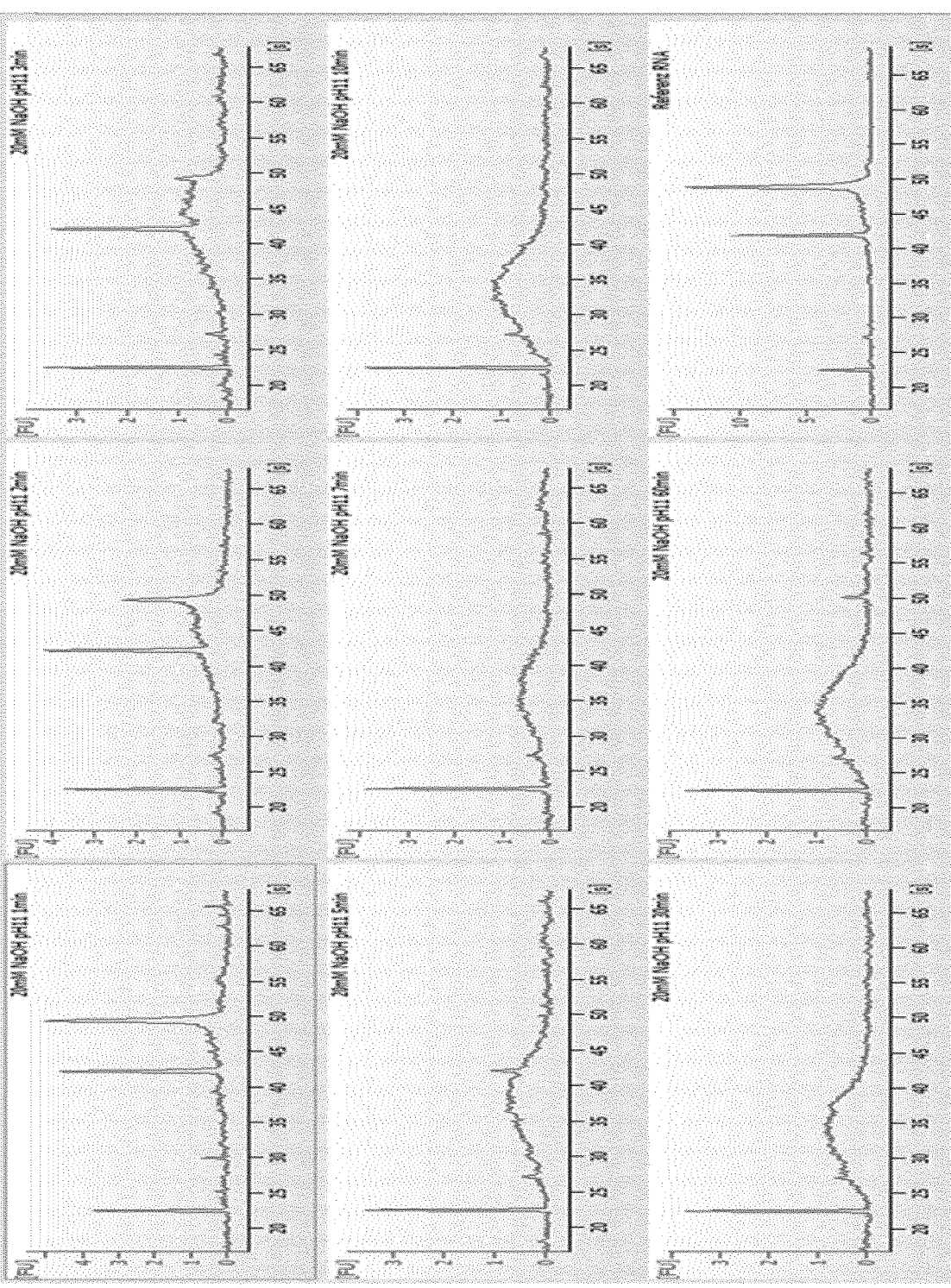
Figure 6A:
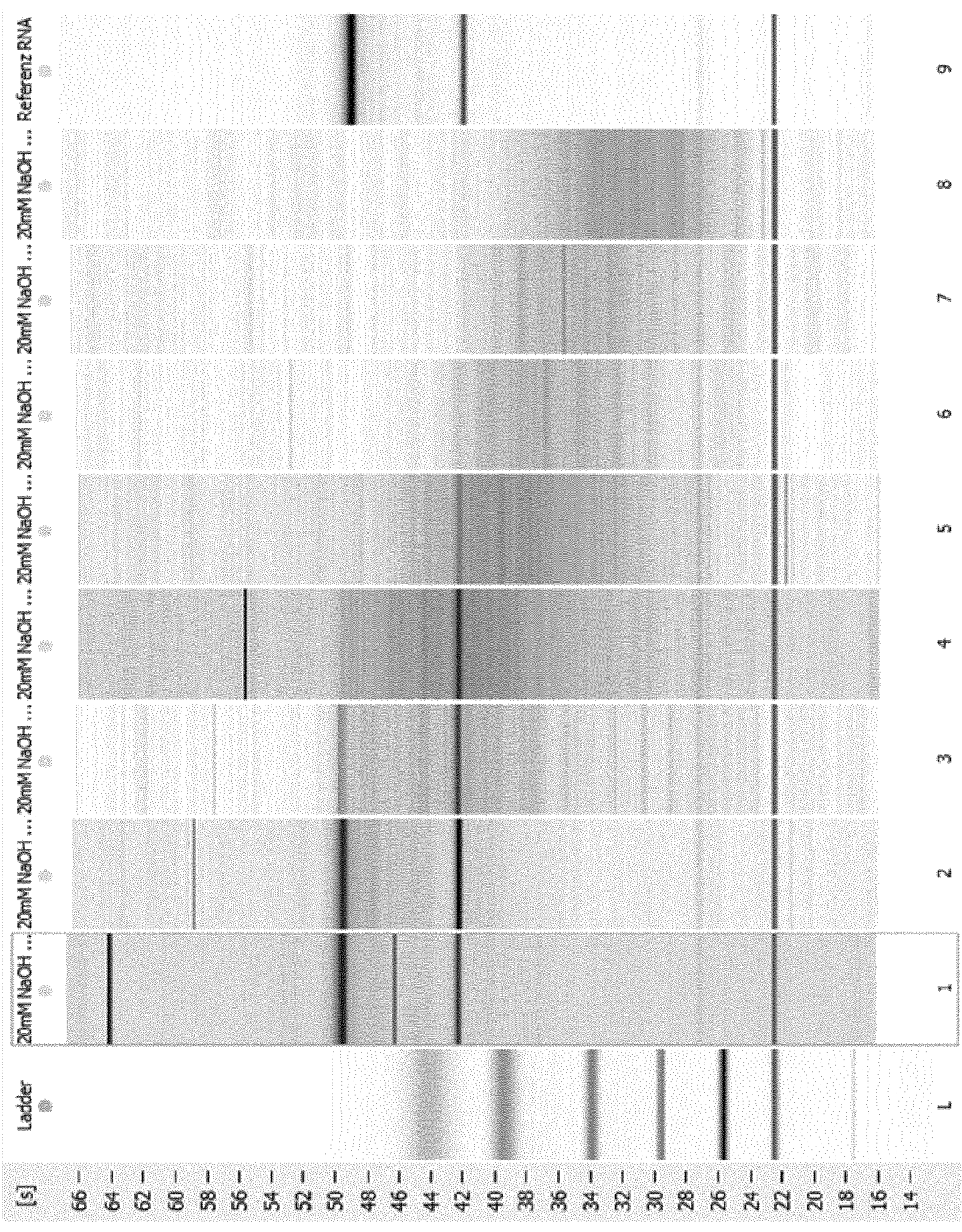
FIGS. 6A and 6B show Agilent BioAnalyzer images (gel-like image and electropherogram) of human total RNA incubated at 85° C. with solution 3, comprising 20 mM NaOH, buffered to pH 10 with Tris-HCl.
Figure 6B:
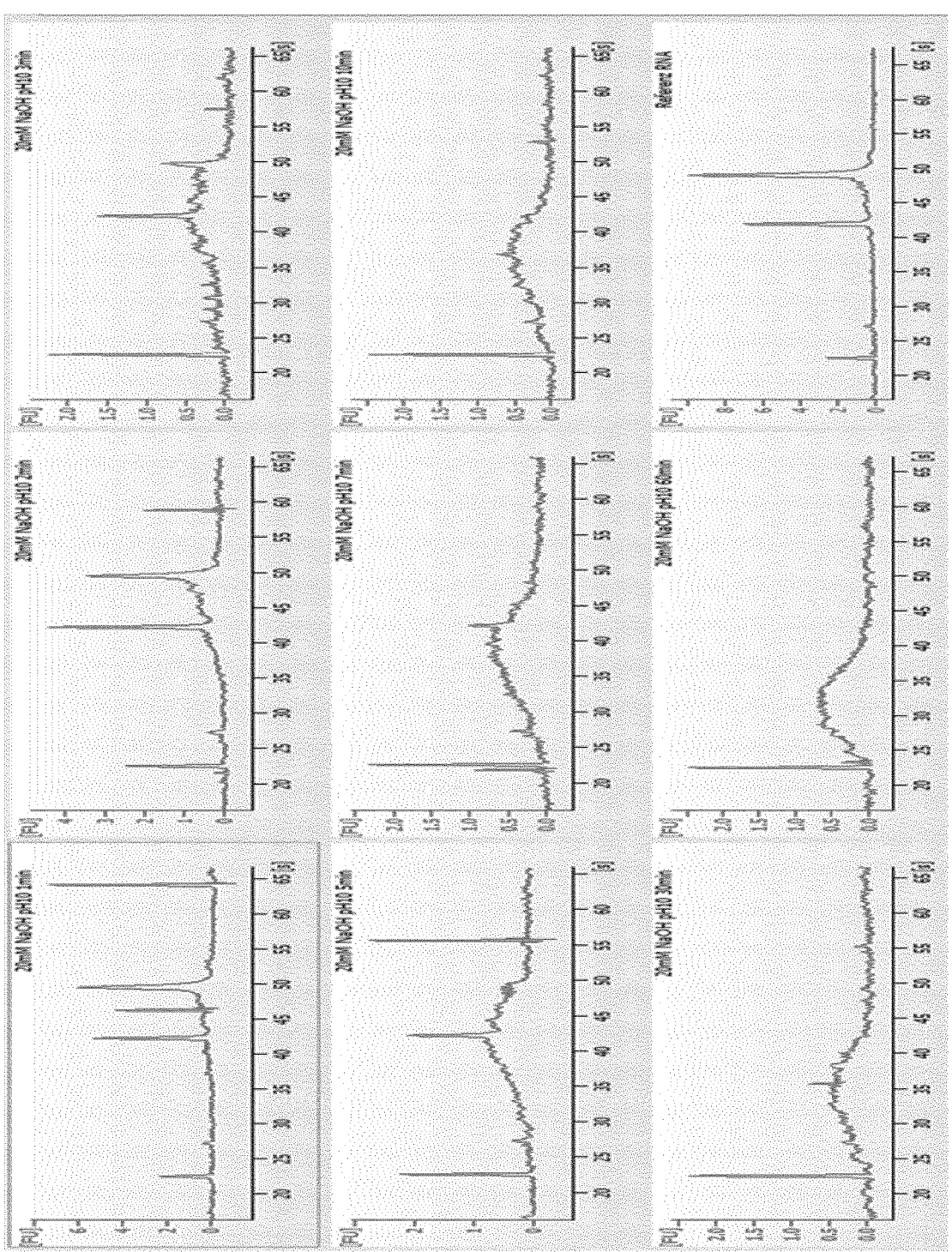
Figure 7A:
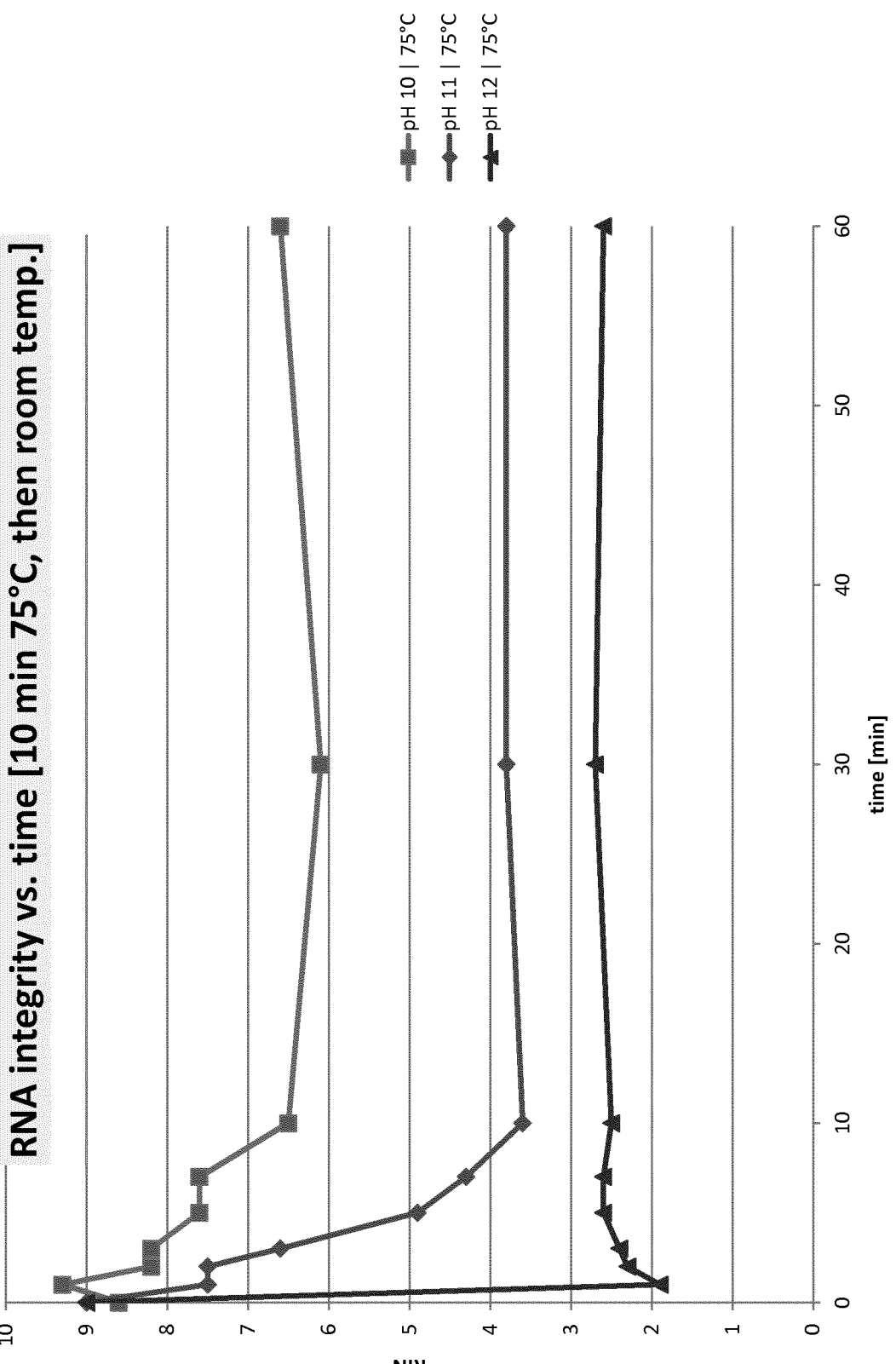
FIGS. 7A to 7D summarize results of Examples 1 and 2.
Figure 7B:
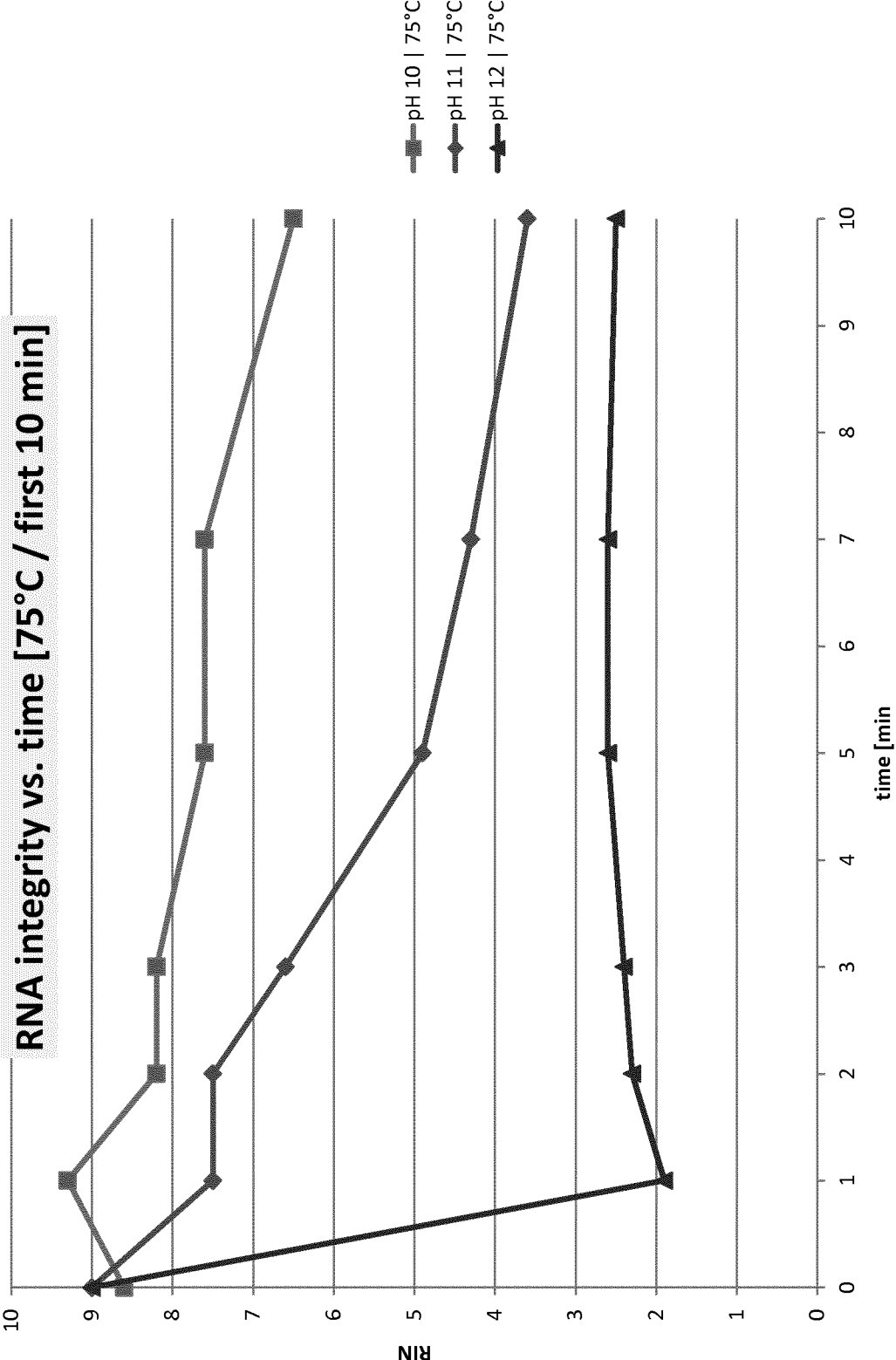
Figure 7C:
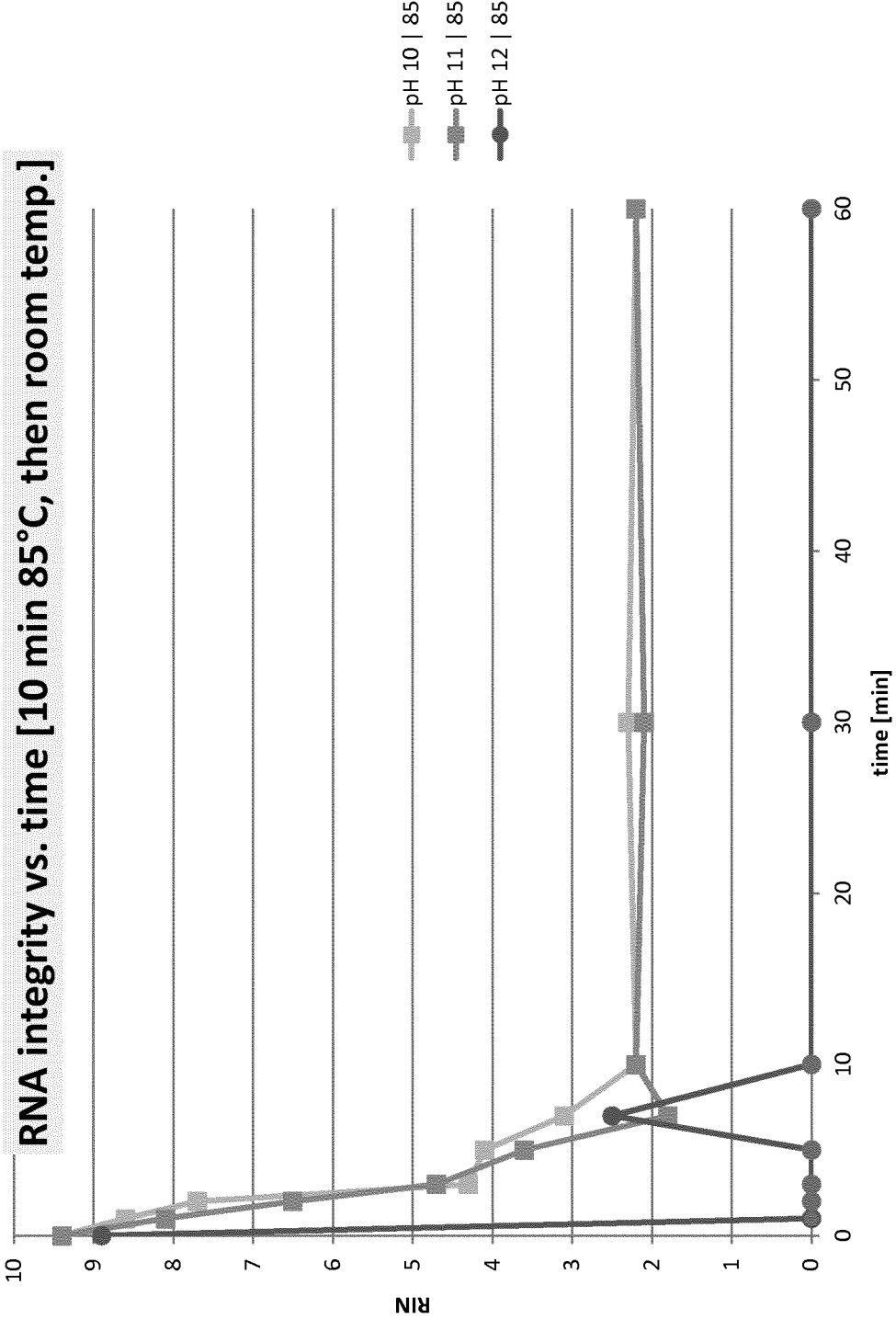
Figure 7D:
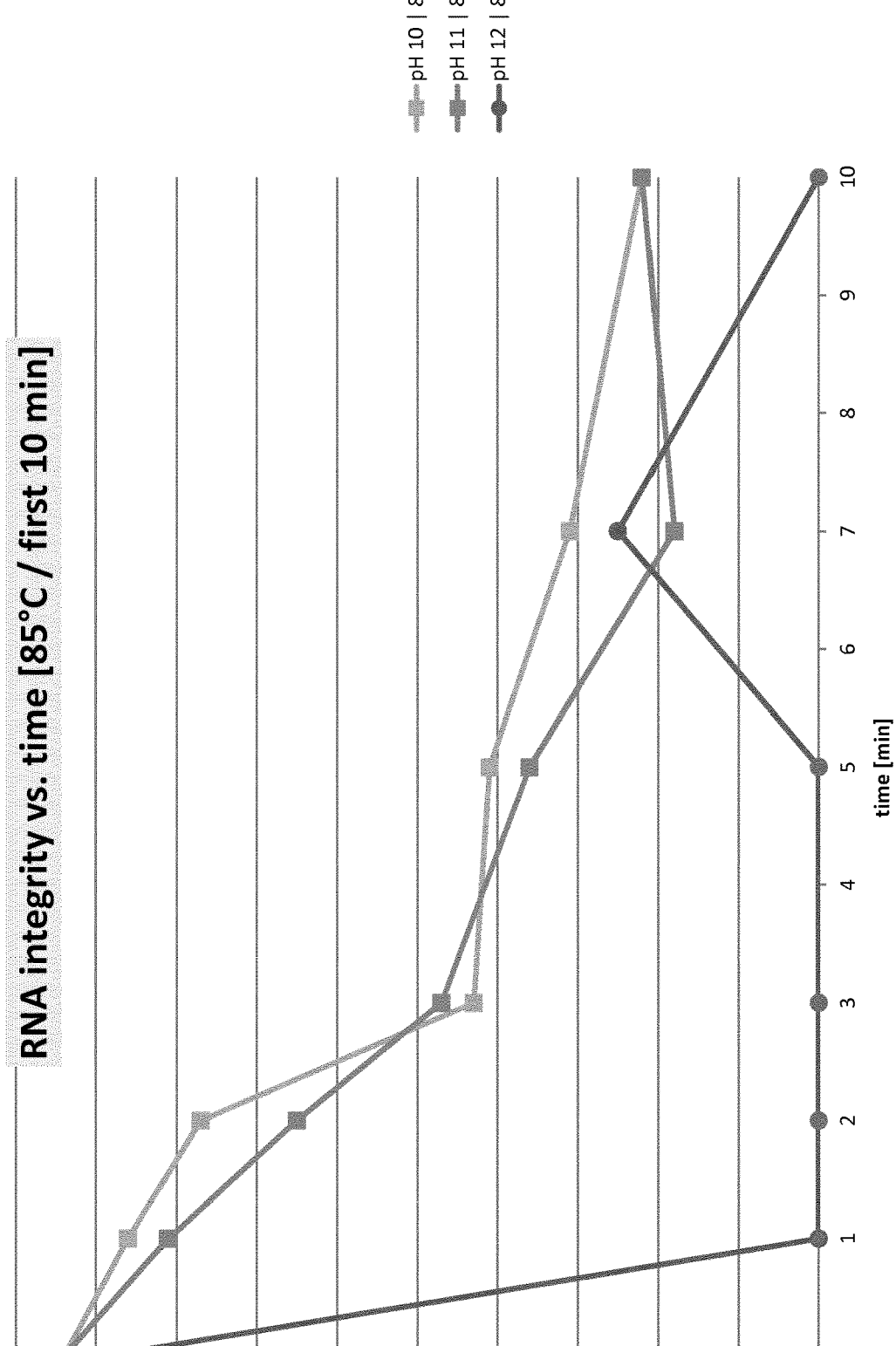

Results:

The results obtained for the solution 1-3 are shown in FIGS. 4-6 and Tables 4-6 below and comprise the representation of results obtained with the Agilent BioAnalyzer system as gel-like images (FIGS. 4A, 5A, 6A), as electropherograms (FIGS. 4B, 5B and 6B), and in tabular format (Tables 4-6).

(a) Results for Solution 1

FIG. 4 shows Agilent BioAnalyzer images of human total RNA incubated at 85° C. with solution 1, comprising 20 mM NaOH, ca. pH 12. FIG. 4A shows a gel-like image. The y axis shows the size of the RNA, here expressed as time required to pass through the gel chip. The figure shows the ladder (L) as well as samples 1-9, wherein the samples are as indicated below:

| | |
|---|---|
| Sample 1: 20 mM NaOH | 1 min |
| Sample 2: 20 mM NaOH | 2 min |
| Sample 3: 20 mM NaOH | 3 min |
| Sample 4: 20 mM NaOH | 5 min |
| Sample 5: 20 mM NaOH | 7 min |
| Sample 6: 20 mM NaOH | 10 min |
| Sample 7: 20 mM NaOH | 30 min |
| Sample 8: 20 mM NaOH | 60 min |
| Sample 9: Reference RNA | |

The 28S and 18S ribosomal RNAs are showing as distinct bands in the reference sample 9. The degradation of RNA occurs immediately after starting the incubation in the alkaline solution, and the 28S and 18S ribosomal RNA bands are not readily detectable for samples 1-8.

FIG. 4B shows the results in form of an electropherogram. The y axis shows the relative intensity of the fluorescence signal that is proportional to the RNA concentration at any given size. The x axis shows the relative RNA size as migration time through the gel chip (higher number=larger molecule size). Again, the 28S and 18S ribosomal RNAs are visible as distinct peaks in the reference sample 9 but are not readily detectable for samples 1-8, indicating that strong RNA degradation occurred in those samples.

Table 4 below also shows the degradation of RNA in samples 1-8. The degradation is indicated by very low RIN values. For some samples, the determination of RIN values was not possible (indicated by "N/A"). This was probably due to low total RNA concentration that was likely caused by fast RNA degradation under these conditions.

TABLE 4

| Sample Name | RIN Value |
|---|---|
| 20 mm NaOH 1 min [85° C.] | RIN N/A |
| 20 mm NaOH 2 min [85° C.] | RIN N/A |
| 20 mm NaOH 3 min [85° C.] | RIN N/A |
| 20 mm NaOH 5 min [85° C.] | RIN N/A |
| 20 mm NaOH 7 min [85° C.] | RIN: 2.50 |
| 20 mm NaOH 10 min [85° C.] | RIN N/A |
| 20 mm NaOH 30 min [85° C.] | RIN N/A |
| 20 mm NaOH 60 min [85° C.] | RIN N/A |
| Reference RNA | RIN: 8.90 |

(b) Results for Solution 2

FIG. 5 shows Agilent BioAnalyzer images of human total RNA incubated at 85° C. with solution 2, comprising 20 mM NaOH, buffered to pH 11 with Tris-HCl. FIG. 5A shows a gel-like image. The y axis shows the size of the RNA, here expressed as time required to pass through the gel chip. The figure shows the ladder (L) as well as samples 1-9, wherein the samples are as indicated below:

| | |
|---|---|
| Sample 1: pH 11 | 1 min |
| Sample 2: pH 11 | 2 min |
| Sample 3: pH 11 | 3 min |
| Sample 4: pH 11 | 5 min |
| Sample 5: pH 11 | 7 min |
| Sample 6: pH 11 | 10 min |
| Sample 7: pH 11 | 30 min |
| Sample 8: pH 11 | 60 min |
| Sample 9: Reference RNA | |

The 28S and 18S ribosomal RNAs are showing as distinct bands in reference sample 9, and are also visible for samples 1-3. The degradation of RNA occurs rapidly after starting the incubation in the alkaline solution, and bands for 28S and 18S ribosomal RNAs are hardly visible or not visible at all for longer incubation periods.

FIG. 5B shows the results in form of an electropherogram. The y axis shows the relative intensity of the fluorescence signal that is proportional to the RNA concentration at any given size. The x axis shows the relative RNA size as migration time through the gel chip (higher number=larger molecule size). Again, the 28S and 18S ribosomal RNAs are visible as distinct peaks in the reference sample 9, but peaks are not detectable for samples 4-8.

The degradation of RNA occurs rapidly after starting the incubation in the alkaline solution as also shown by lower RIN values, which can be seen from Table 5 below. In particular, all RIN values are below that of the reference sample, with RIN values of below 5 for samples 3-8.

TABLE 5

| Sample Name | RIN Value |
|---|---|
| 20 mm NaOH pH 11 1 min | RIN: 8.10 |
| 20 mm NaOH pH 11 2 min | RIN: 6.50 |
| 20 mm NaOH pH 11 3 min | RIN: 4.70 |
| 20 mm NaOH pH 11 5 min | RIN: 3.60 |
| 20 mm NaOH pH 11 7 min | RIN: 1.80 |
| 20 mm NaOH pH 11 10 min | RIN: 2.20 |
| 20 mm NaOH pH 11 30 min | RIN: 2.10 |
| 20 mm NaOH pH 11 60 min | RIN: 2.20 |
| Reference RNA | RIN: 9.40 |

(c) Results for Solution 3

FIG. 6 shows Agilent BioAnalyzer images of human total RNA incubated at 85° C. with solution 3, comprising 20 mM NaOH, buffered to pH 10 with Tris-HCl. FIG. 6A shows a gel-like image. The y axis shows the size of the RNA, here expressed as time required to pass through the gel chip. The figure shows the ladder (L) as well as samples 1-9, wherein the samples are as indicated below:

| | | |
|---|---|---|
| Sample 1: pH 10 | 1 min | |
| Sample 2: pH 10 | 2 min | |
| Sample 3: pH 10 | 3 min | |
| Sample 4: pH 10 | 5 min | |
| Sample 5: pH 10 | 7 min | |
| Sample 6: pH 10 | 10 min | |
| Sample 7: pH 10 | 30 min | |
| Sample 8: pH 10 | 60 min | |
| Sample 9: Reference RNA | | |

As can be seen from the gel-like image, the 28S and 18S ribosomal RNAs are showing as distinct bands in the reference sample and are also visible in samples 1-2. The 28S RNA band is hardly visible in sample 3. RNA degradation increases with increasing incubation times.

FIG. 6B shows the results in form of an electropherogram. The y axis shows the relative intensity of the fluorescence signal that is proportional to the RNA concentration at any given size. The x axis shows the relative RNA size as migration time through the gel chip (higher number=larger molecule size). The 28S and 18S ribosomal RNAs are showing as distinct peaks in the reference sample.

The degradation of RNA occurs rapidly after starting the incubation in the alkaline solution as shown by the decrease of RIN values with increasing incubation times. This can also be seen from Table 6 below.

TABLE 6

| Sample Name | RIN Value |
|---|---|
| 20 mm NaOH pH 10 1 min | RIN: 8.60 |
| 20 mm NaOH pH 10 2 min | RIN: 7.70 |
| 20 mm NaOH pH 10 3 min | RIN: 4.30 |
| 20 mm NaOH pH 10 5 min | RIN: 4.10 |
| 20 mm NaOH pH 10 7 min | RIN: 3.10 |
| 20 mm NaOH pH 10 10 min | RIN: 2.20 |
| 20 mm NaOH pH 10 30 min | RIN: 2.30 |
| 20 mm NaOH pH 10 60 min | RIN: 2.20 |
| Reference RNA | RIN: 9.40 |

Summary of Results of Examples 1 and 2:

FIG. 7 summarizes results of Examples 1 and 2. FIG. 7A shows the RNA integrity versus time for RNA incubated at 75° C. for up to 10 min at pH 10, 11 or 12. Values for samples incubated for 10 min at 75° C. followed by incubation at room temperature are also shown. FIG. 7B shows the RNA integrity versus time for the first 10 minutes of RNA incubation at 75° C. at pH 10, 11 or 12. FIG. 7C shows the RNA integrity versus time for RNA incubated at 85° C. for up to 10 min at pH 10, 11 or 12. Values for samples incubated for 10 min at 85° C. followed by incubation at room temperature are also shown. FIG. 7D shows the RNA integrity versus time for the first 10 minutes of RNA incubation at 85° C. at pH 10, 11 or 12.

As can be seen:

RNA degradation was observed in all solution or buffer (pH) conditions during the incubation at 75° C. or 85° C.

Higher temperature and higher pH both contribute to faster RNA degradation.

Key observations:

Only pH 10 at 75° C. lead to RIN values>5 at 5 min incubation time.

At 85° C., RIN is 4-5 at pH 10-11 after 3 min incubation.

At 75° C., RIN>6 for pH 11, RIN≈8 for pH 10 after 3 min incubation.

Additional room temperature incubation for up to 1 hour does not lead to measurably higher RNA degradation.

Example 3—RNA Stabilization in Alkaline Solution at High Temperature Using Ammonium Sulfate Human total RNA (RNeasy-extracted) was spiked into different buffers that are also suitable as elution buffers.

Buffer conditions:

20 mM NaOH buffered to pH 11 with Tris (solution 2)

20 mM NaOH buffered to pH 11, plus 2.5 mM ammonium sulfate $((NH_4)_2SO_4)$ (solution 4)

800 ng RNA (1 μl) mixed with 19 μl buffer=start of incubation

At different time points, 2 μl RNA are removed and immediately added to 3 μl 100 mM NaOAc pH 5 to stop the degradation process.

Time course: +1 min|+2 min|+3 min|+5 min|+7 min|+10 min

Incubation temperature at 75° C. or 85° C. (no additional room temp. incubation)

Run RNA samples (1 μl each) on Agilent BioAnalyzer (RNA Nano Kit)

Analyze RNA integrity (RIN) vs. incubation time.

Results:

The results obtained for the solution 2 and 4 are shown in FIGS. 8-11 and Tables 8-11 below and comprise the representation of results obtained with the Agilent BioAnalyzer system as gel-like images (FIGS. 8A-11A), as electropherograms (FIGS. 8B-11B), and in tabular format (Tables 8-11).

(a) Results for Solution 2, Incubation at 75° C.

Figure 8A:
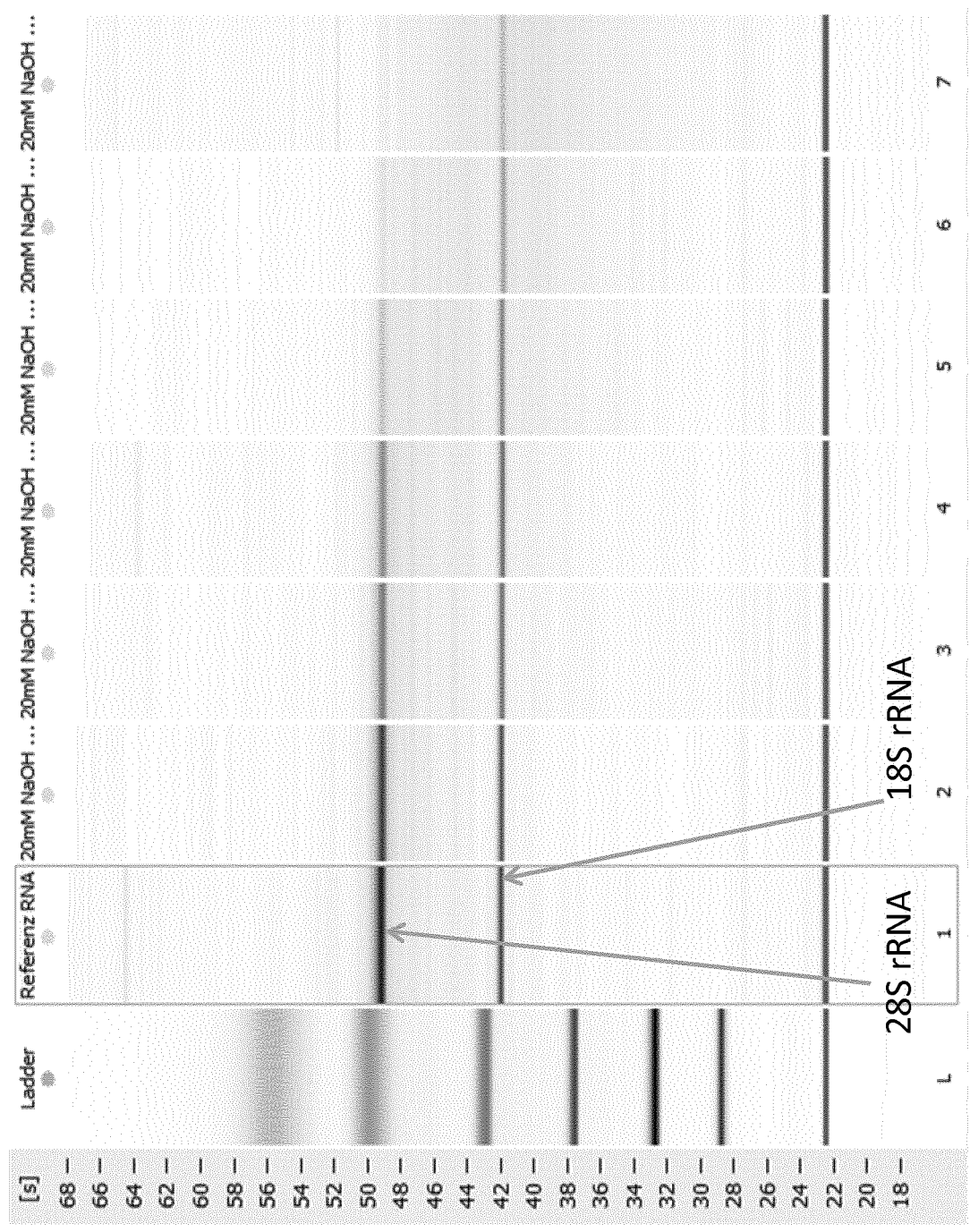
FIGS. 8A and 8B show Agilent BioAnalyzer images (gel-like image and electropherogram) of human total RNA incubated at 75° C. with solution 2, comprising 20 mM NaOH, buffered to pH 11 with Tris-HCl.

FIG. 8 shows Agilent BioAnalyzer images of human total RNA incubated at 75° C. with solution 2, comprising 20 mM NaOH, buffered to pH 11 with Tris-HCl. FIG. 8A shows a gel-like image. The y axis shows the size of the RNA, here expressed as time required to pass through the gel chip. The figure shows the ladder (L) as well as samples 1-7, wherein the samples are as indicated below:

| | | |
|---|---|---|
| Sample 1: Reference RNA | (t = 0) | |
| Sample 2: 20 mM NaOH pH 11 | 1 min | |
| Sample 3: 20 mM NaOH pH 11 | 2 min | |
| Sample 4: 20 mM NaOH pH 11 | 3 min | |
| Sample 5: 20 mM NaOH pH 11 | 5 min | |
| Sample 6: 20 mM NaOH pH 11 | 7 min | |
| Sample 7: 20 mM NaOH pH 11 | 10 min | |

The 28S and 18S ribosomal RNAs are showing as distinct bands in the reference sample and are indicated by arrows. RNA degradation increases with increasing incubation times.

Figure 8B:
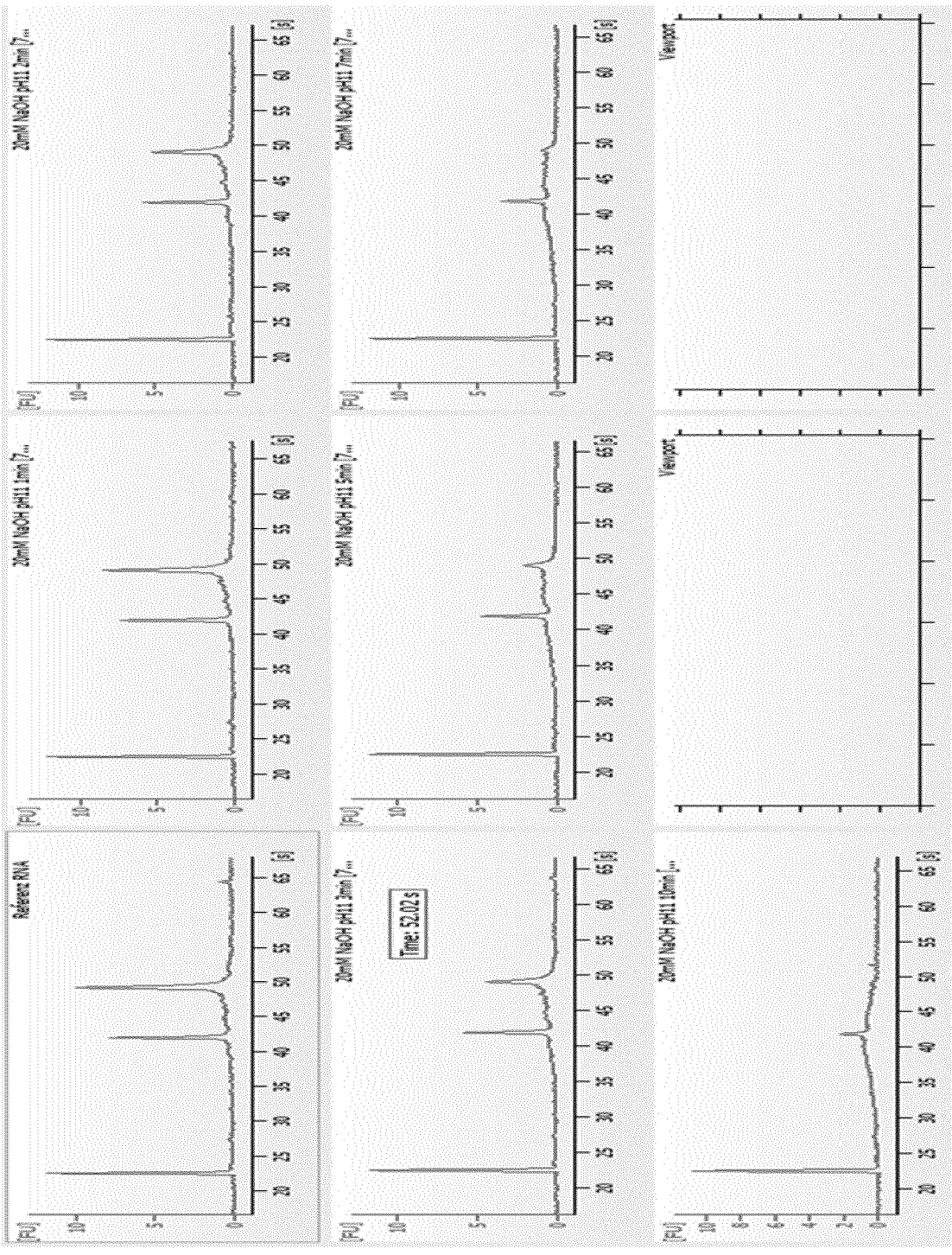

FIG. 8B shows the results in form of an electropherogram. The y axis shows the relative intensity of the fluorescence signal that is proportional to the RNA concentration at any given size. The x axis shows the relative RNA size as migration time through the gel chip (higher number=larger molecule size). The 28S and 18S ribosomal RNAs are visible as distinct peaks in the reference sample 1.

Increasing degradation of RNA occurs with increasing incubation times, as can also be seen from the decrease of RIN values for increasing incubation times shown in Table 8 below. In particular, The RIN value was below 5 for an incubation time of 10 minutes.

TABLE 8

| Sample Name | RIN Value |
| --- | --- |
| Reference RNA | RIN: 9.10 |
| 20 mm NaOH pH 11 1 min [75° C.] | RIN: 9.50 |
| 20 mm NaOH pH 11 2 min [75° C.] | RIN: 8.50 |
| 20 mm NaOH pH 11 3 min [75° C.] | RIN: 8.10 |
| 20 mm NaOH pH 11 5 min [75° C.] | RIN: 6.90 |
| 20 mm NaOH pH 11 7 min [75° C.] | RIN: 5.30 |
| 20 mm NaOH pH 11 10 min [75° C.] | RIN: 4.90 |

(b) Results for Solution 4, Incubation at 75° C.

Figure 9A:
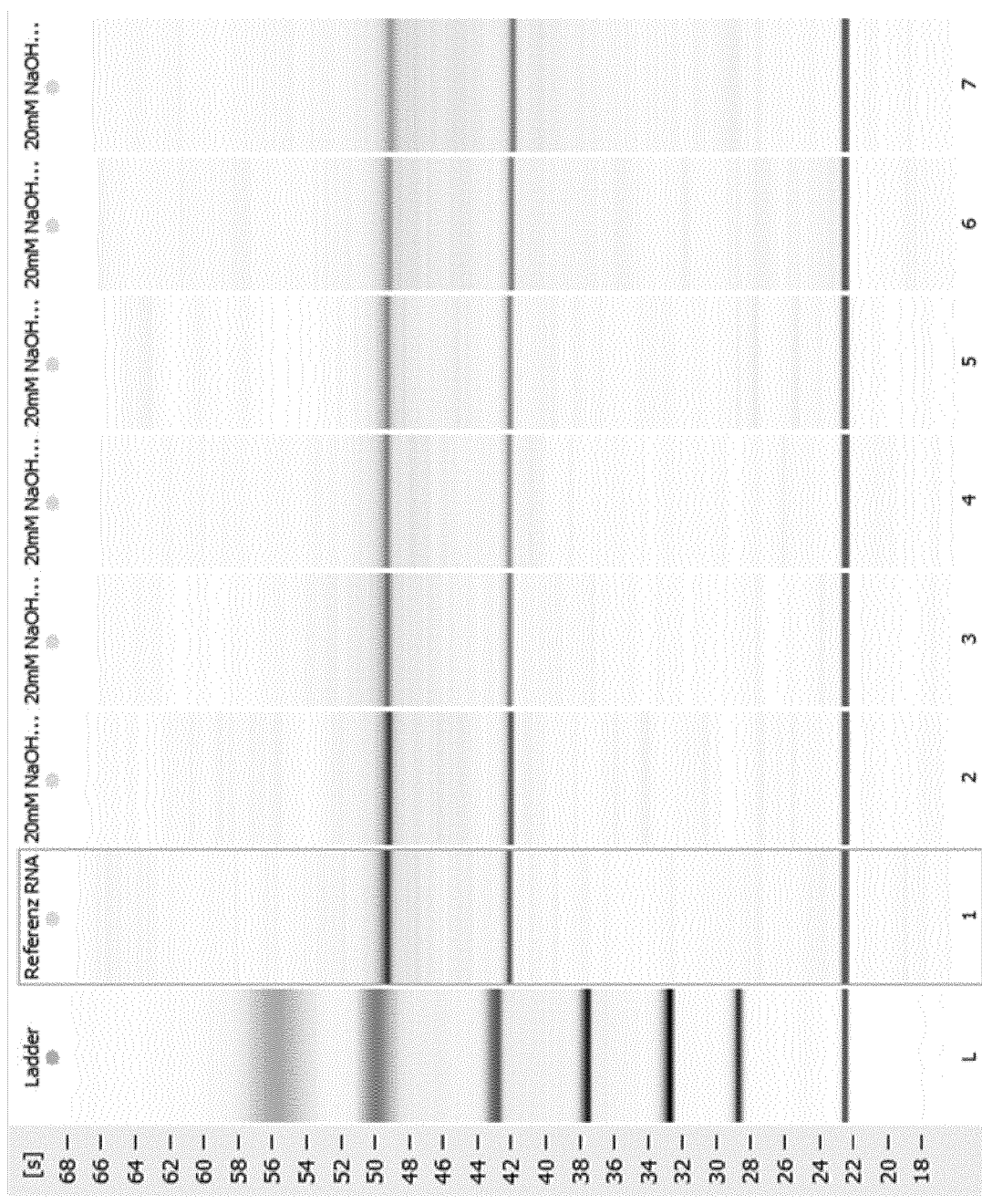
FIGS. 9A and 9B show Agilent BioAnalyzer images (gel-like image and electropherogram) of human total RNA incubated at 75° C. with solution 4, comprising 20 mM NaOH, buffered to pH 11 with Tris-HCl, plus 2.5 mM $(NH_4)_2SO_4$. The degradation of RNA is inhibited and is slowed considerably by adding ammonium sulfate.

FIG. 9 shows Agilent BioAnalyzer images of human total RNA incubated at 75° C. with solution 4, comprising 20 mM NaOH, buffered to pH 11 with Tris-HCl, plus 2.5 mM $(NH_4)_2SO_4$. FIG. 9A shows a gel-like image. The y axis shows the size of the RNA, here expressed as time required to pass through the gel chip. The figure shows the ladder (L) as well as samples 1-7, wherein the samples are as indicated below:

| | |
| --- | --- |
| Sample 1: Reference RNA | (t = 0) |
| Sample 2: 20 mM NaOH + 2.5 mM $(NH_4)_2SO_4$ | 1 min |
| Sample 3: 20 mM NaOH + 2.5 mM $(NH_4)_2SO_4$ | 2 min |
| Sample 4: 20 mM NaOH + 2.5 mM $(NH_4)_2SO_4$ | 3 min |
| Sample 5: 20 mM NaOH + 2.5 mM $(NH_4)_2SO_4$ | 5 min |
| Sample 6: 20 mM NaOH + 2.5 mM $(NH_4)_2SO_4$ | 7 min |
| Sample 7: 20 mM NaOH + 2.5 mM $(NH_4)_2SO_4$ | 10 min |

The 28S and 18S ribosomal RNAs are showing as distinct bands in all samples, even after prolonged incubation. The degradation of RNA is slowed considerably by adding ammonium sulfate.

Figure 9B:
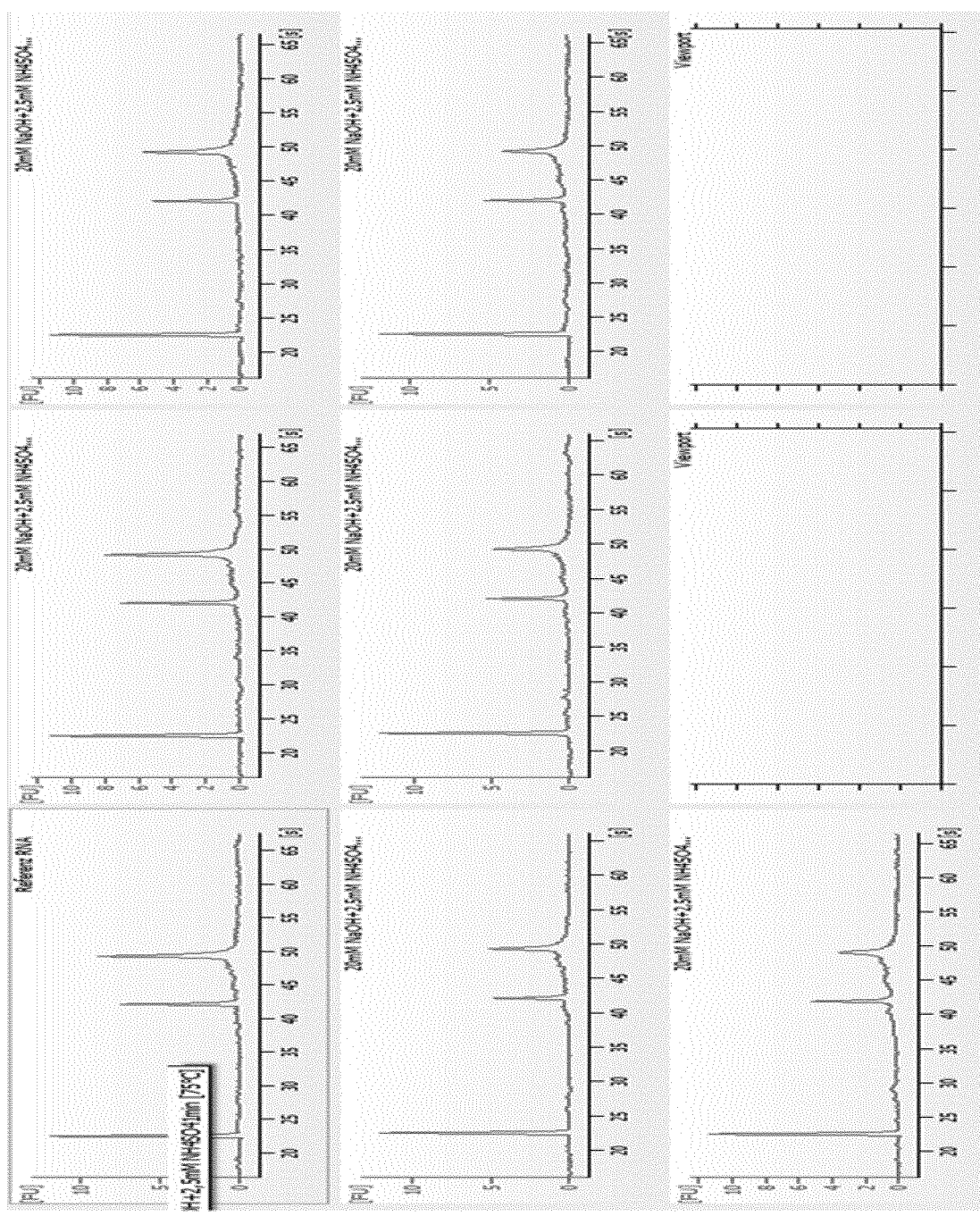

FIG. 9B shows the results in form of an electropherogram. The y axis shows the relative intensity of the fluorescence signal that is proportional to the RNA concentration at any given size. The x axis shows the relative RNA size as migration time through the gel chip (higher number=larger molecule size). The 28S and 18S ribosomal RNAs are visible as distinct peaks in the reference sample 1. Again, it can be seen that the degradation of RNA is slowed considerably by adding ammonium sulfate, and distinct peaks for 18S and 28S RNA are readily visible for all samples.

That the degradation of RNA is slowed considerably by adding ammonium sulfate can also be seen from the RIN values during the 10 min incubation, shown in Table 9 below. The values obtained are higher and RNA integrity is improved compared to incubation in the absence of ammonium sulfate. RIN values well above 5 and about 7 were achieved for all samples.

TABLE 9

| Sample Name | RIN Value |
| --- | --- |
| Reference RNA | RIN: 9.60 |
| 20 mm NaOH + 2.5 mm $(NH_4)_2SO_4$ 1 min [75° C.] | RIN: 9 |
| 20 mm NaOH + 2.5 mm $(NH_4)_2SO_4$ 2 min [75° C.] | RIN: 8.90 |
| 20 mm NaOH + 2.5 mm $(NH_4)_2SO_4$ 3 min [75° C.] | RIN: 9 |
| 20 mm NaOH + 2.5 mm $(NH_4)_2SO_4$ 5 min [75° C.] | RIN: 8.60 |

TABLE 9-continued

| Sample Name | RIN Value |
| --- | --- |
| 20 mm NaOH + 2.5 mm $(NH_4)_2SO_4$ 7 min [75° C.] | RIN: 8.30 |
| 20 mm NaOH + 2.5 mm $(NH_4)_2SO_4$ 10 min [75° C.] | RIN: 7.60 |

(c) Results for Solution 2, Incubation at 85° C.

Figure 10A:
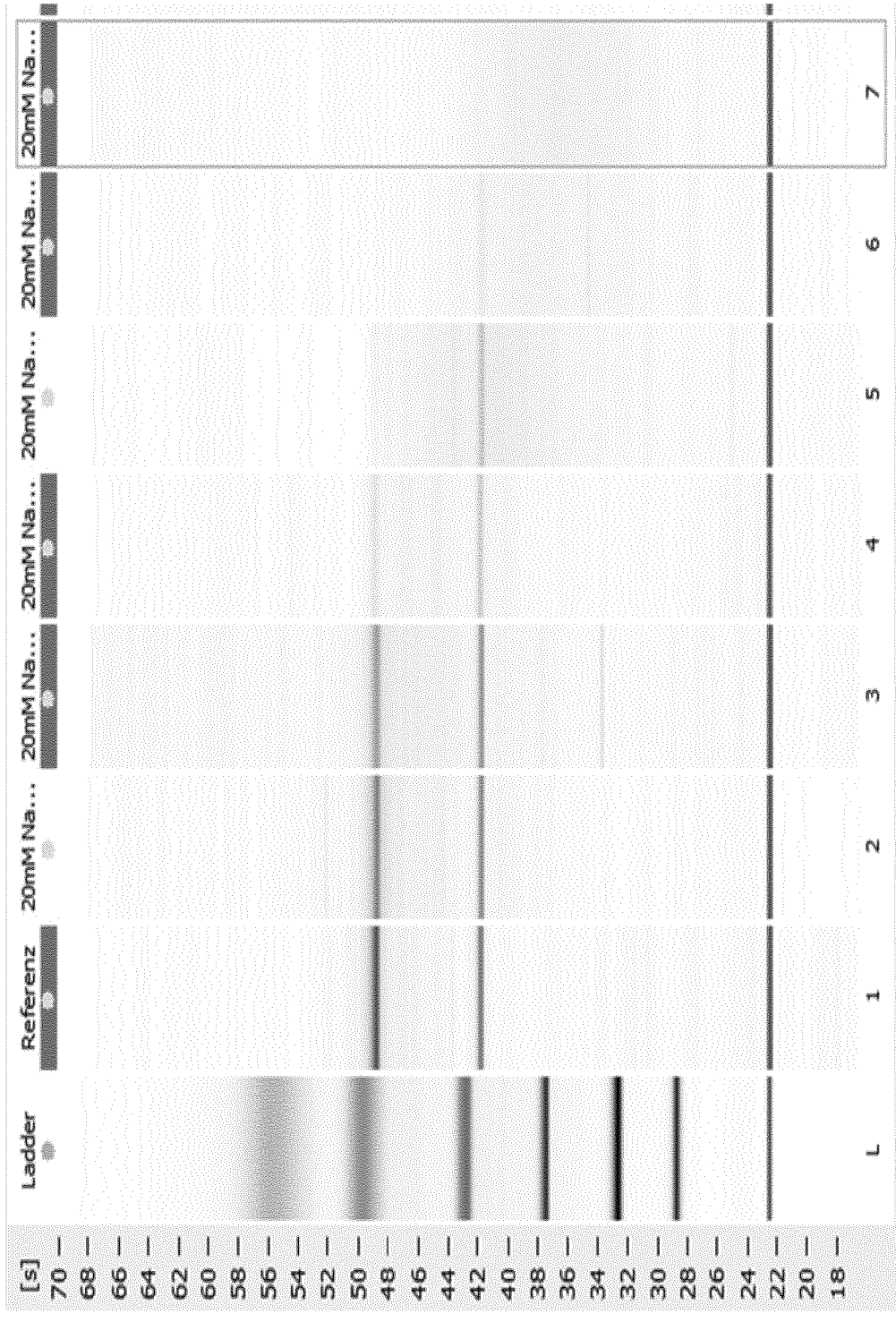
FIGS. 10A and 10B show Agilent BioAnalyzer images (gel-like image and electropherogram) of human total RNA incubated at 85° C. with solution 2, comprising 20 mM NaOH, buffered to pH 11 with Tris-HCl.

FIG. 10 shows Agilent BioAnalyzer images of human total RNA incubated at 85° C. with solution 2, comprising 20 mM NaOH, buffered to pH 11 with Tris-HCl. FIG. 10A shows a gel-like image. The y axis shows the size of the RNA, here expressed as time required to pass through the gel chip. The figure shows the ladder (L) as well as samples 1-7, wherein the samples are as indicated below:

| | |
| --- | --- |
| Sample 1: Reference RNA | (t = 0) |
| Sample 2: 20 mM NaOH pH 11 | 1 min |
| Sample 3: 20 mM NaOH pH 11 | 2 min |
| Sample 4: 20 mM NaOH pH 11 | 3 min |
| Sample 5: 20 mM NaOH pH 11 | 5 min |
| Sample 6: 20 mM NaOH pH 11 | 7 min |
| Sample 7: 20 mM NaOH pH 11 | 10 min |

The 28S and 18S ribosomal RNAs are showing as distinct bands. The degradation of RNA occurs rapidly after starting the incubation in the alkaline solution.

Figure 10B:
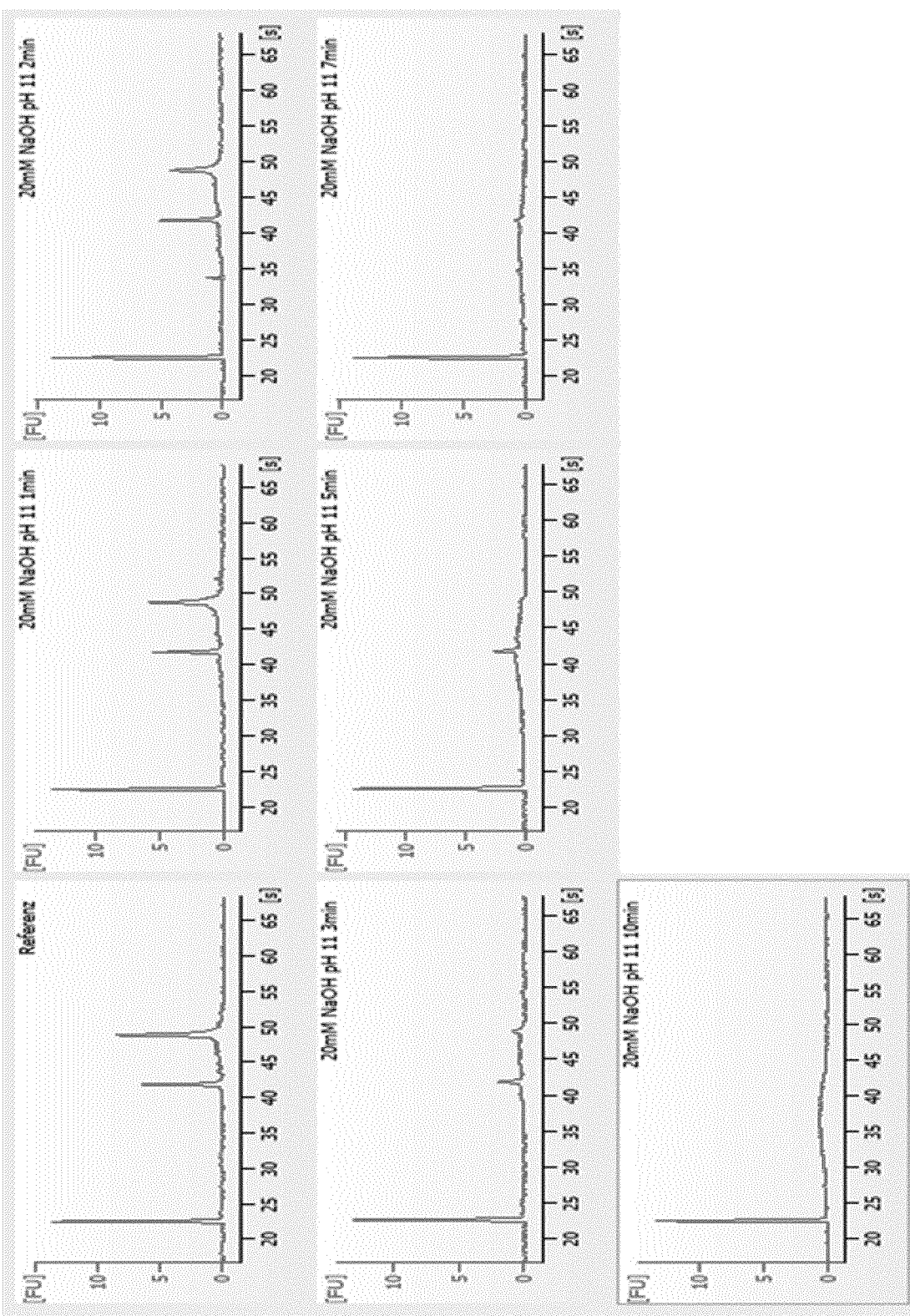

FIG. 10B shows the results in form of an electropherogram. The y axis shows the relative intensity of the fluorescence signal that is proportional to the RNA concentration at any given size. The x axis shows the relative RNA size as migration time through the gel chip (higher number=larger molecule size). Again, it can be seen that the degradation of RNA occurs rapidly after starting the incubation in the alkaline solution.

This can also be seen from the lower RIN values, depicted in Table 10 below.

TABLE 10

| Sample Name | | RIN Value |
| --- | --- | --- |
| 20 mM NaOH pH 11 | 1 min | RIN: 8.60 |
| 20 mM NaOH pH 11 | 2 min | RIN N/A |
| 20 mM NaOH pH 11 | 3 min | RIN N/A |
| 20 mM NaOH pH 11 | 5 min | RIN: 5.30 |
| 20 mM NaOH pH 11 | 7 min | RIN N/A |
| 20 mM NaOH pH 11 | 10 min | RIN N/A |

(d) Results for Solution 4, Incubation at 85° C.

Figure 11A:
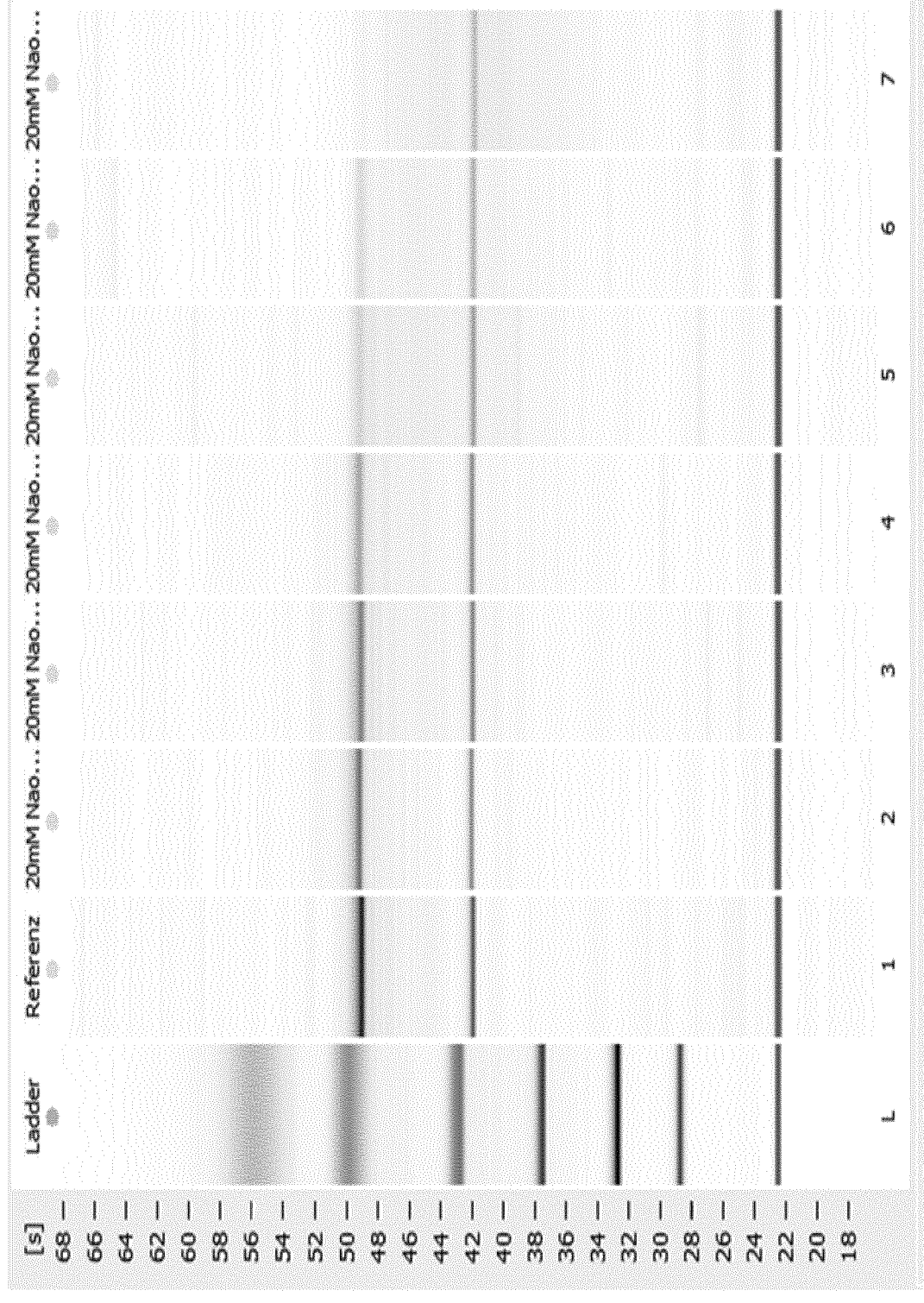
FIGS. 11A and 11B show Agilent BioAnalyzer images (gel-like image and electropherogram) of human total RNA incubated at 85° C. with solution 4, comprising 20 mM NaOH, buffered to pH 11 with Tris-HCl, plus 2.5 mM $(NH_4)_2SO_4$. The degradation of RNA is inhibited and is slowed considerably by adding ammonium sulfate.

FIG. 11 shows Agilent BioAnalyzer images of human total RNA incubated at 85° C. with solution 4, comprising 20 mM NaOH, buffered to pH 11 with Tris-HCl, plus 2.5 mM $(NH_4)_2SO_4$. FIG. 11A shows a gel-like image. The y axis shows the size of the RNA, here expressed as time required to pass through the gel chip. The figure shows the ladder (L) as well as samples 1-7, wherein the samples are as indicated below:

| | |
| --- | --- |
| Sample 1: Reference RNA | (t = 0) |
| Sample 2: 20 mM NaOH + 2.5 mM $(NH_4)_2SO_4$ | 1 min |
| Sample 3: 20 mM NaOH + 2.5 mM $(NH_4)_2SO_4$ | 2 min |
| Sample 4: 20 mM NaOH + 2.5 mM $(NH_4)_2SO_4$ | 3 min |
| Sample 5: 20 mM NaOH + 2.5 mM $(NH_4)_2SO_4$ | 5 min |
| Sample 6: 20 mM NaOH + 2.5 mM $(NH_4)_2SO_4$ | 7 min |
| Sample 7: 20 mM NaOH + 2.5 mM $(NH_4)_2SO_4$ | 10 min |

The 28S and 18S ribosomal RNAs are showing as distinct bands. The degradation of RNA is slowed considerably by adding ammonium sulfate also at an incubation temperature of 85° C.

Figure 11B:
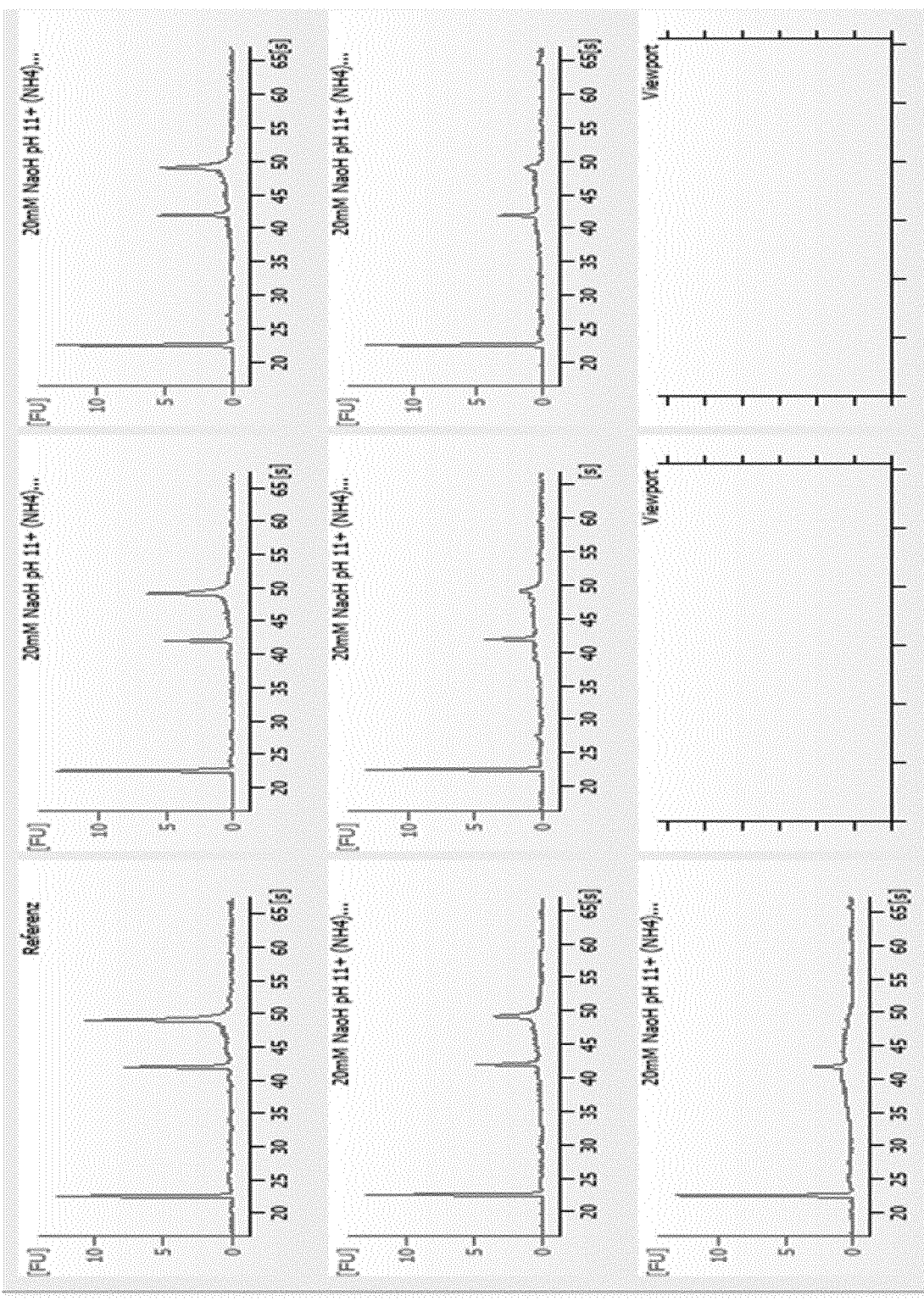

FIG. 11B shows the results in form of an electropherogram. The y axis shows the relative intensity of the fluorescence signal that is proportional to the RNA concentration at any given size. The x axis shows the relative RNA size as migration time through the gel chip (higher number=larger molecule size). The 28S and 18S ribosomal RNAs are visible as distinct peaks in the reference sample 1. Again, it can be seen that the degradation of RNA is slowed considerably by adding ammonium sulfate.

That the degradation of RNA is slowed considerably by adding ammonium sulfate can also be seen from the RIN values during the 10 min incubation at 85° C. The values obtained are higher and RNA integrity is improved compared to incubation in the absence of ammonium sulfate. See also Table 11 below. A RIN of above 5 was achieved for all samples in the presence of ammonium sulfate, with a RIN of above 7 for the majority of the samples.

TABLE 11

| Sample Name | RIN Value |
|---|---|
| Reference RNA | RIN: 9.20 |
| 20 mm NaOH pH 11 + $(NH_4)_2SO_4$ 1 min | RIN: 8.90 |
| 20 mm NaOH pH 11 + $(NH_4)_2SO_4$ 2 min | RIN: 8.60 |
| 20 mm NaOH pH 11 + $(NH_4)_2SO_4$ 3 min | RIN: 8.40 |
| 20 mm NaOH pH 11 + $(NH_4)_2SO_4$ 5 min | RIN: 7.10 |
| 20 mm NaOH pH 11 + $(NH_4)_2SO_4$ 7 min | RIN: 7.10 |
| 20 mm NaOH pH 11 + $(NH_4)_2SO_4$ 10 min | RIN: 5.40 |

Figure 12A:
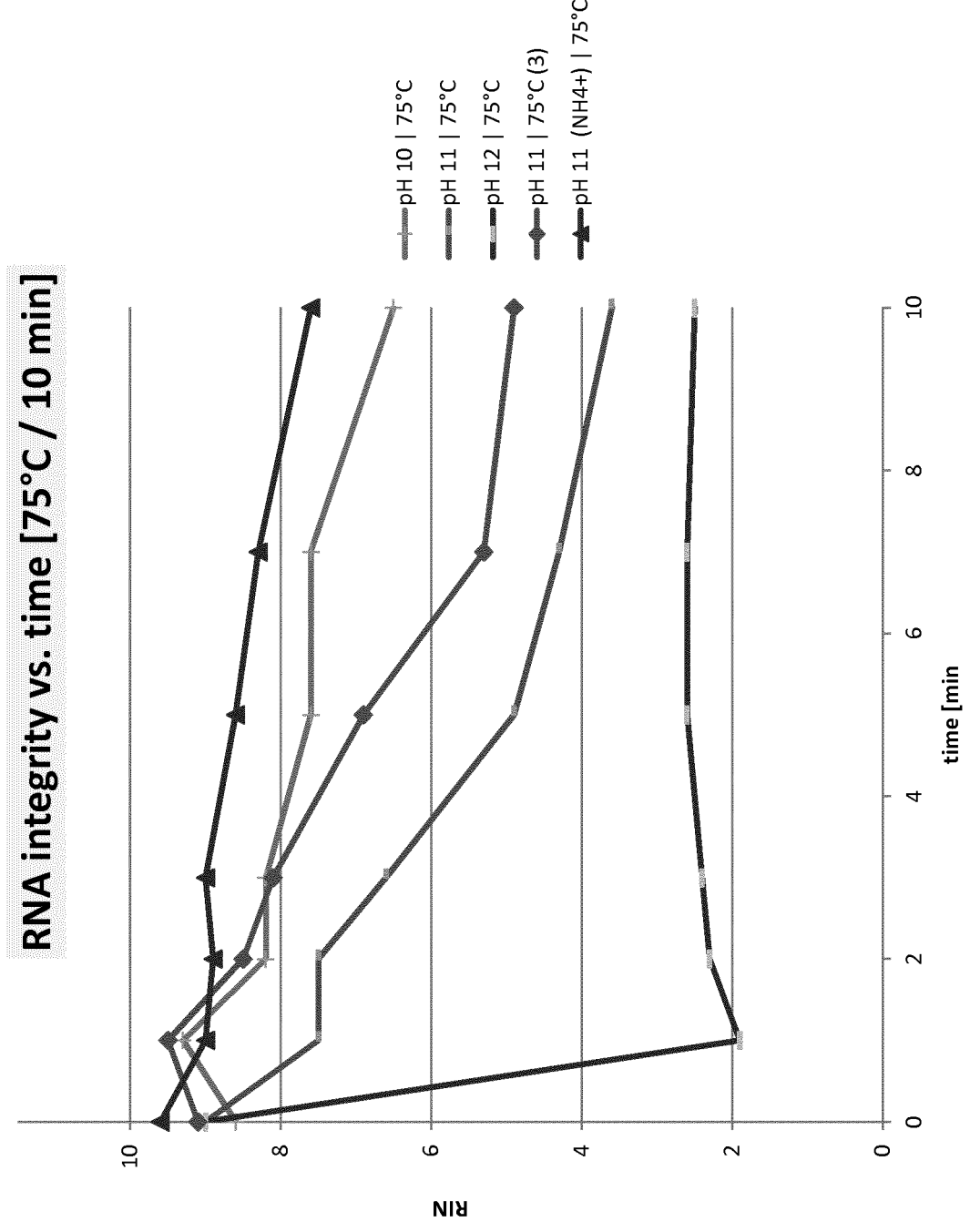
FIGS. 12A and 12B summarize results of Examples 1 to 3.
Figure 12B:
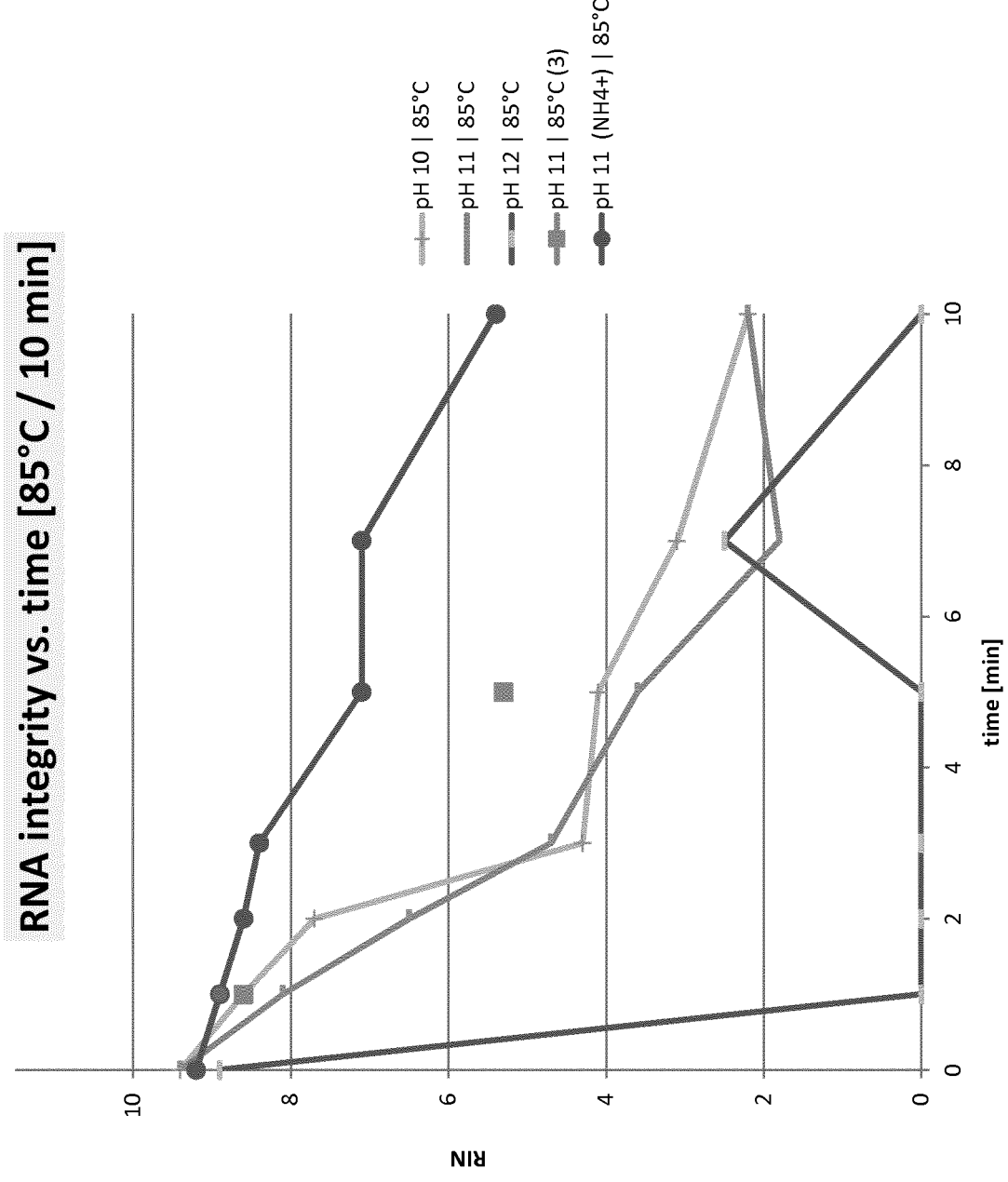

Summary of Results of Example 3:
   RNA degradation observed in all solution or buffer (pH) conditions during incubation at 75° C. or 85° C.
   Higher temperature and higher pH both contribute to faster RNA degradation.
   Adding ammonium sulfate (2.5 mM) leads to inhibited and slower RNA degradation and therefore results in RNA stabilization at pH 11—both at 75° C. and 85° C.
Summary of RNA Stability Observed in Examples 1 to 3
   The results of Examples 1-3 are summarized in FIGS. 12A and 12B. FIG. 12A shows the RNA integrity versus time for RNA incubated at 75° C. for up to 10 min at pH 10, 11 or 12, and for RNA incubated at 75° C. for up to 10 min at pH 11 in the presence of 2.5 mM ammonium sulfate. FIG. 12B shows the RNA integrity versus time for RNA incubated at 85° C. for up to 10 min at pH 10, 11 or 12, and for RNA incubated at 85° C. for up to 10 min at pH 11 in the presence of 2.5 mM ammonium sulfate.

It is concluded that the presence of ammonium sulfate at low concentrations (e.g. about 2.5 mM) leads to a strongly stabilizing effect on RNA under high temperature conditions (e.g., temperature range of 70° C. to 90° C., 72° C. to 88° C., in particular 75° C. to 85° C.) and high pH conditions (e.g., pH of 9 or higher, such as a pH of 10 to 12, in particular pH of 11). In particular, RNA was efficiently stabilized during a 10 minute incubation at 75° C.-85° C.; this scenario mimics the conditions required to elute RNA off an anion exchange resin, which makes the eluted RNA (when stabilized with a low concentration of ammonium sulfate) suitable for highly sensitive and quantitative detection, such as in qPCR-based detection of viral RNA (e.g., HCV, HIV) in diagnostics assays.

Example 4—RNA Stabilization by $(NH_4)_2SO_4$ and EDTA in Solution at pH 11 and 85° C.

Study Design:
   Human total RNA (RNeasy-extracted) was spiked into different buffers which are suitable as elution buffers.
   Buffer conditions:
      Buffer 1: 20 mM NaOH buffered to pH 11;
      Buffer 2: 20 mM NaOH buffered to pH 11, plus 0.01 mM (10 μM) EDTA;
      Buffer 3: 20 mM NaOH buffered to pH 11, plus 0.01 mM (10 μM) EDTA, plus 1 mM ammonium sulfate $((NH_4)_2SO_4)$;
      Buffer 4: 20 mM NaOH buffered to pH 11, plus 0.01 mM (10 μM) EDTA, plus 2.5 mM ammonium sulfate $((NH_4)_2SO_4)$.
   800 ng RNA (1 μl) mixed with 19 μl buffer=start of incubation (total volume 20 μl).
   At different time points, 2 μl RNA are removed and immediately added to 3 μl 100 mM NaOAc, pH 5, to stop the degradation process.
   Time course of incubation:
      +1 min|+2 min|+3 min|+5 min|+7 min|+10 min|+15 min|+20 min|+30 min
   Incubation temperature: 85° C.
   RNA samples (1 μl each) were run on an Agilent BioAnalyzer (RNA Pico Kit).
   Analyzed RNA integrity (RIN) vs. incubation time.
   Analyzed amount of remaining full-length 18S rRNA, 28S rRNA vs. incubation time based on the relative full-length band intensity.
Details of this Analysis of Remaining Full-Length 18S rRNA, 28S rRNA:
   The quantity of full-length rRNA was determined by densitometric measurement of the intensity of the respective rRNA band on the Agilent Bioanalyzer gel chip. To this end, the relative RNA intensity was plotted against the time required for traveling through the gel capillary, where higher molecular weight (=longer) RNA molecules travel more slowly than shorter RNAs. The amount of the respective full-length RNA was determined by measuring the area under the respective RNA peak in the intensity vs. time trace. A set of defined marker RNA molecules was run alongside the samples with every capillary gel chip, such that the intensity of the RNA samples could be calibrated against the marker RNA. Then, the measured relative amount of full-length rRNA was plotted against the incubation time, with the rRNA amount at time point "0" being normalized to 100%; the rRNA half-life was determined by fitting a first-order degradation kinetics to the data.
      Analyzed amplifiable 18S rRNA using 66 nt and 500 nt amplicons vs. incubation time. Calculated half-lives based on the Ct values vs. incubation time.
Details of this Analysis of Amplifiable 18S rRNA:
   The 18S rRNA was quantified by a duplex real-time RT-PCR using the Quantitect Multiplex RT-PCR Kit (QIAGEN) on an ABI 7900 instrument according the manufacturer's instructions. The Ct values for every RNA sample were determined using the ABI 7900 analysis software. The following primer and probe sequences were used:

| name | sequence 5'-3' | probe labels |
|------|----------------|--------------|
| 18S 66 bp forward (SEQ ID NO: 1) | GCCGCTAGAGGTGAAATTCTTG | 5' Cy5-BHQ2* 3' |
| 18S 66 bp reverse (SEQ ID NO: 2) | CATTCTTGGCAAATGCTTTCG | |
| 18S 66 bp probe (SEQ ID NO: 3) | ACCGGCGCAAGACGGACCAGA | |
| 18S 500 bp forward (SEQ ID NO: 4) | GTCGCTCGCTCCTCTCCTACTT | 5' FAM-BHQ1* 3' |
| 18S 500 bp reverse (SEQ ID NO: 5) | GGCTGCTGGCACCAGACTT | |
| 18S 500 bp probe (SEQ ID NO: 6) | CTAATACATGCCGACGGGCGCTGAC | |

Figure 13A:
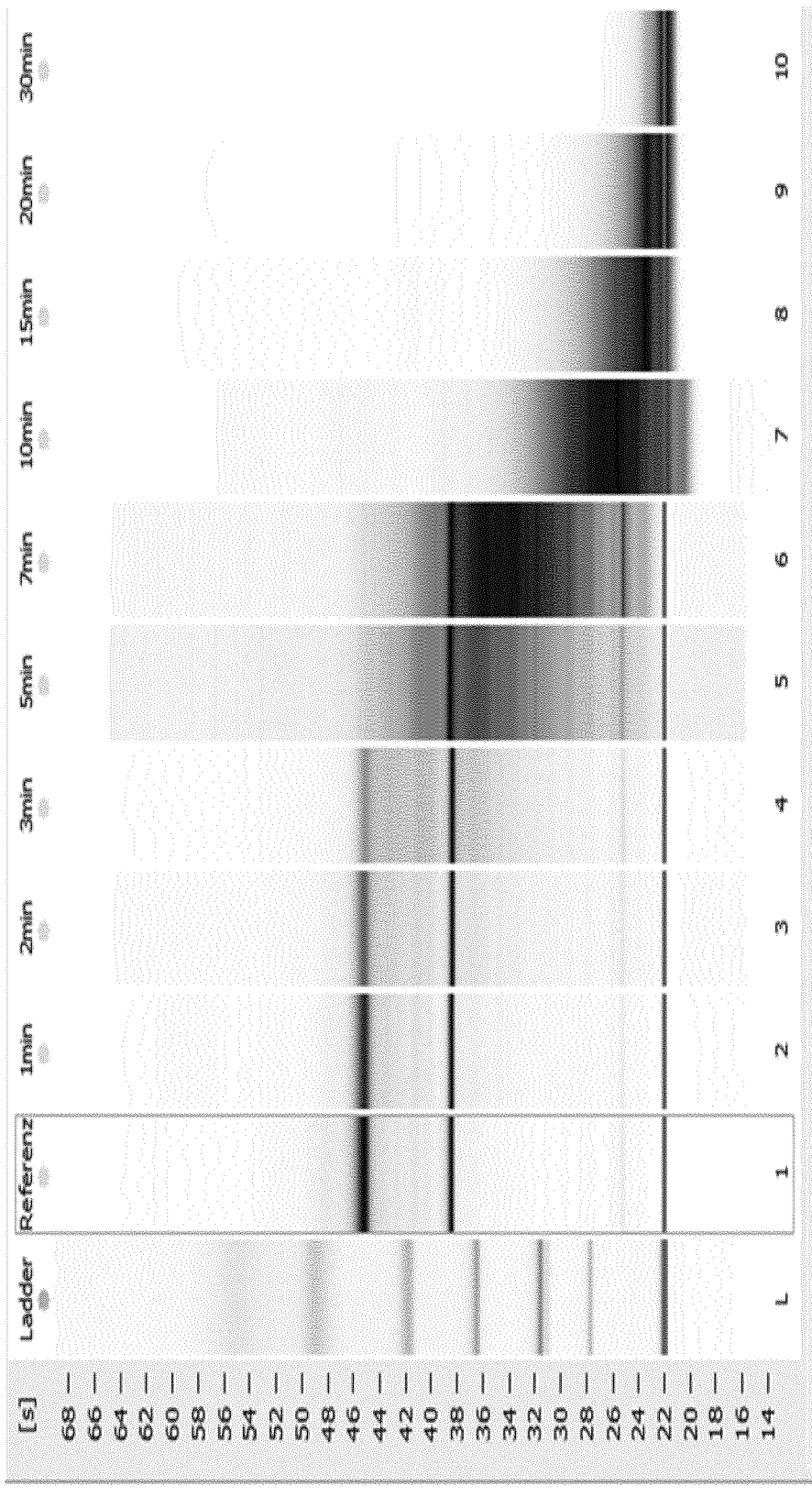
FIGS. 13A to 13D show Agilent BioAnalyzer images (gel-like images) of human total RNA incubated at 85° C., pH 11, with different solutions as further described in Example 4.
Figure 13B:
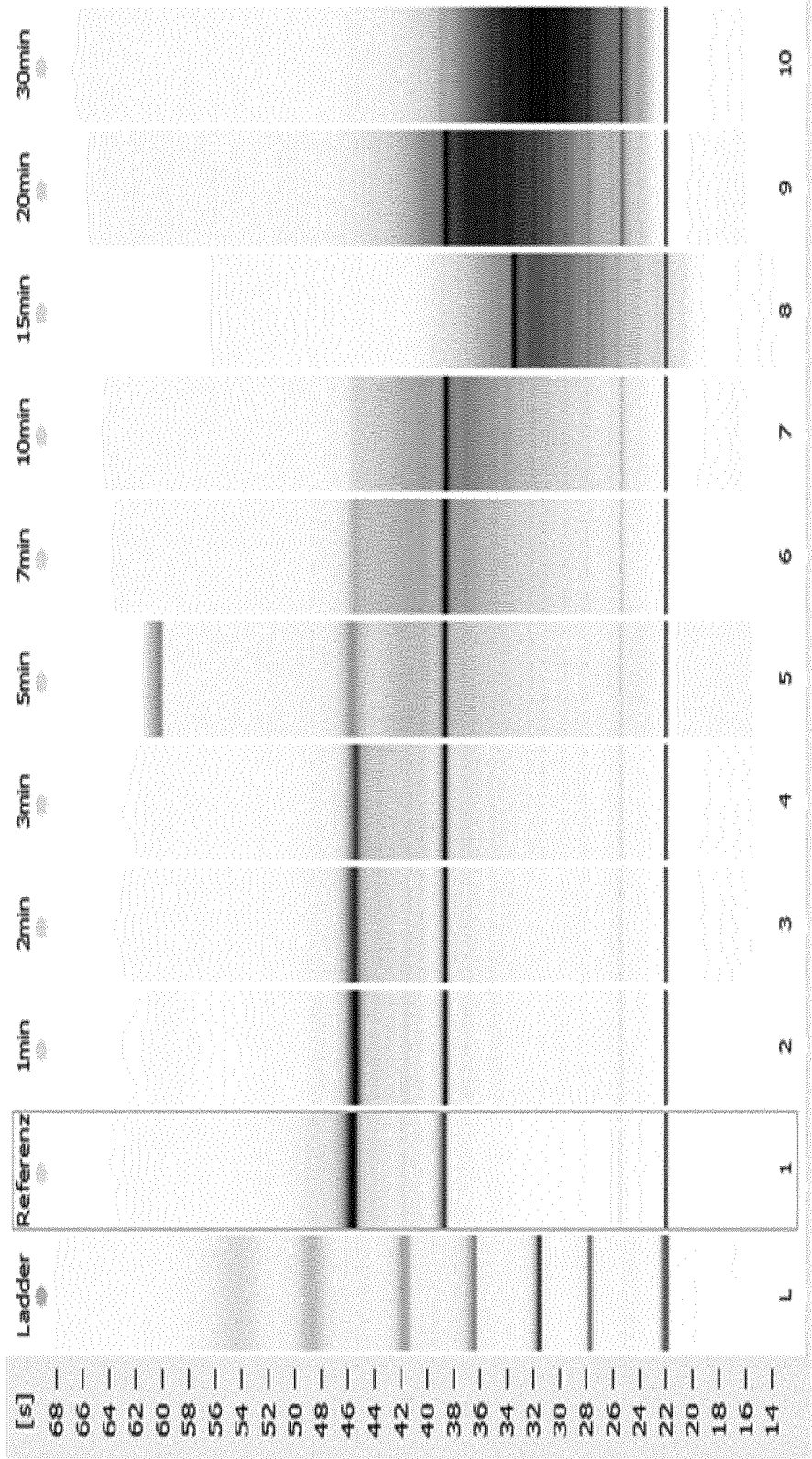
Figure 13C:
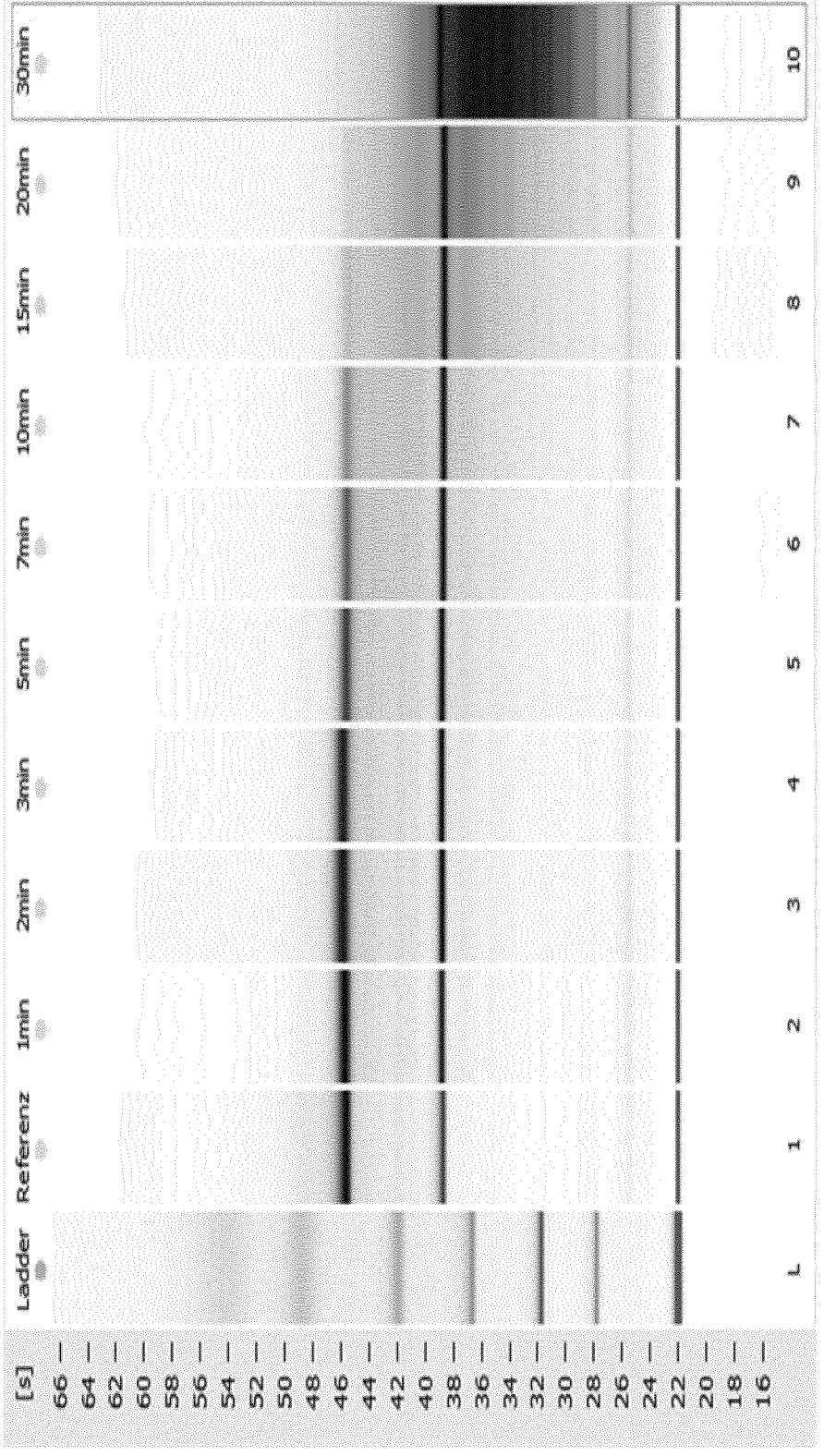
Figure 13D:
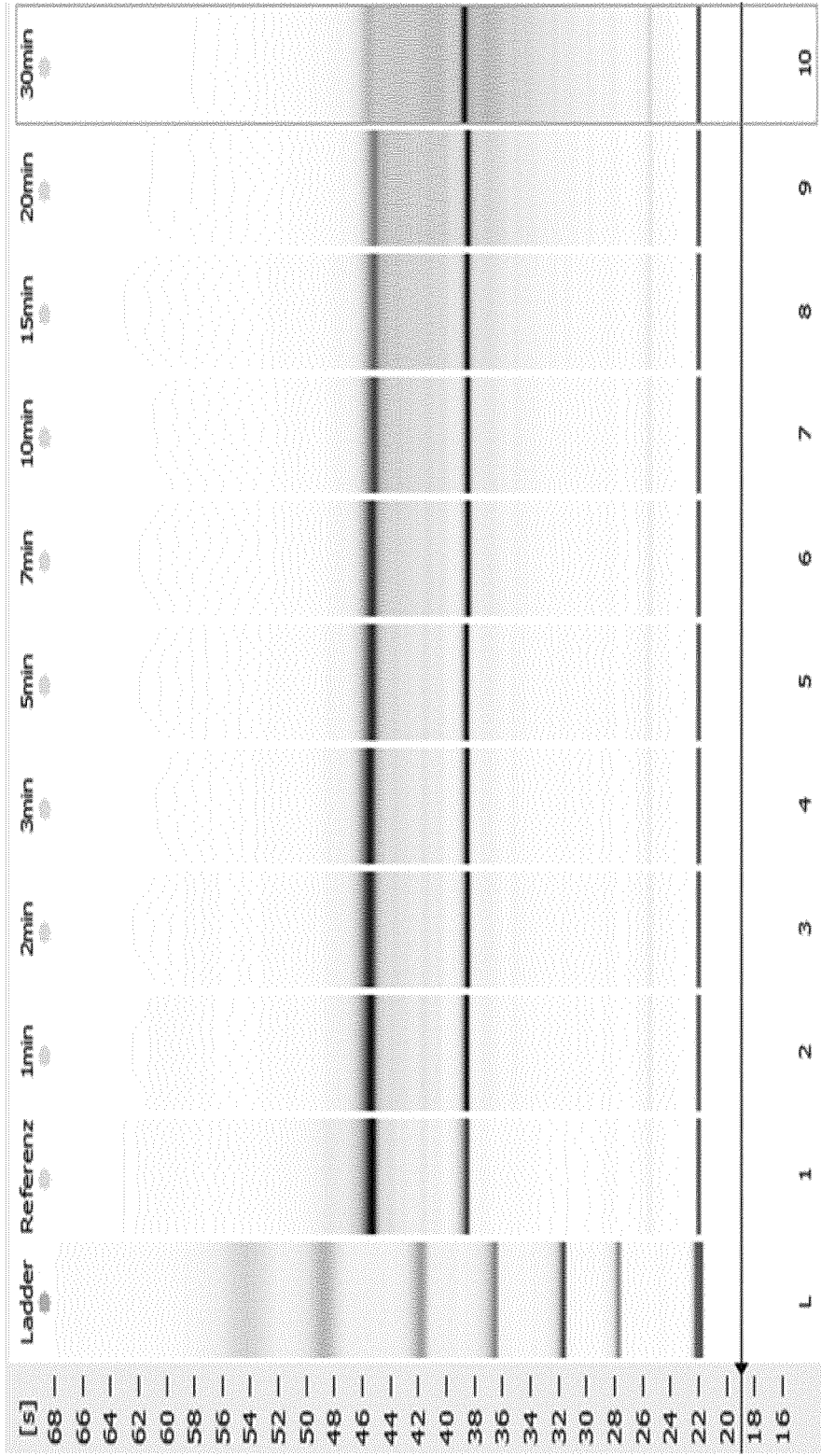
Figure 14A:
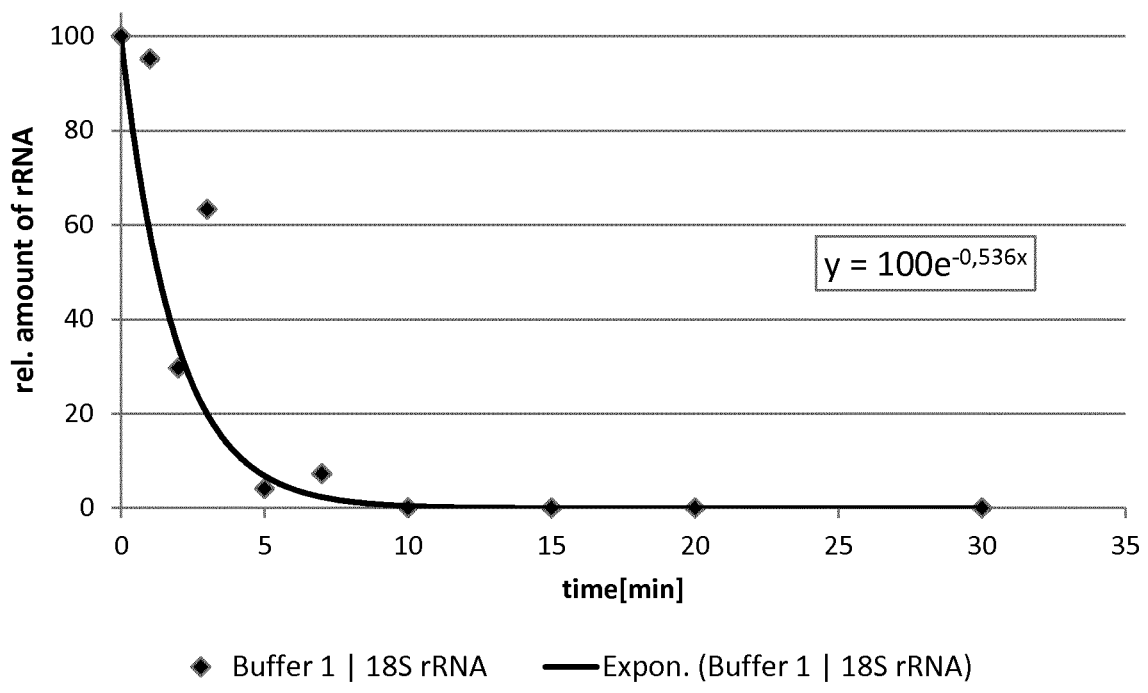
FIGS. 14A to 14D show the relative amount of 18S rRNA vs. incubation time for Buffers 1 to 4 tested in Example 4, respectively. The y-axis indicates the relative amount of full-length 18S rRNA (%); the x-axis indicates the incubation time.
Figure 14B:
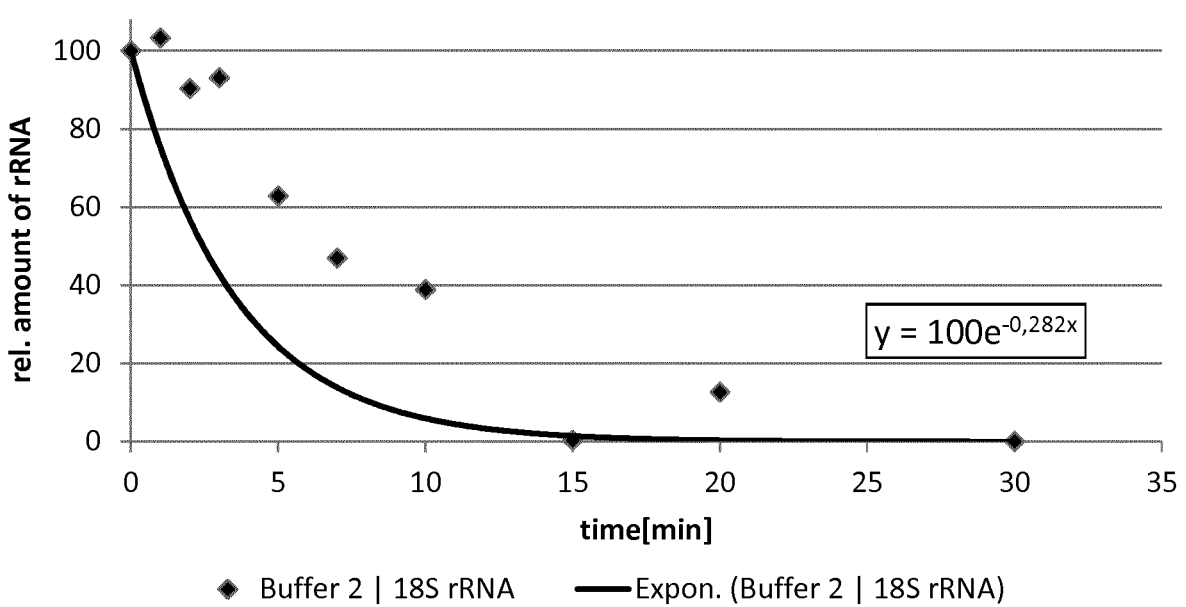
Figure 14C:
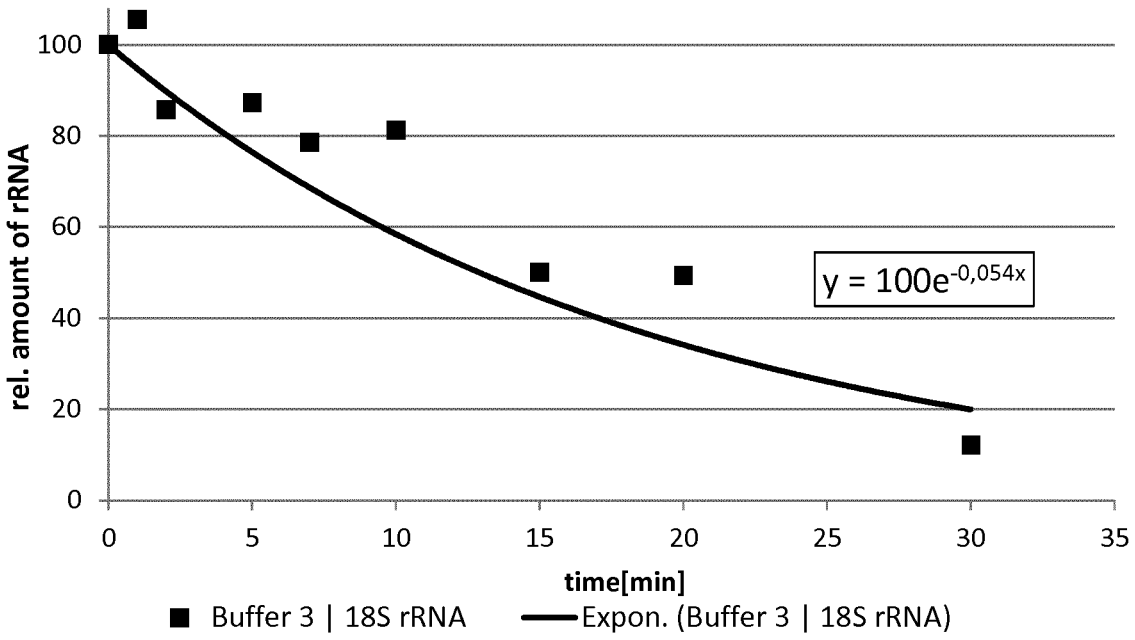
Figure 14D:
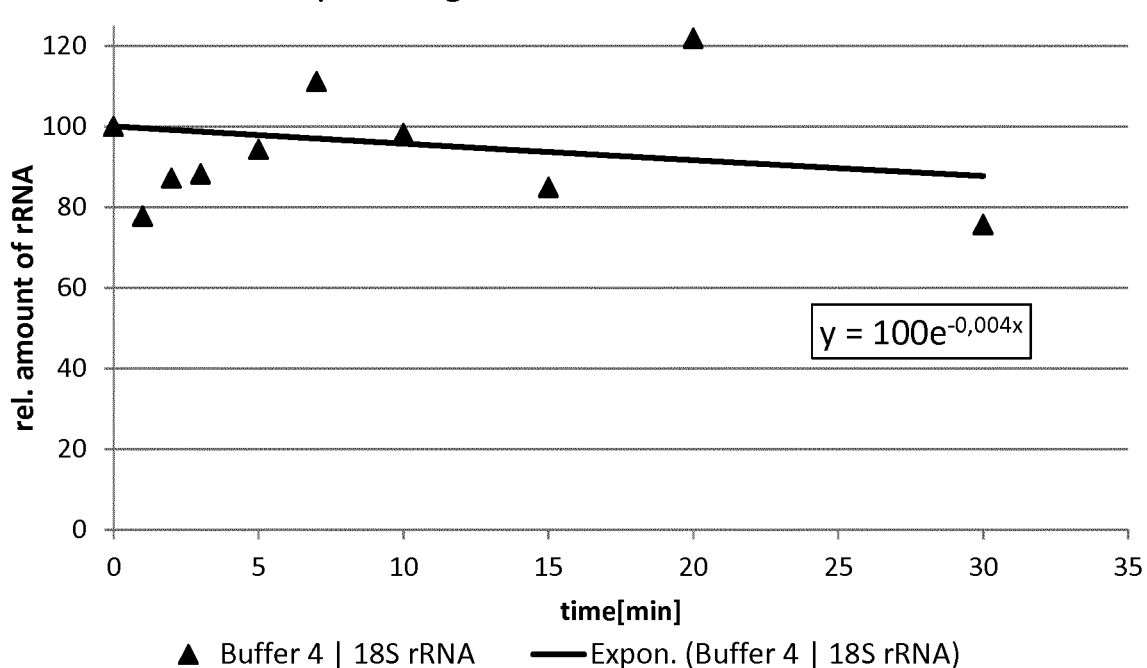
Figure 15A:
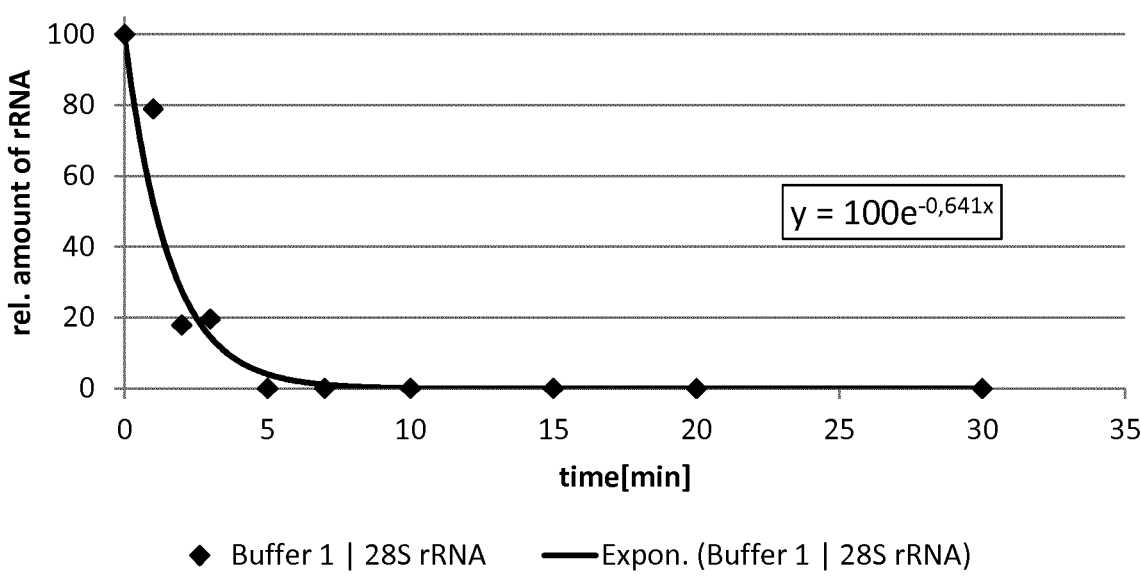
FIGS. 15A to 15D show the relative amount of 28S rRNA vs. incubation time for Buffers 1 to 4 tested in Example 4, respectively. The y-axis indicates the relative amount of full-length 28S rRNA (%); the x-axis indicates the incubation time.
Figure 15B:
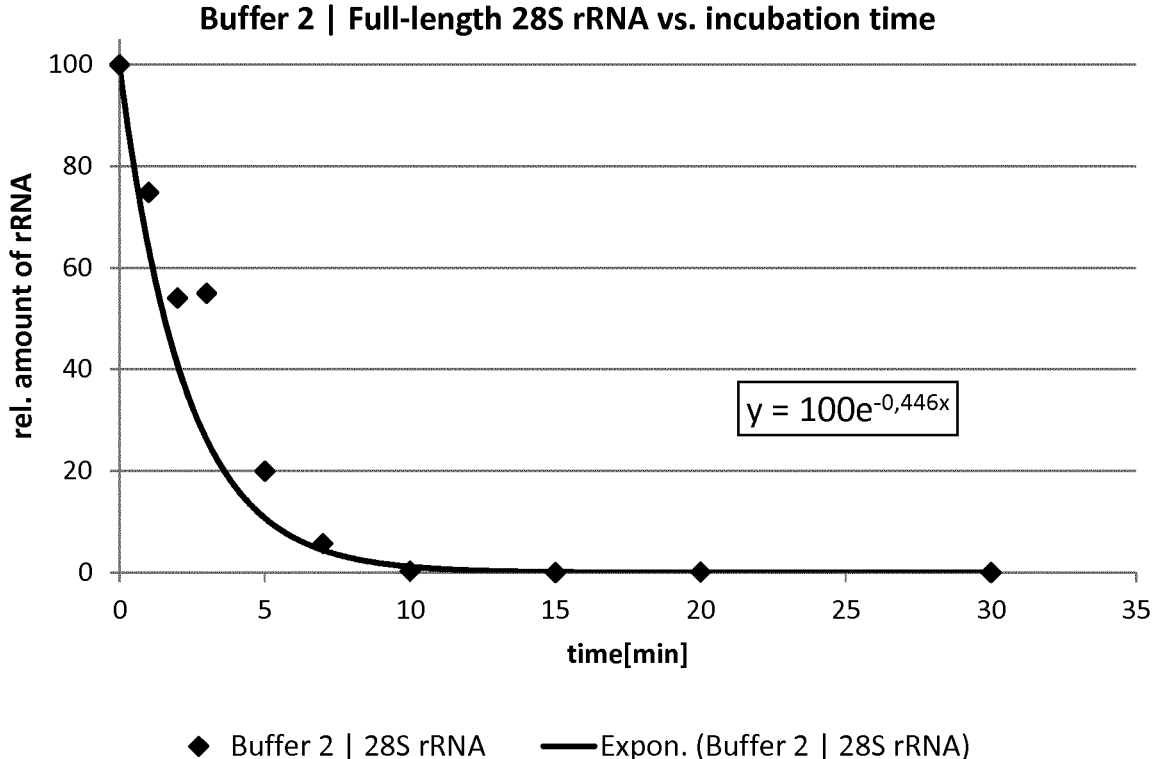
Figure 15C:
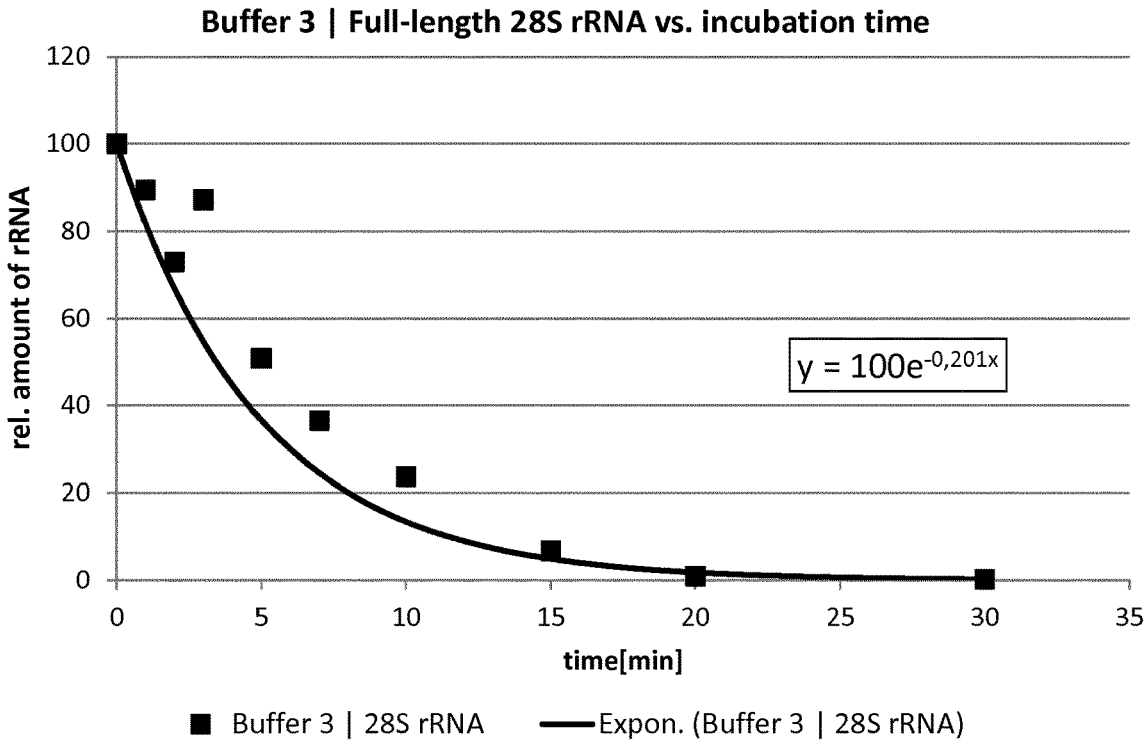
Figure 15D:
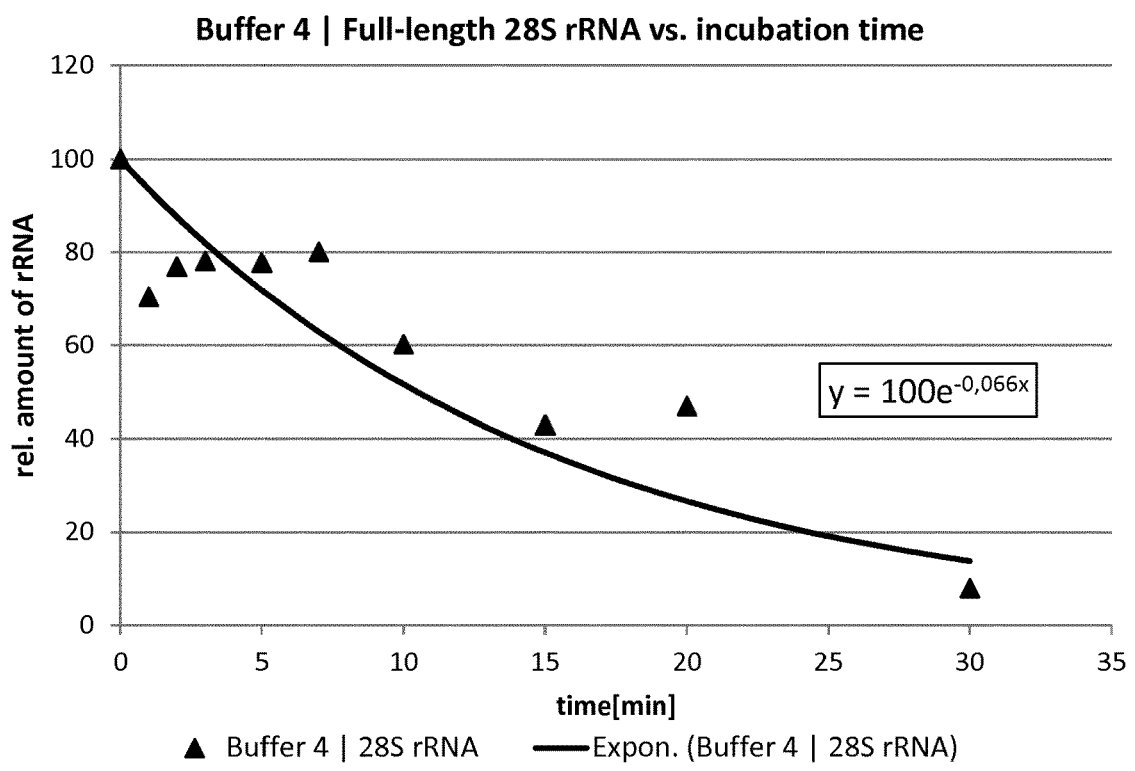
Figure 16A:
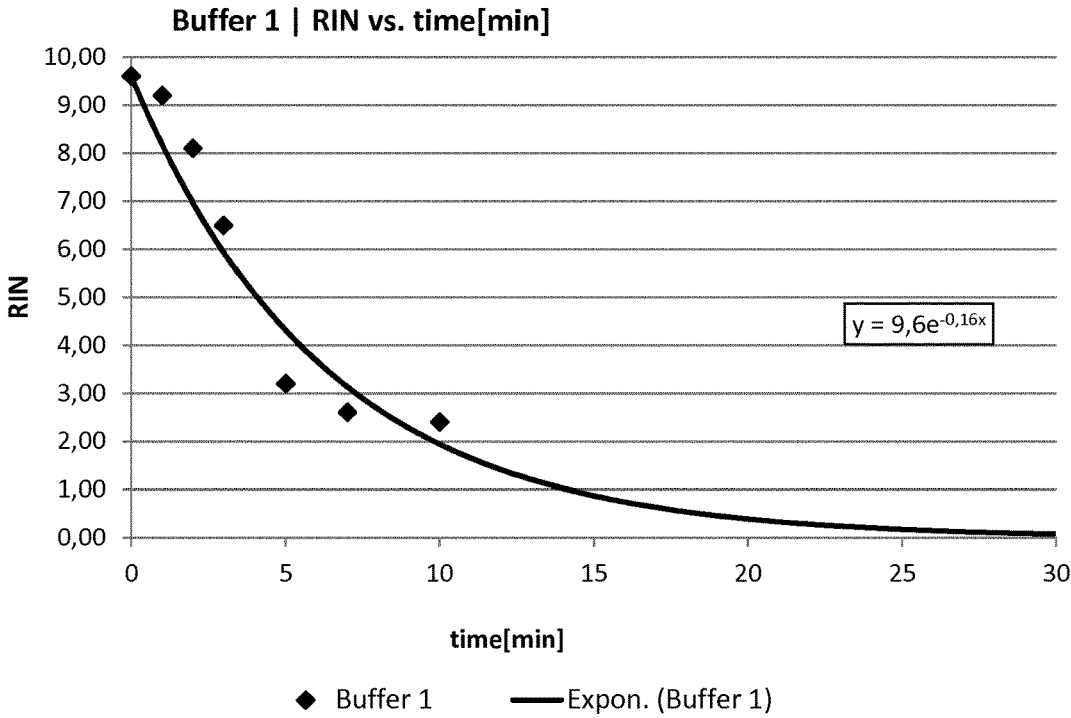
FIGS. 16A to 16D show the RIN vs. time for Buffers 1 to 4 tested in Example 4, respectively. RIN values are shown on the y-axis, incubation time on the x-axis.
Figure 16B:
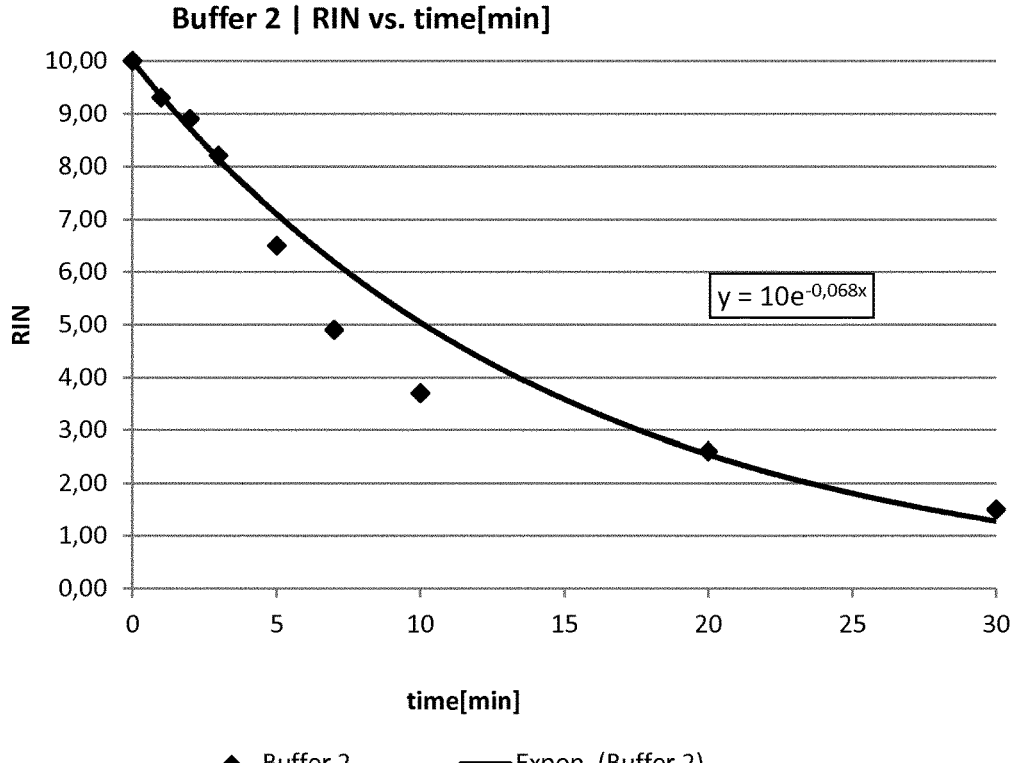
Figure 16C:
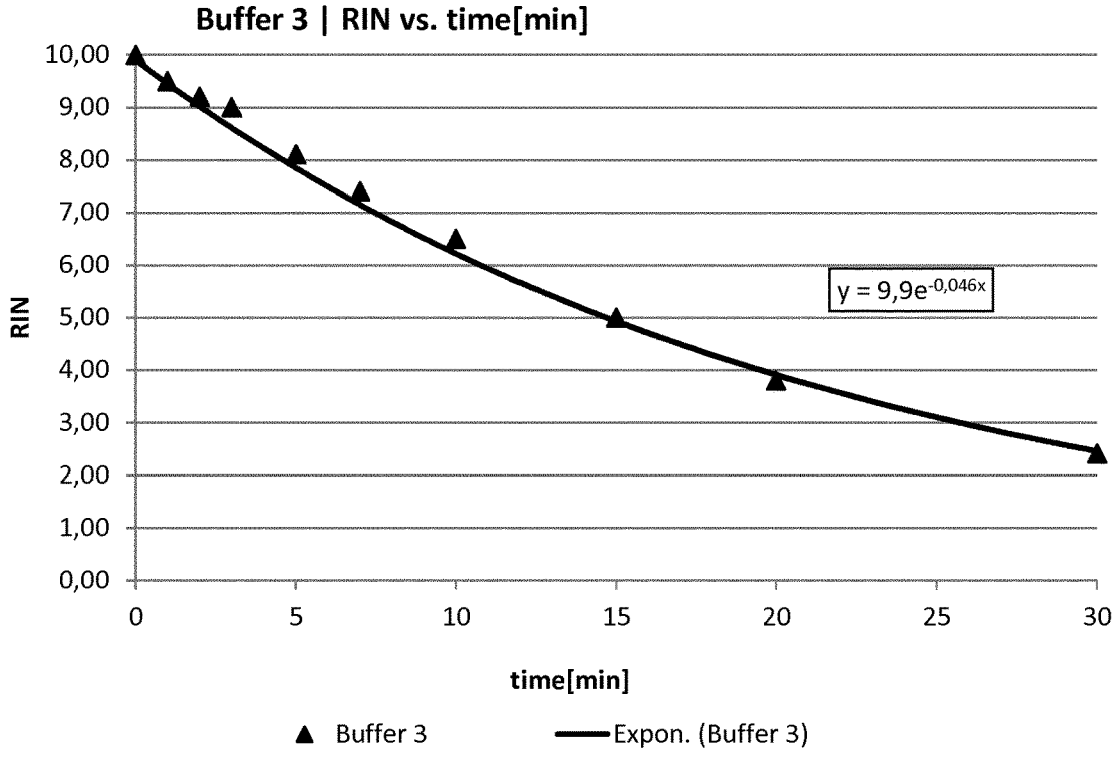
Figure 16D:
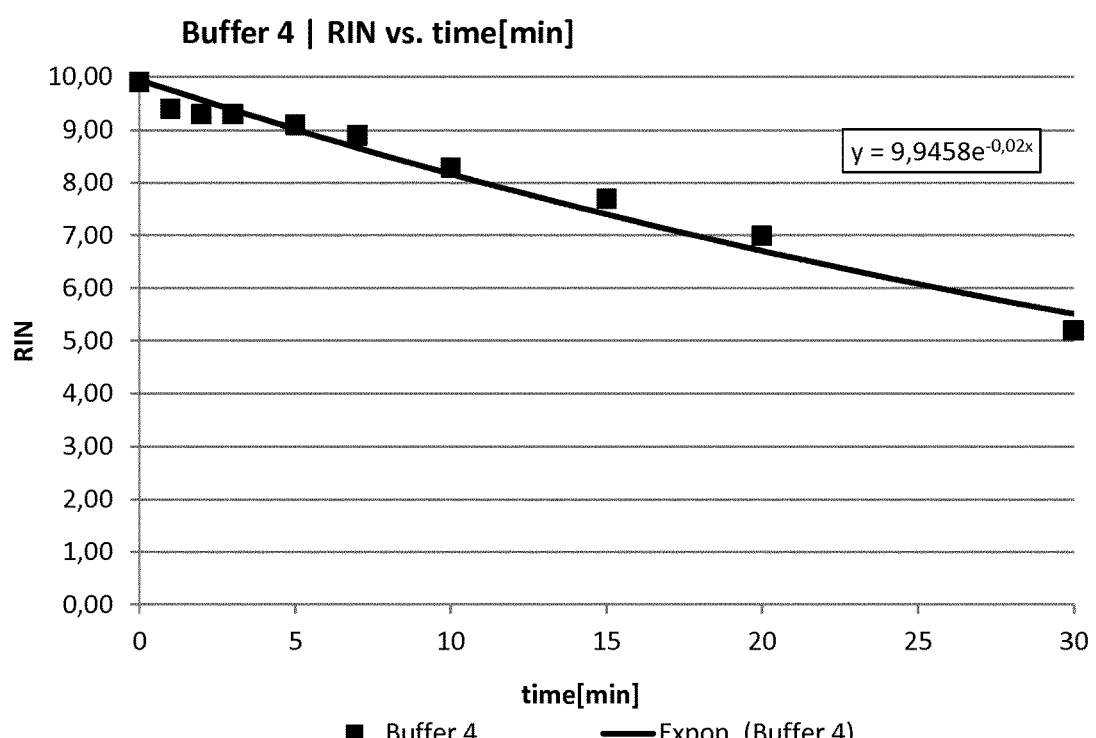

*BHQ = "black hole quencher"-a dark FRET acceptor dye that quenches the fluorescence of the FRET donor dye in the intact probe oligonucleotide Results 1: Agilent BioAnalyzer Gel Images FIGS. 13A to 13D show Agilent BioAnalyzer images (gel-like images) of human total RNA incubated at 85° C., pH 11, with the different buffer solutions. FIG. 13A is a gel-like image of RNA incubated with 20 mM NaOH, buffered to pH 11 (Buffer 1); FIG. 13B is a gel-like image of RNA incubated with 20 mM NaOH, buffered to pH 11, plus 0.01 mM (10 μM) EDTA (Buffer 2); FIG. 13C is a gel-like image of RNA incubated with 20 mM NaOH buffered to pH 11, plus 0.01 mM (10 μM) EDTA, plus 1 mM $(NH_4)_2SO_4$ (Buffer 3); FIG. 13D is a gel-like image of RNA incubated with 20 mM NaOH buffered to pH 11, plus 0.01 mM (10 μM) EDTA, plus 2.5 mM $(NH_4)_2SO_4$ (Buffer 4). For each of FIGS. 13A to 13D, the y axis shows the size of the RNA, here expressed as time required to pass through the gel chip. Each figure shows the ladder (L) as well as samples 1-10, wherein the samples are as indicated below:

| Sample 1: | (t = 0); Reference RNA |
|-----------|------------------------|
| Sample 2: | 1 min |
| Sample 3: | 2 min |
| Sample 4: | 3 min |
| Sample 5: | 5 min |
| Sample 6: | 7 min |
| Sample 7: | 10 min |
| Sample 8: | 15 min |
| Sample 9: | 20 min |
| Sample 10: | 30 min |

As can be seen from FIGS. 13A to 13D, rapid RNA degradation occurs in Buffer 1 (FIG. 13A), which neither comprises EDTA nor $(NH_4)_2SO_4$. The chelating agent EDTA alone (Buffer 2, FIG. 13B) at the concentration tested has a slight stabilizing effect. Significant RNA stabilization is achieved with Buffers 3 and 4, which comprise both, $(NH_4)_2SO_4$ and EDTA. As can be seen from a comparison of FIGS. 13C and 13D, with $(NH_4)_2SO_4$, 18S rRNA bands are visible for all incubation times tested. The amount of intact 28S rRNA after prolonged incubation can further be increased by increasing the $(NH_4)_2SO_4$ concentration from 1 mM (Buffer 3) to 2.5 mM (Buffer 4). As can be seen, the stabilizing effect of $(NH_4)_2SO_4$ alone (discussed above, Example 3), surprisingly is even more pronounced if $(NH_4)_2SO_4$ is used in combination with a chelating agent such as EDTA.

Results 2: Quantification of Full-Length rRNA:

Using the Agilent BioAnalyzer software, the relative amount of full-length 18S and 28S rRNA was quantified based on the intensity of the respective bands in the Bio-Analyzer Chip. The amount at time point "0" was set to 100%.

The 18S rRNA detected based on band intensity (% of 18S rRNA at time point 0) in the different buffers is shown in Table 12:

TABLE 12

| Sample [min] | Buffer 1 \| 18S rRNA | Buffer 2 \| 18S rRNA | Buffer 3 \| 18S rRNA | Buffer 4 \| 18S rRNA |
|--------------|----------------------|----------------------|----------------------|----------------------|
| 0 | 100 | 100 | 100 | 100 |
| 1 | 95 | 103 | 106 | 78 |
| 2 | 30 | 90 | 86 | 87 |
| 3 | 63 | 93 | 111 | 88 |
| 5 | 4 | 63 | 87 | 94 |
| 7 | 7 | 47 | 79 | 111 |
| 10 | 0 | 39 | 81 | 98 |
| 15 | 0 | 0 | 50 | 85 |
| 20 | 0 | 13 | 49 | 122 |
| 30 | 0 | 0 | 12 | 76 |

As shown in Table 12, EDTA alone (Buffer 2) has a slight effect on the % 18S rRNA detectable. The % of detectable RNA tends to be slightly increased compared to control Buffer 1. Buffers 3 and 4 yield excellent results and confer good stabilization of the RNA compared to control Buffer 1. In particular Buffer 4 achieves a high degree of stabilization also after prolonged incubation of 5 minutes, 7 minutes, and even after 30 minutes.

The data obtained and shown in Table 12 was analyzed by fitting a first-order decay curve (amount of rRNA vs. incubation time) and determining the half-lives of the full-length rRNA. The resulting curves for Buffers 1 to 4 are shown in FIGS. 14A to 14D, respectively. For each Figure, the y-axis indicates the relative amount of full-length 18S rRNA (%); the x-axis indicates the incubation time.

The 28S rRNA detected based on band intensity (% of 28S rRNA at time point 0) in the different buffers is shown in Table 13:

TABLE 13

| Sample [min] | Buffer 1 \| 28S rRNA | Buffer 2 \| 28S rRNA | Buffer 3 \| 28S rRNA | Buffer 4 \| 28S rRNA |
|--------------|----------------------|----------------------|----------------------|----------------------|
| 0 | 100 | 100 | 100 | 100 |
| 1 | 79 | 75 | 89 | 70 |
| 2 | 18 | 54 | 73 | 77 |
| 3 | 20 | 55 | 87 | 78 |
| 5 | 0 | 20 | 51 | 78 |
| 7 | 0 | 6 | 36 | 80 |
| 10 | 0 | 0 | 24 | 60 |
| 15 | 0 | 0 | 7 | 43 |
| 20 | 0 | 0 | 1 | 47 |
| 30 | 0 | 0 | 0 | 8 |

As can be seen from Table 13, also when the stabilization of the longer 28S rRNA is analyzed, Buffers 3 and 4 are clearly superior and retain a higher % of 28 S rRNA than control Buffer 1. This effect is particularly pronounced for incubation times of 5 minutes or more, and even stronger for Buffer 4 than for Buffer 3.

The data obtained and shown in Table 13 was analyzed by fitting a first-order decay curve (amount of rRNA vs. incubation time) and determining the half-lives of the full-length rRNA. The resulting curves for Buffers 1 to 4 are shown in FIGS. 15A to 15D, respectively. For each Figure, the y-axis indicates the relative amount of full-length 28S rRNA (%); the x-axis indicates the incubation time.

RNA half-lives were calculated as follows:

It was assumed that the full-length RNA degrades according to a first-order kinetics, hence the measured relative amount of RNA vs. time can be expressed as:

$$y = x_0 \cdot e^{-k \cdot t}$$

with y=amount of RNA at time x $x_0$=amount of RNA at time point 0 (here set to 100%—see above)

k=kinetic constant t=time [min]

The half-life t($\frac{1}{2}$) can be calculated from the kinetic constant k: t($\frac{1}{2}$)=ln(2)/k.

The results are shown in Table 14 below.

TABLE 14

| Buffer | rRNA half-life [min] ǀ 18S | Fold increase in half-life (18S)* | rRNA half-life [min] ǀ 28S | Fold increase in half-life (28S)* |
|---|---|---|---|---|
| 1 | 1.3 | — | 1.3 | — |
| 2 | 2.5 | 1.9 | 1.6 | 1.2 |
| 3 | 13 | 9.8 | 3.4 | 2.6 |
| 4 | 173 | 133 | 11 | 8.1 |

*compared to buffer 1 (=unstabilized RNA)

As can be seen from Table 14, the use of the chelating agent EDTA alone (Buffer 2) leads to a slight increase for 18S and 28S rRNA half-life as compared to control Buffer 1. Buffers 3 and 4, which both comprise $(NH_4)_2SO_4$, results in a pronounced increase in 18S and 28S rRNA half-life. Surprisingly, while even as little as 1 mM $(NH_4)_2SO_4$ in Buffer 3 was sufficient to result in a considerable increase in RNA half-life, the increase in 18S rRNA was about 13-fold higher for Buffer 4 (comprising only slightly more $(NH_4)_2$ $SO_4$, 2.5 mM) as compared to Buffer 3.

Overall, it can be seen that 18S rRNA and 28S rRNA degrade rapidly when incubated at 85° C. and pH 11 (Buffer 1).

Addition of 10 µM EDTA (Buffer 2) has a stabilizing effect on the full-length rRNAs but the increase in half life is only modest. In contrast, the additional presence of 1 mM ammonium sulfate leads to a strong stabilizing effect of almost 10-fold increase in half-life for the 18S RNA and more than 2-fold increase in half-life for the 28S rRNA. Addition of 2.5 mM ammonium sulfate in the presence of 10 µM EDTA lead to an even stronger stabilization, with a more than 100-fold increase in half-life for the 18S rRNA and an 8-fold increase for the 28S rRNA compared to the control. This is remarkable and unexpected as only a single hydrolysis event affecting a phosphodiester bond in the long rRNA molecules would destroy the full-length RNA.

Results 3: Agilent BioAnalyzer RIN Value Analysis

Further, the RIN values obtained from the Agilent Bio-Analyzer were analyzed vs. incubation time to determine the RIN "half-life". The "RIN half-life" is the time required for the RIN to drop from 10 (fully intact, high-quality RNA) to 5 (lowest RIN for an RNA sample to be still suitable for qPCR-based analysis). RIN half-lives were calculated by assuming that the change of RIN is a function of incubation time follows a first-order kinetics.

FIGS. 16 A to 16 D show the RIN vs. time for Buffers 1 to 4, respectively. RIN values are shown on the y-axis, incubation time on the x-axis. The results are shown in Table 15 below. The RIN half-life is increased with Buffers 2 to 4 as compared to control Buffer 1. Again, the best results are obtained with Buffer 4.

TABLE 15

| Buffer | RIN half-life [min] |
|---|---|
| 1 | 4 |
| 2 | 10 |
| 3 | 15 |
| 4 | 35 |

A similar result as above (see Results 2) is obtained when analyzing the RIN during the 30 min incubation in the different alkaline buffers: Here, the presence of 10 µM EDTA and 1 mM ammonium sulfate leads to a more than three-fold increase in the "RIN half-life" (Buffer 3), the presence of 2.5 mM ammonium sulfate with 10 µM EDTA leads to an 8-fold increase (Buffer 4). This indicates that a high-quality RNA preparation with a RIN of or near 10 can be incubated in an alkaline buffer of pH 11 and 85° C. for about 30 minutes when following the teachings of the present invention; after which the RNA is still considered intact enough for qPCR analysis.

Results 4: Quantitative Real-Time RT-PCR Analysis of 18S rRNA Targets

A qRT-PCR analysis of ribosomal 18S RNA was performed, using two different amplicons, 66 nt and 500 nt.

Figure 17A:
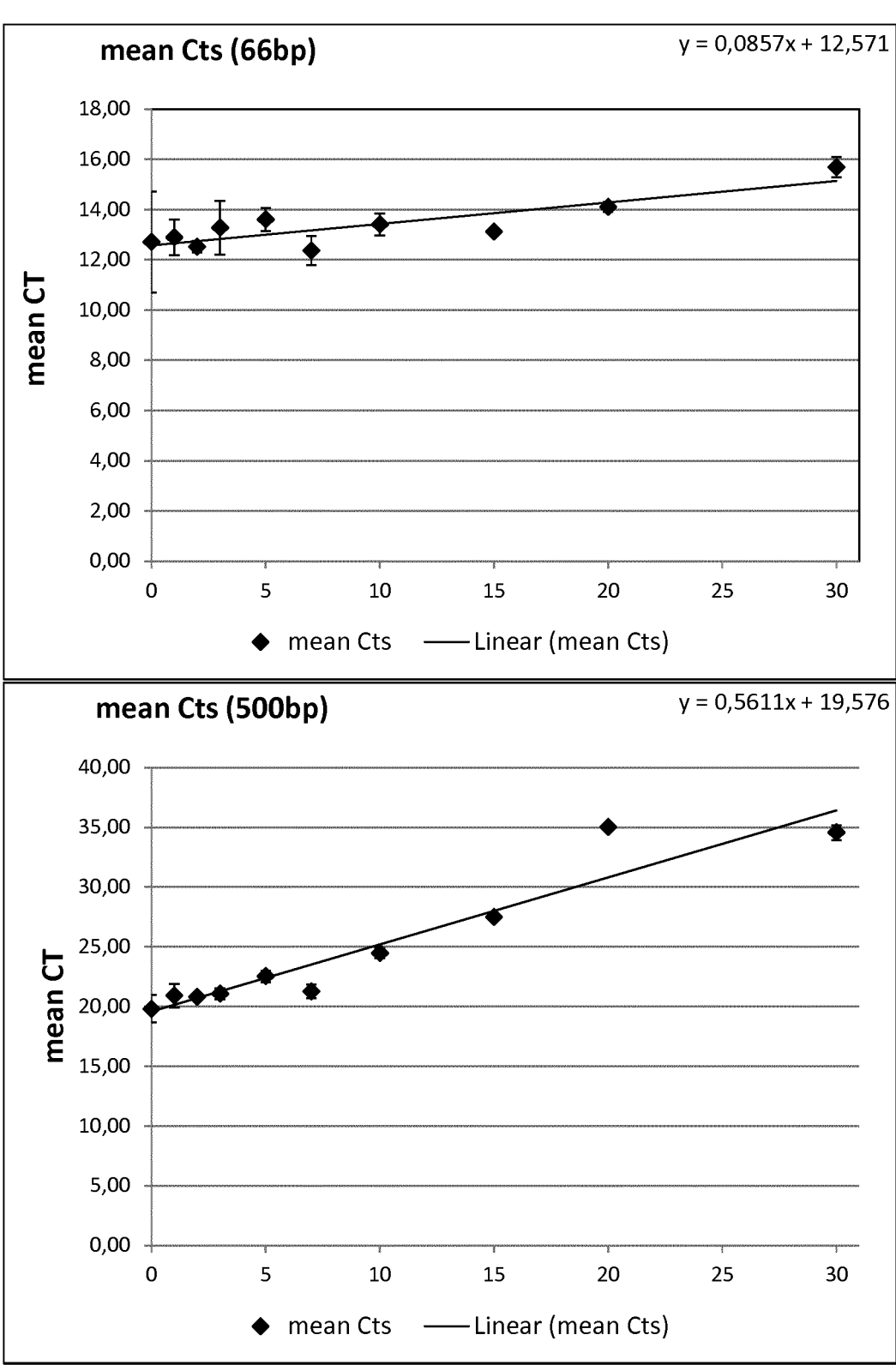
FIGS. 17A to 17D shown the mean Ct values for the 66 bp amplicon (upper panel) and for the 500 bp amplicon (lower panel) obtained with Buffers 1 to 4, respectively. The mean CT value is shown on the y-axis, the incubation time on the X-axis.
Figure 17B:
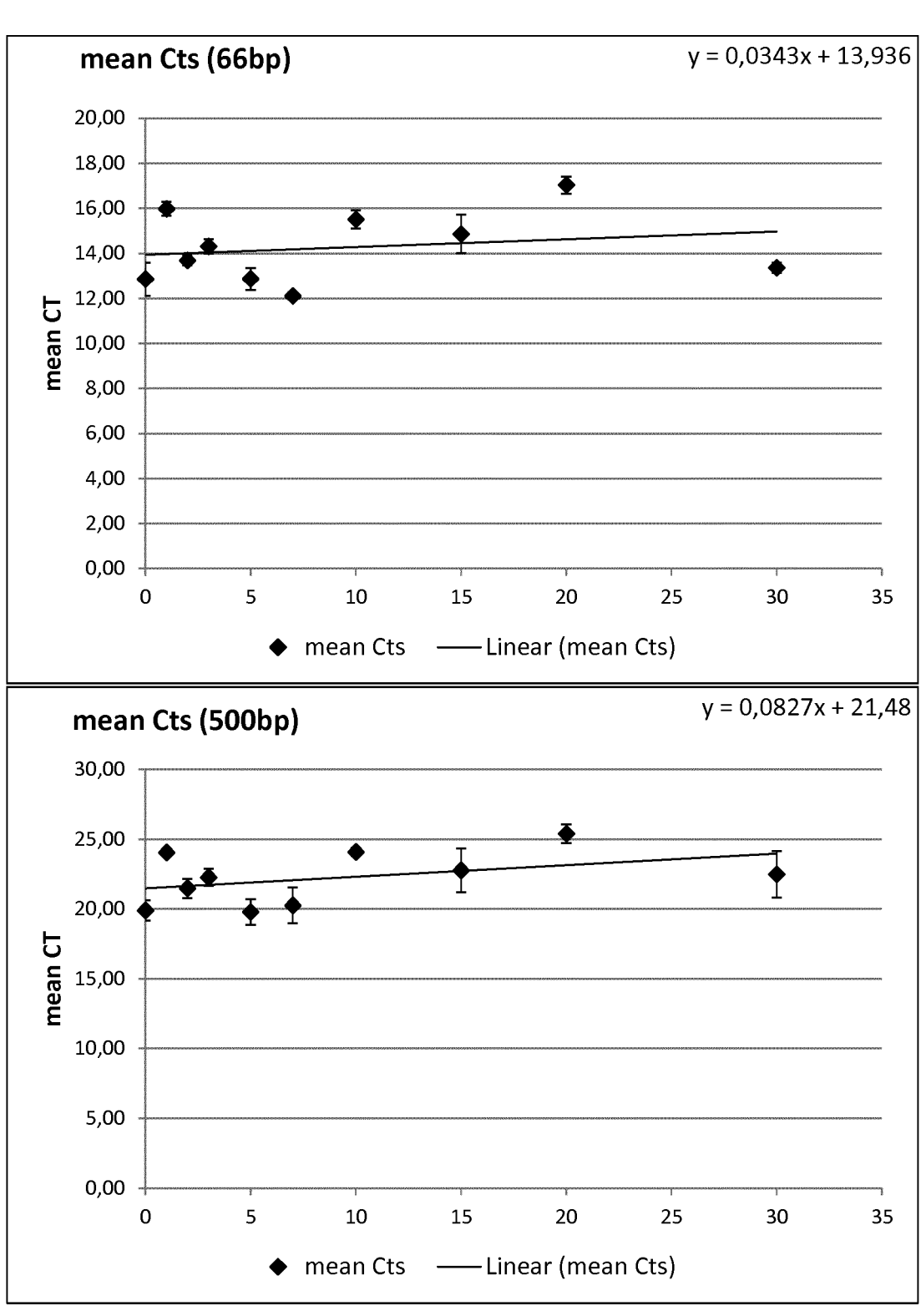
Figure 17C:
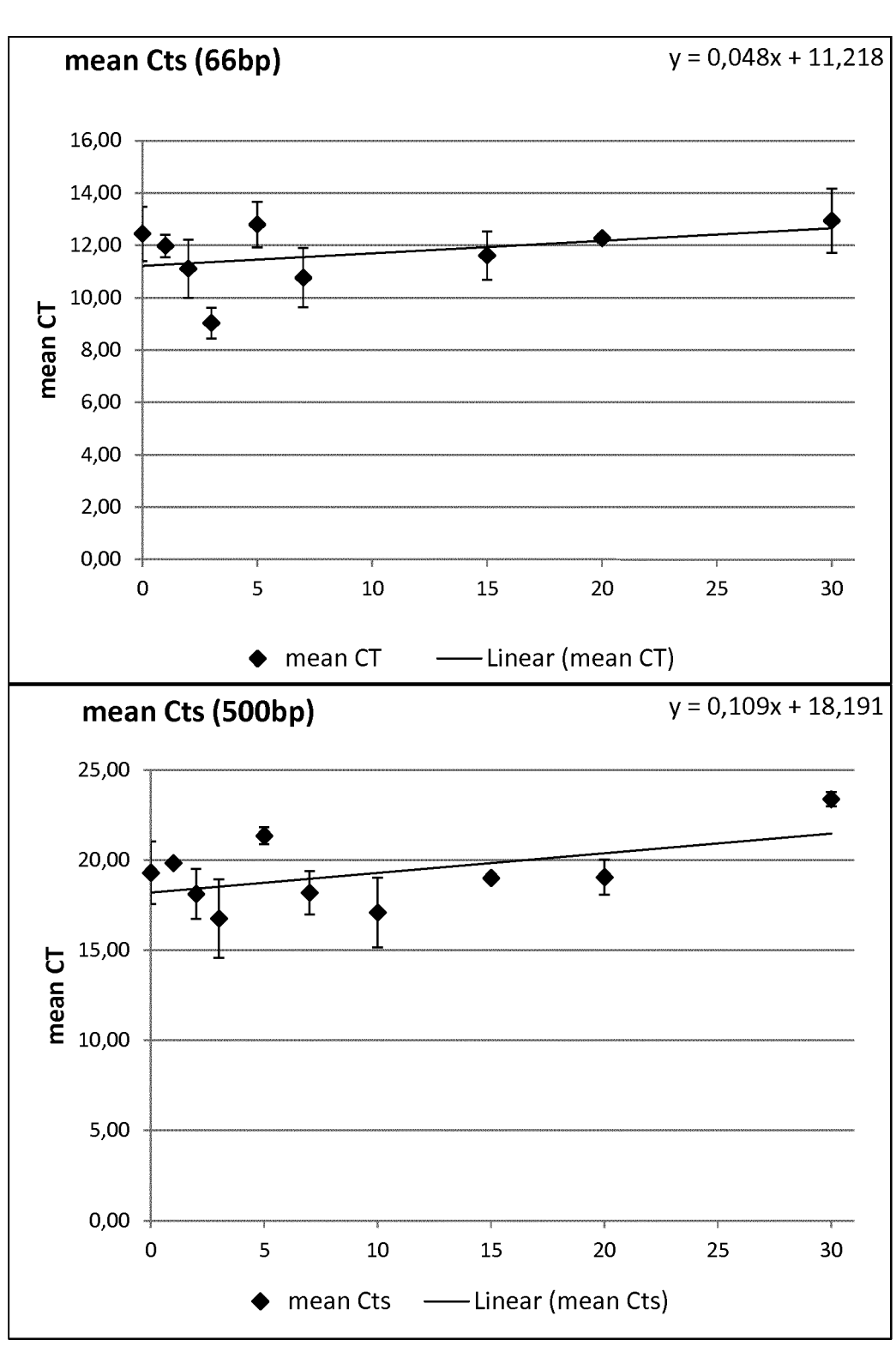
Figure 17D:
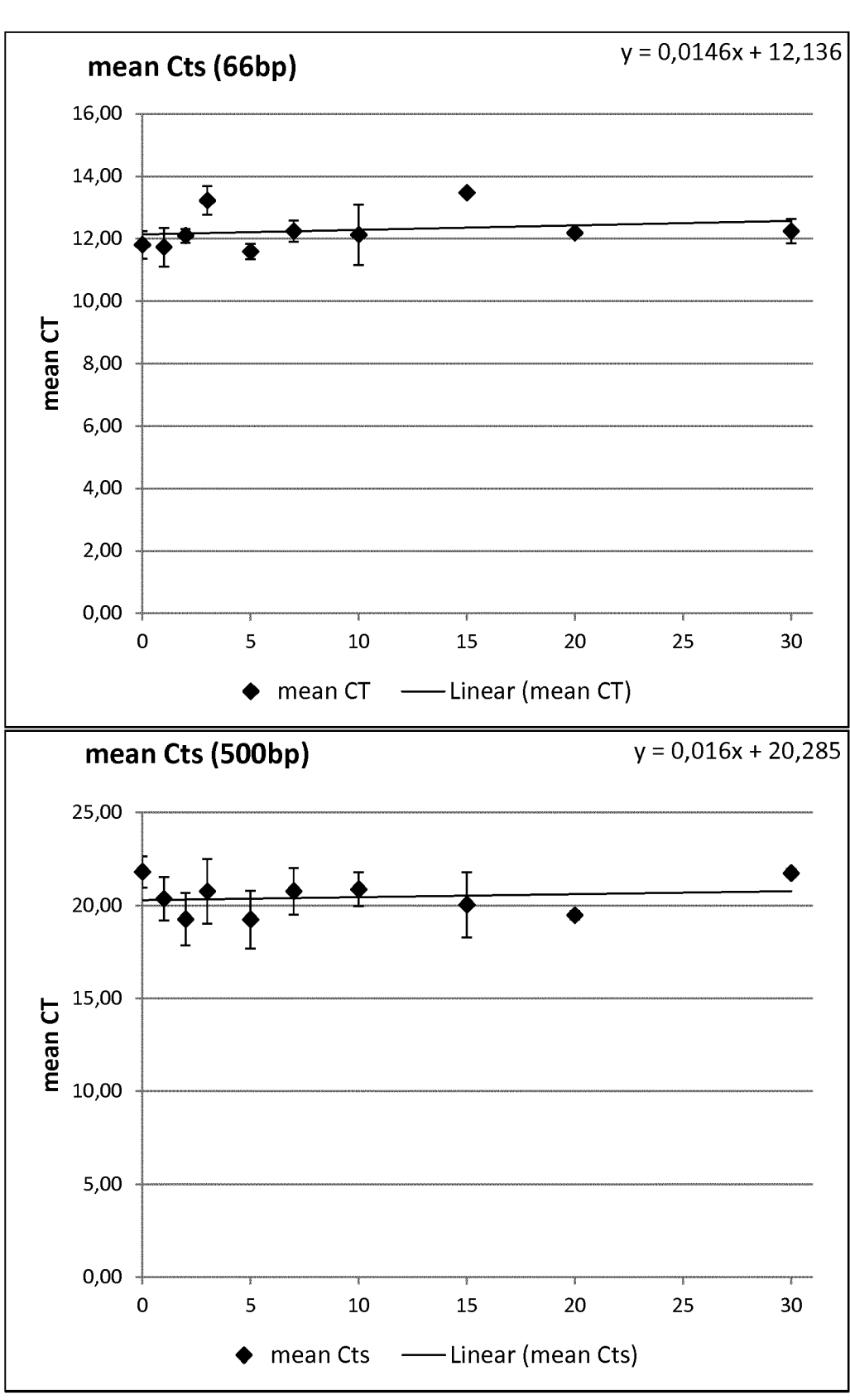

FIGS. 17A to 17D shown the mean Ct values for the 66 bp amplicon (upper panel) and for the 500 bp amplicon (lower panel) obtained with Buffers 1 to 4, respectively (results for Buffer 1 shown in FIG. 17A, for Buffer 2 shown in FIG. 17B, for Buffer 3 shown in FIG. 17C, and for Buffer 4 shown in FIG. 17D). The mean CT value is shown on the y-axis, the incubation time on the X-axis.

Calculation of RNA Half-Lives:

For the calculation of RNA half-life, it was assumed that an increase of the Ct value by 1 equals a 50% reduction of the amount of template (based on an ideal PCR with 100% efficiency).

$$y = x_0 + k \cdot t$$

with y=amount of RNA at time x (expressed as Ct value)

$x_0$=amount of RNA at time point 0 (expressed as Ct value)

k=slope of the fitted Ct vs. time curve t=time [min]

The half-life t($\frac{1}{2}$) can be calculated from the kinetic constant k: t($\frac{1}{2}$)=1/k.

The rRNA half-lifes for 66 bp and 500 bp amplicons are shown in Table 16.

TABLE 16

| Buffer | rRNA half-life [min] \| 66 bp | rRNA half-life [min] \| 500 bp |
|---|---|---|
| 1 | 12 | 2 |
| 2 | 29 | 12 |
| 3 | 21 | 9 |
| 4 | 69 | 63 |

When analyzing the 18S rRNA by qPCR, it is directly demonstrated that stabilizing the RNA in alkaline buffer and high temperature (in particular in the presence of 2.5 mM ammonium sulfate and 10 µM EDTA) leads to a very strong stabilization of amplifiable RNA. This effect is even more pronounced for a long 500 nt RNA target which is considered more susceptible to alkaline hydrolysis compared to a shorter amplicon (RNA sequence).

Example 5—RNA Stabilization by (NH$_4$)$_2$SO$_4$ and EDTA in Solution at pH 10 and 75° C.

Figure 18A:
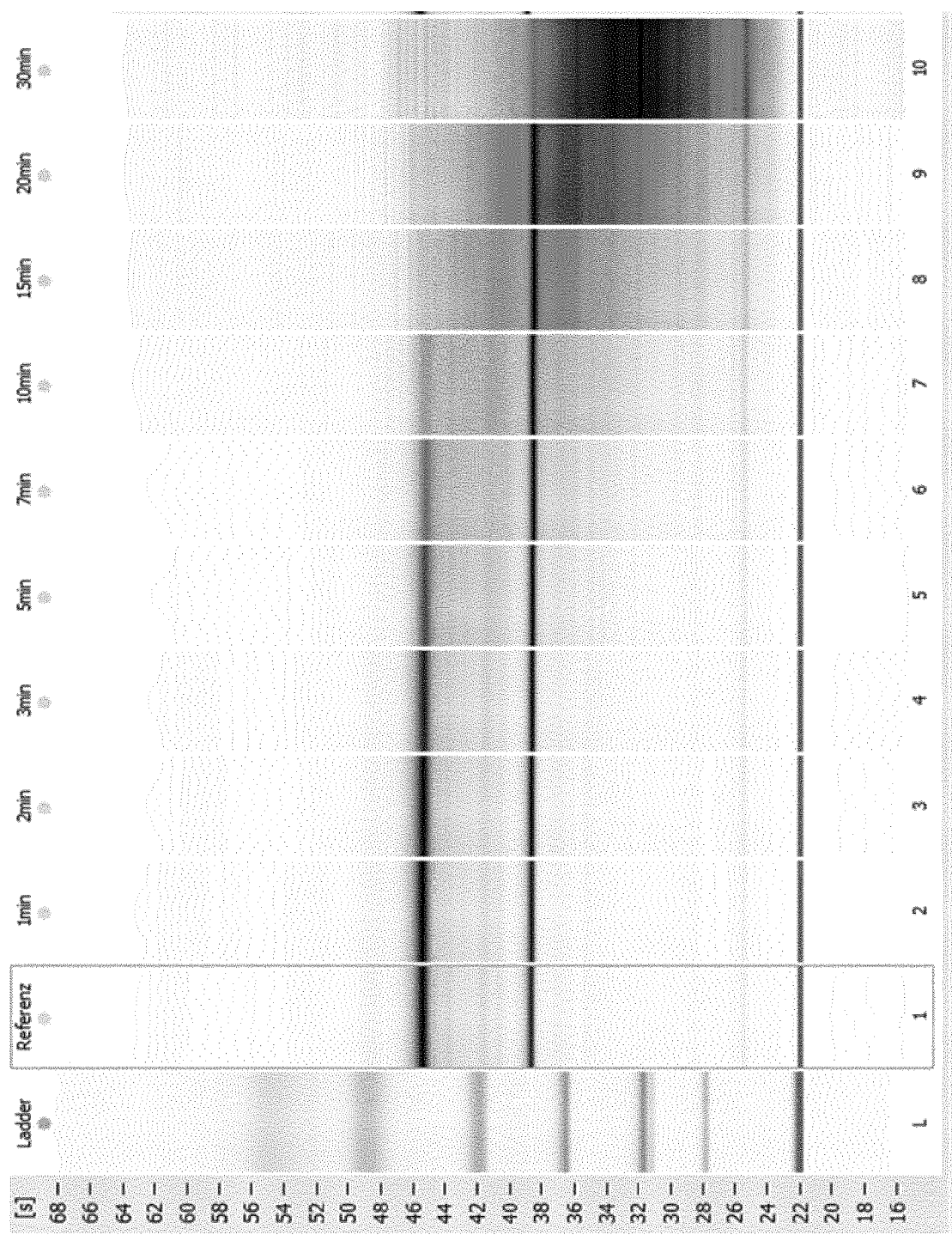
FIGS. 18A to 18C show Agilent BioAnalyzer images (gel-like images) of human total RNA incubated at 75° C., pH 10, with different solutions as further described in Example 5.
Figure 18B:
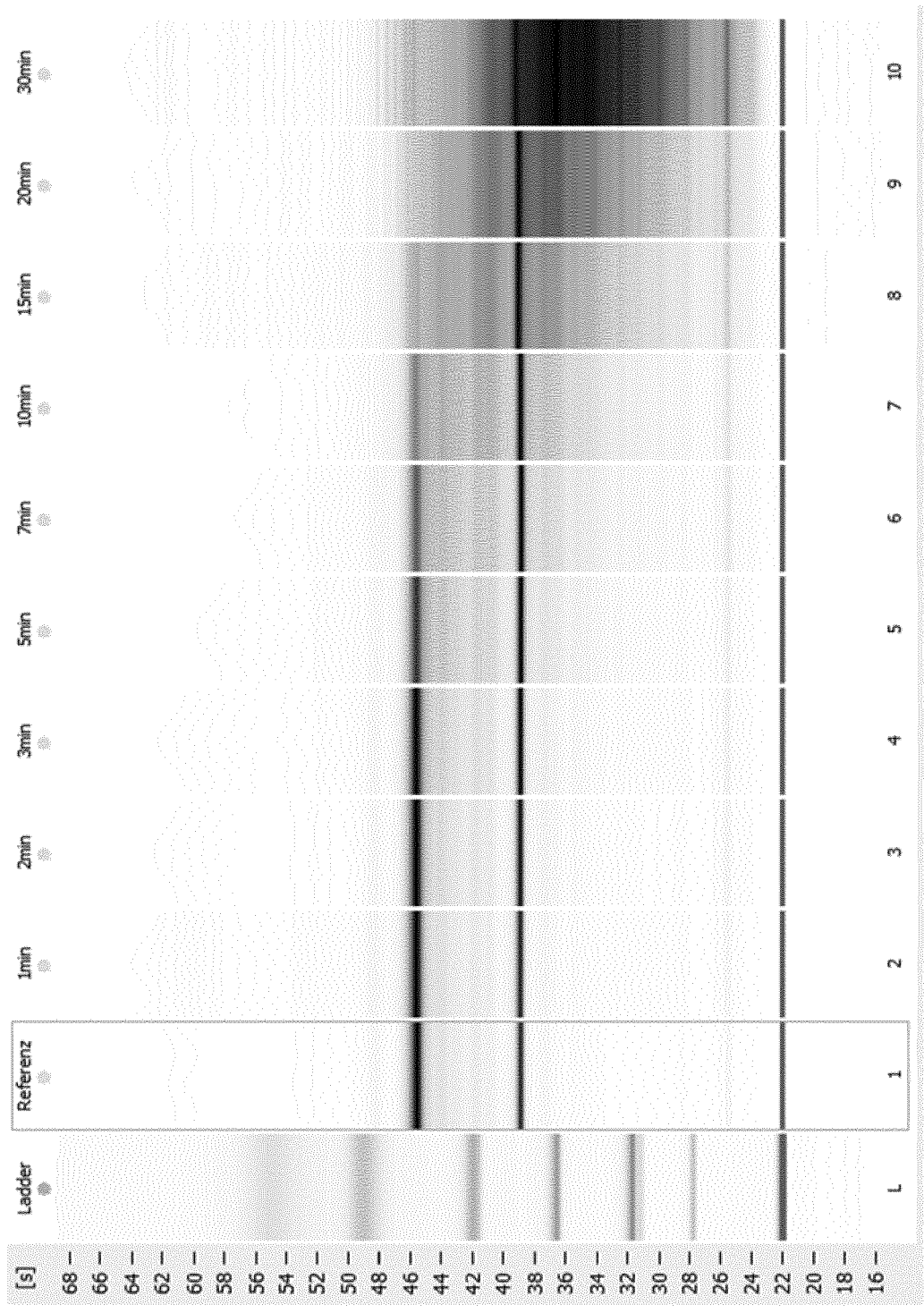
Figure 18C:
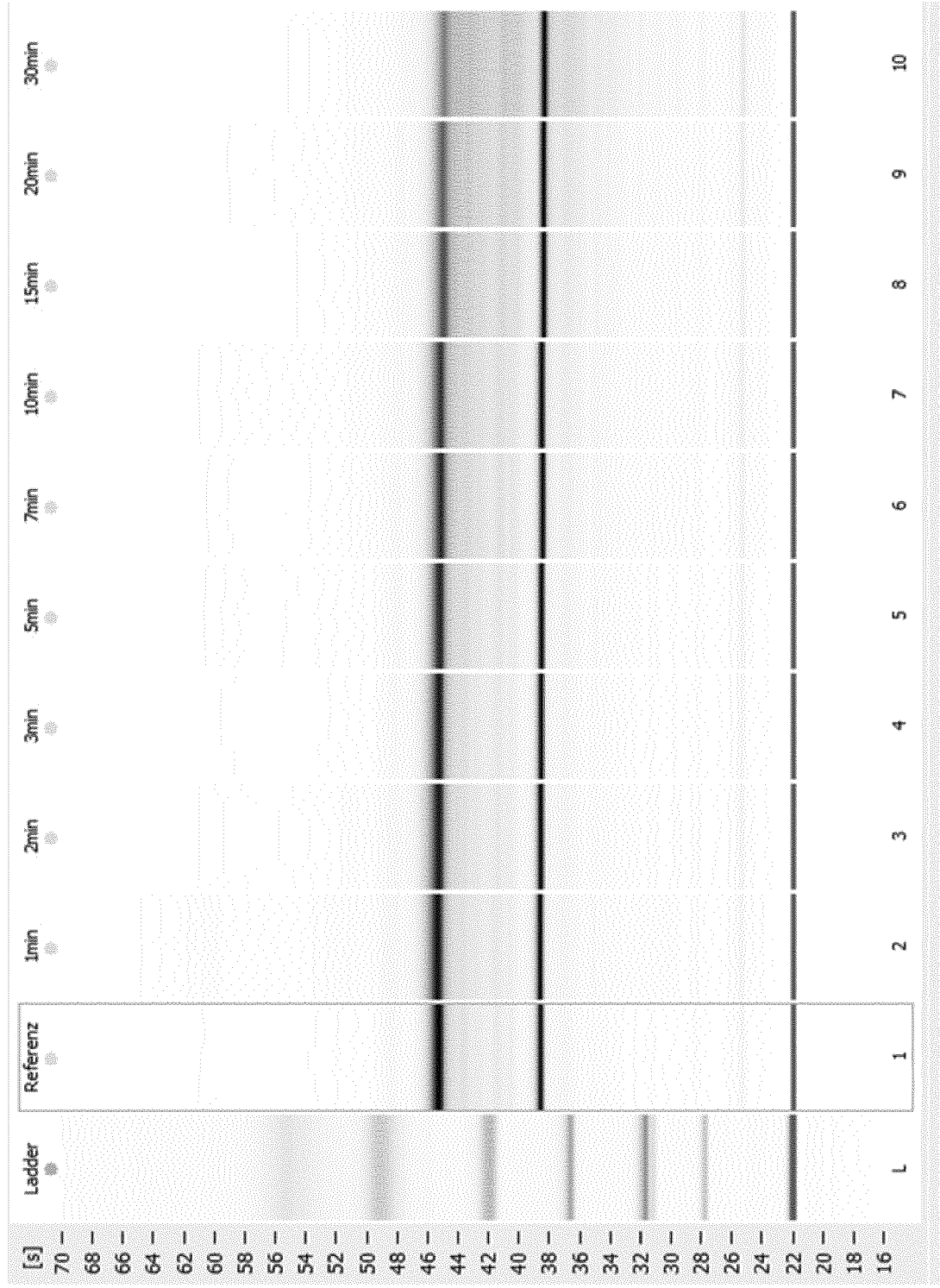

Study Design:
Human total RNA (RNeasy-extracted) was spiked into different buffers which are suitable as elution buffers.
Buffer conditions:
Buffer 1: 20 mM NaOH buffered to pH 10;
Buffer 2: 20 mM NaOH buffered to pH 10, plus 2.5 mM ammonium sulfate (NH$_4$)$_2$SO$_4$;
Buffer 3: 20 mM NaOH buffered to pH 10, plus 2.5 mM ammonium sulfate ((NH$_4$)$_2$SO$_4$), plus 1 mM EDTA.
800 ng RNA (1 µl) mixed with 19 µl buffer=start of incubation (total volume 20 µl).
At different time points, 2 µl RNA are removed and immediately added to 3 µl 100 mM NaOAc, pH 5, to stop the degradation process.
Time course of incubation: +1 min\|+2 min\|+3 min\|+5 min\|+7 min\|+10 min\|+15 min\|+20 min\|+30 min.
Incubation temperature: 75° C.
RNA samples (1 µl each) were run on an Agilent BioAnalyzer (RNA Pico Kit).
Analyzed RNA integrity (RIN) vs. incubation time.
Analyzed amount of remaining full-length 18S rRNA, 28S rRNA vs. incubation time based on the relative full-length band intensity. The amount of RNA at time point 0 was set to 100%. Calculated full-length rRNA half-lives.
Details of this Analysis of Remaining Full-Length 18S rRNA, 28S rRNA:
The quantity of full-length rRNA was determined by densitometric measurement of the intensity of the respective rRNA band on the Agilent Bioanalyzer gel chip. To this end, the relative RNA intensity was plotted against the time required for traveling through the gel capillary, where higher molecular weight (=longer) RNA molecules travel more slowly than shorter RNAs. The amount of the respective full-length RNA was determined by measuring the area under the respective RNA peak in the intensity vs. time trace. A set of defined marker RNA molecules was run alongside the samples with every capillary gel chip, such that the intensity of the RNA samples could be calibrated against the marker RNA. Then, the measured relative amount of full-length rRNA was plotted against the incubation time, with the rRNA amount at time point "0" being normalized to 100%; the rRNA half-life was determined by fitting a first-order degradation kinetics to the data.
Results 1: Agilent BioAnalyzer Gel Images FIGS. 18A to 18C show Agilent BioAnalyzer images (gel-like images) of human total RNA incubated at 75° C., pH 10, with different solutions as further described in Example 5. FIG. 18A is a gel-like image of RNA incubated with 20 mM NaOH, buffered to pH 10 (Buffer 1); FIG. 18B is a gel-like image of RNA incubated with 20 mM NaOH, buffered to pH 10, plus 2.5 mM (NH$_4$)$_2$SO$_4$ (Buffer 2); FIG. 18C is a gel-like image of RNA incubated with 20 mM NaOH buffered to pH 10, plus 2.5 mM (NH$_4$)$_2$SO$_4$, plus 1 mM EDTA, (Buffer 3).

For each of FIGS. 18A to 18C, the y axis shows the size of the RNA, here expressed as time required to pass through the gel chip. Each figure shows the ladder (L) as well as samples 1-10, wherein the samples are as indicated below:

| | |
|---|---|
| Sample 1: | (t = 0); Reference RNA |
| Sample 2: | 1 min |
| Sample 3: | 2 min |
| Sample 4: | 3 min |
| Sample 5: | 5 min |
| Sample 6: | 7 min |
| Sample 7: | 10 min |
| Sample 8: | 15 min |
| Sample 9: | 20 min |
| Sample 10: | 30 min |

Results 2: Quantification of Full-Length rRNA:

Using the Agilent BioAnalyzer software, the relative amount of full-length 18S and 28S rRNA was quantified based on the intensity of the respective bands in the Bio-Analyzer Chip. The amount at time point "0" was set to 100%.

The 18S rRNA detected based on band intensity (% of 18S rRNA at time point 0) in the different buffers is shown in Table 17:

TABLE 17

| Sample [min] | Buffer 1 \| 18S | Buffer 2 \| 18S | Buffer 3 \| 18S |
|---|---|---|---|
| 0 | 100 | 100 | 100 |
| 1 | 110 | 85 | 94 |
| 2 | 93 | 91 | 88 |
| 3 | 100 | 75 | 102 |
| 5 | 89 | 76 | 123 |
| 7 | 75 | 57 | 92 |
| 10 | 50 | 46 | 94 |
| 15 | 28 | 29 | 104 |
| 20 | 12 | 23 | 126 |
| 30 | 2 | 8 | 102 |

As can be seen, the stabilizing effect of (NH$_4$)$_2$SO$_4$ alone can be observed in particular at prolonged incubation times of 20 and 30 minutes (Buffer 2). Buffers 3 yields good stabilization, in particular at incubation times of 5 minutes and longer.

Figure 19A:
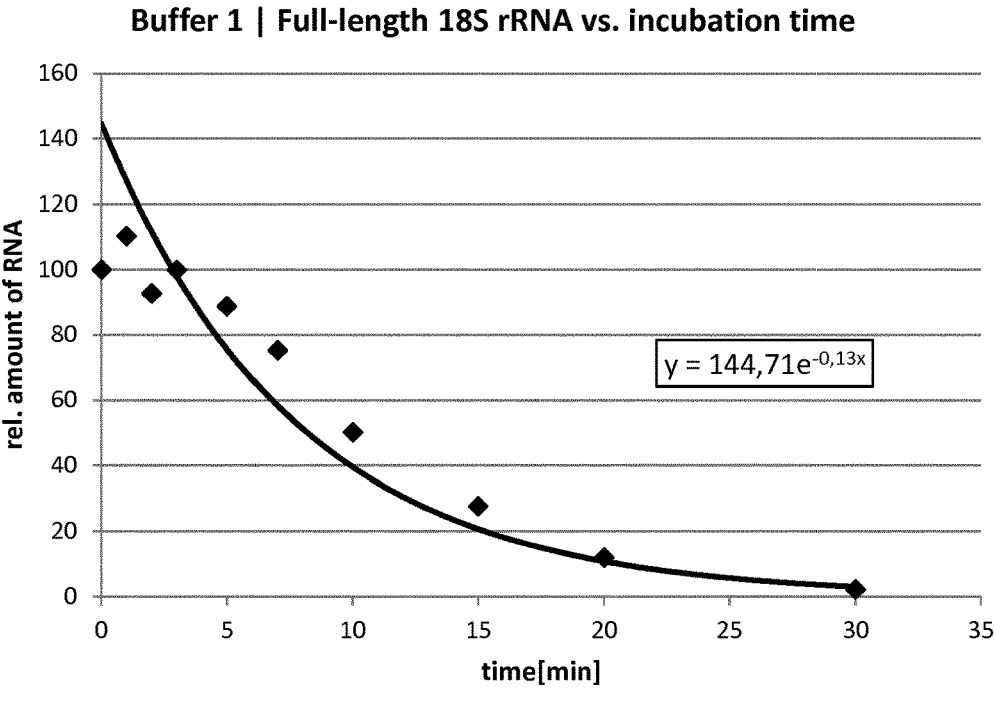
FIGS. 19A to 19C show the relative amount of 18S rRNA vs. incubation time for Buffers 1 to 3 tested in Example 5, respectively. The y-axis indicates the relative amount of full-length 18S rRNA (%); the x-axis indicates the incubation time.
Figure 19B:
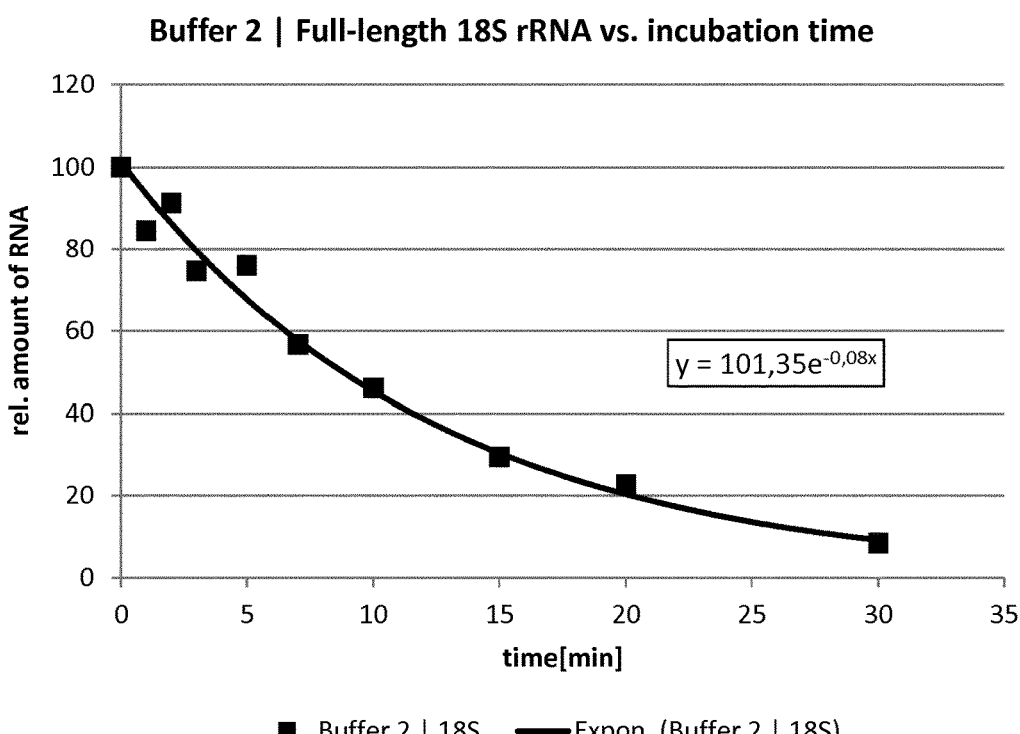
Figure 19C:
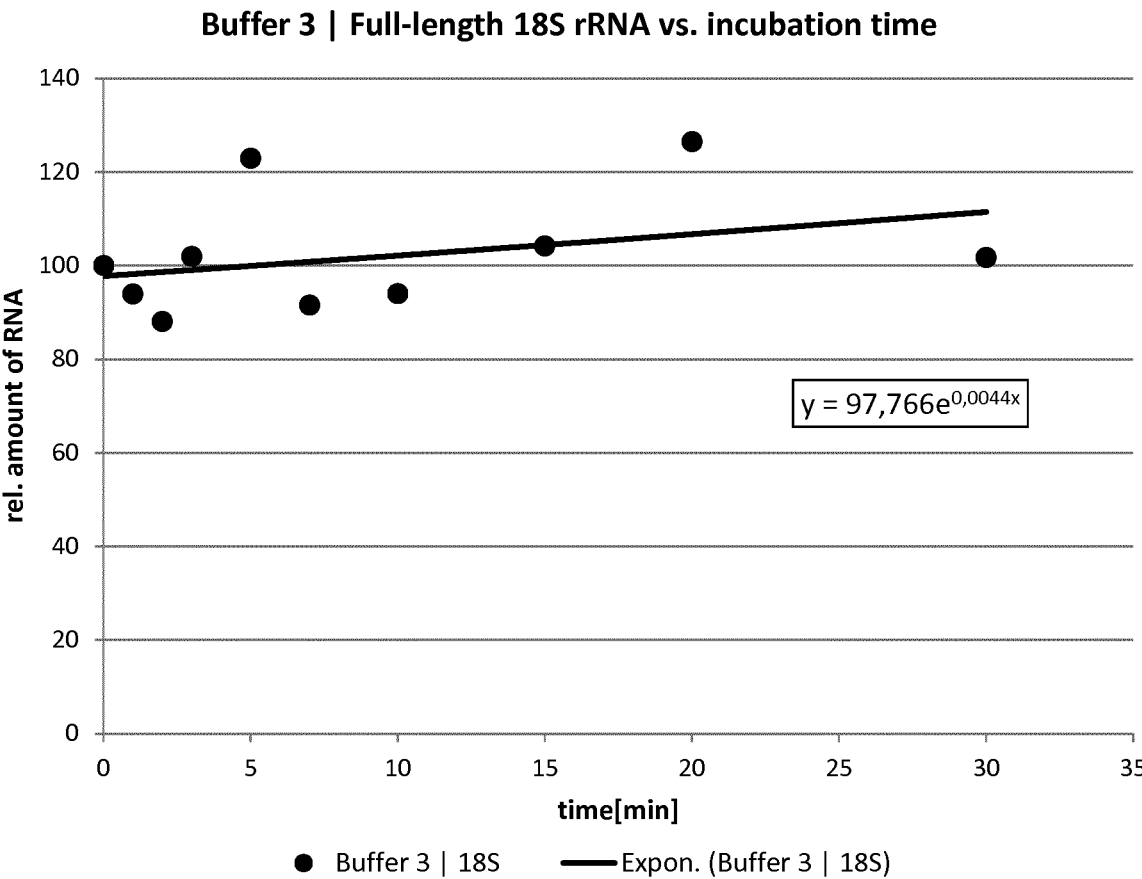

The data obtained and shown in Table 17 was analyzed by fitting a first-order decay curve (amount of rRNA vs. incubation time) and determining the half-lives of the full-length rRNA. The resulting curves for Buffers 1 to 3 are shown in FIGS. 19A to 19C, respectively. For each Figure, the y-axis indicates the relative amount of full-length 18S rRNA (%); the x-axis indicates the incubation time.

The 28S rRNA detected based on band intensity (% of 28S rRNA at time point 0) in the different buffers is shown in Table 18:

TABLE 18

| Sample [min] | Buffer 1 \| 28S | Buffer 2 \| 28S | Buffer 3 \| 28S |
|---|---|---|---|
| 0 | 100 | 100 | 100 |
| 1 | 107 | 83 | 90 |
| 2 | 87 | 84 | 78 |
| 3 | 101 | 64 | 95 |
| 5 | 59 | 51 | 103 |
| 7 | 36 | 29 | 75 |
| 10 | 11 | 14 | 71 |
| 15 | 0 | 1 | 70 |
| 20 | 0 | 1 | 74 |
| 30 | 1 | 3 | 32 |

Figure 20A:
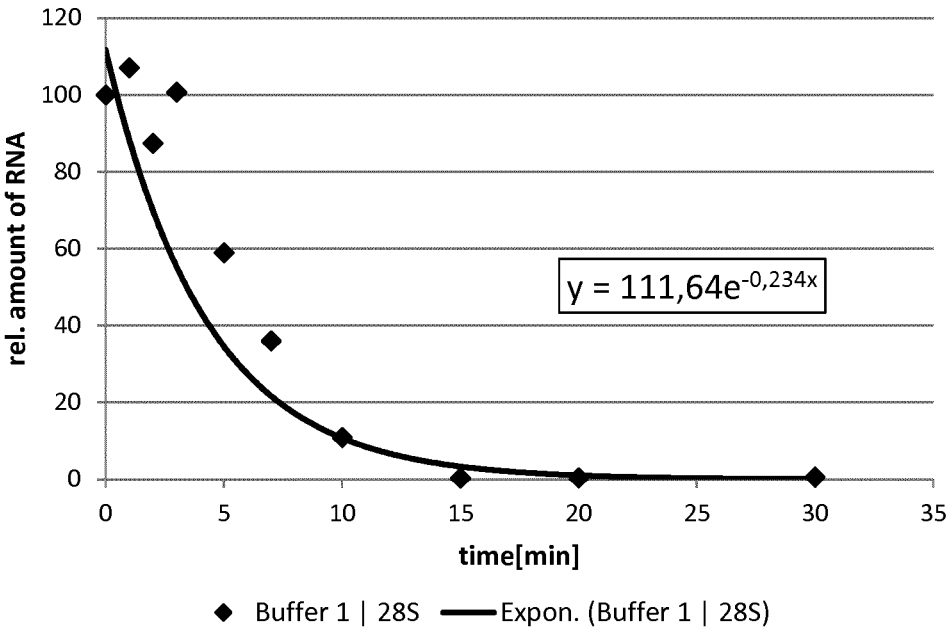
FIGS. 20A to 20C show the relative amount of 28S rRNA vs. incubation time for Buffers 1 to 3 tested in Example 5, respectively. The y-axis indicates the relative amount of full-length 28S rRNA (%); the x-axis indicates the incubation time.
Figure 20B:
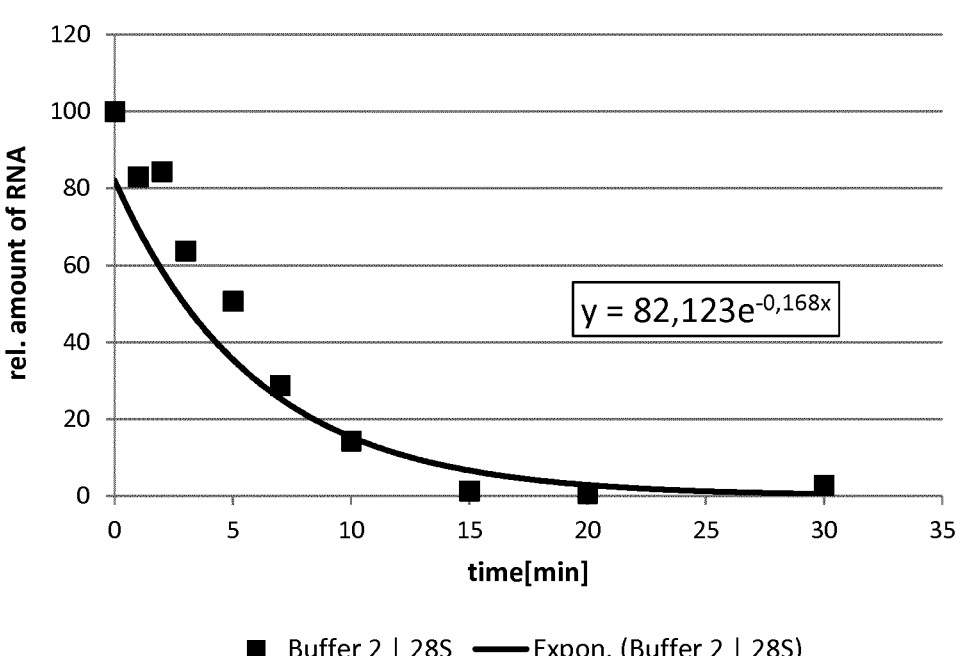
Figure 20C:
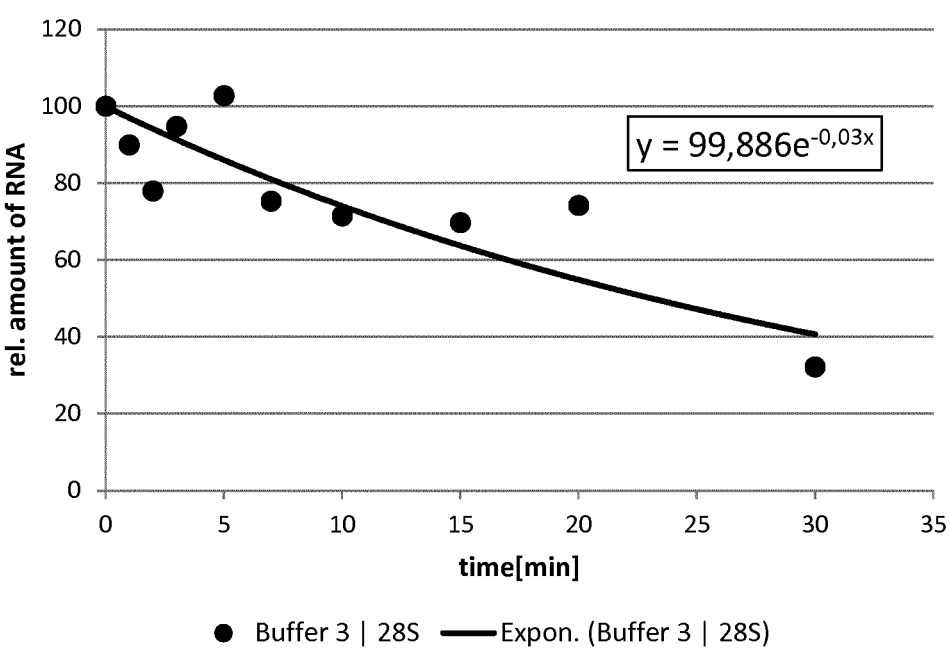

The data obtained and shown in Table 18 was analyzed by fitting a first-order decay curve (amount of rRNA vs. incubation time) and determining the half-lives of the full-length rRNA. The resulting curves for Buffers 1 to 3 are shown in FIGS. 20A to 20C, respectively. For each Figure, the y-axis indicates the relative amount of full-length 28S rRNA (%); the x-axis indicates the incubation time.

RNA Half-Lives were Calculated as Follows:

Assumption: The full-length RNA degrades according to a first-order kinetics, hence the measured relative amount of RNA vs. time can be expressed as:

$$y = x_0 \cdot e^{-k \cdot t}$$

with y=amount of RNA at time x $x_0$=amount of RNA at time point 0 (here set to 100%—see above)

k=kinetic constant t=time [min]

The half-life t($\frac{1}{2}$) can be calculated from the kinetic constant k: t($\frac{1}{2}$)=ln(2)/k. Results are shown in Table 19:

TABLE 19

| Buffer | rRNA half-life [min] \| 18S | Fold increase in half-life (18S)* | rRNA half-life [min] \| 28S | Fold increase in half-life (28S)* |
|---|---|---|---|---|
| 1 | 5.3 | — | 3.0 | — |
| 2 | 8.7 | 1.6 | 4.1 | 1.4 |
| 3 | no degradation | n/a | 23.1 | 7.7 |

*compared to buffer 1 (=unstabilized RNA)

Conclusions for Example 5:

18S rRNA and 28S rRNA degrade rapidly when incubated at 75° C. and pH 10, although not as rapidly as with a pH 11 and a temperature of 85° C. (Example 4).

Addition of 2.5 mM ammonium sulfate in the presence of pH 10 and 75° C. has a stabilizing effect on the full-length rRNAs; the increase in half life is modest, both for 18S rRNA and 28S rRNA. After incubation for 20 minutes or longer, the effect becomes more pronounced.

Addition of 2.5 mM ammonium sulfate and 1 mM EDTA in the presence of presence of pH 10 and 75° C. leads to a strong stabilizing effect for both 18S and 28S rRNAs: No measureable degradation is detected for 18S rRNA over a 30 min incubation period; for the 28S rRNA, the half-life of the full-length RNA increases more than 7-fold compared to the unstabilized RNA.

---

The invention claimed is:

1. A method of reducing, protecting from, inhibiting and/or preventing degradation of RNA, comprising treating the RNA at conditions comprising a temperature of at least 70° C. and a pH of at least 8 in the presence of ammonium sulfate, wherein ammonium sulfate is at a concentration of less than 10 mM, the RNA is bound to an anion exchange matrix, and the RNA is released from the anion exchange matrix during the treatment, thereby reducing, protecting from, inhibiting and/or preventing degradation of the RNA.

2. The method according to claim 1, wherein the pH is at least 9.

3. The method according to claim 1, having one or more of the following characteristics:

(i) the ammonium sulfate is present at a concentration of from 0.25 mM to 9 mM, from 0.5 mM to 9 mM, from 0.7 mM to 8 mM, from 1 mM to 7 mM, from 1.5 mM to 6 mM, from 1.75 mM to 5 mM or from 2 mM to 4 mM; or about 2.5 mM;

(ii) the ammonium sulfate is diammonium sulfate $((NH_4)_2SO_4))$;

(iii) the pH is in a range from 9 to 14, from 9.2 to 13.5, from 9.4 to 13, from 9.6 to 12.5, from 9.8 to 12.25, from 10 to 12, or from 10 to 11.5;

(iv) the temperature is in a range from 70° C. to 100° C., from 70° C. to 95° C., from 75° C. to 90° C., or from about 75° C. to 85° C.; and (v) the step of treating occurs in the presence of a chelating agent.

4. The method of claim 3, wherein the step of treating occurs in the presence of a chelating agent, and wherein the chelating agent is EDTA.

5. The method of claim 4, wherein the solution comprises EDTA at a concentration of 5 mM or less.

6. The method according to claim 1, having one or more of the following characteristics:

(i) the RNA is incubated for 1 min to 20 min, 2 min to 15 min, 5 min to 12 min, or 7 min to 10 min; and (ii) incubation occurs in the presence of one or more proteolytic enzymes or other enzymatic compounds and wherein the one or more proteolytic enzymes or other enzymatic compounds are inactivated during incubation.

7. The method according to claim 1, wherein the ammonium sulfate is comprised in a solution that is contacted with the RNA.

8. The method according to claim 7, wherein the solution has one or more of the following characteristics:

(i) the solution comprises ammonium sulfate at a concentration of 0.25 mM to 9 mM, from 0.5 mM to 9 mM, from 0.7 mM to 8 mM, from 1 mM to 7 mM, from 1.5 mM to 6 mM, from 1.75 mM to 5 mM or from 2 mM to 4 mM; or about 2.5 mM;

(ii) the solution has a pH of at least 9;

(iii) the solution has a pH in a range from 9 to 14, from 9.2 to 13.5, from 9.4 to 13, from 9.6 to 12.5, from 9.8 to 12.25, from 10 to 12 or 10.5 to 11.5;

(iv) the solution is aqueous;

(v) the solution comprises one or more alkali hydroxide salts, (vi) the solution comprises sodium hydroxide and/or potassium hydroxide;

(vii) the solution has an ionic strength of <100 mM;

(viii) the solution is buffered;

(ix) the solution comprises a chelating agent;

(x) the solution does not comprise non-complexed bi-valent cations, or does not comprise bi-valent cations at all;

(xi) the solution has a temperature of at least 70° C., at least 75° C., at least 80° C. or at least 85° C.; and (xii) the solution has a pH of at least 9 and wherein after contacting the RNA with the solution it is heated to a temperature of at least 70° C.

9. The method according to claim 1, wherein the method isolates RNA from a sample, said method comprising:

binding the RNA from the sample to an anion exchange matrix prior to the step of treating;

wherein the step of treating releases the RNA from the anion exchange matrix.

10. The method according to claim 1, wherein the treatment conditions for releasing the RNA from the anion exchange matrix are as defined in one or more of the following:

a) the ammonium sulfate is present at a concentration of 0.25 mM to 9 mM, from 0.5 mM to 9 mM, from 0.7 mM to 8 mM, from 1 mM to 7 mM, from 1.5 mM to 6 mM, from 1.75 mM to 5 mM or from 2 mM to 4 mM; or about 2.5 mM;

b) the ammonium sulfate is diammonium sulfate ($(NH_4)_2SO_4$));

c) the pH is in a range from 9 to 14, from 9.2 to 13.5, from 9.4 to 13, from 9.6 to 12.5, from 9.8 to 12.25, from 10 to 12 or from 10 to 11.5;

d) the temperature is in a range from 70° C. to 100° C., from 70° C. to 95° C., from 75° C. to 90° C. or from about 75° C. to 85° C.;

e) the step of treating occurs in the presence of a chelating agent;

f) the step of treating comprises incubating the RNA at the conditions, wherein the RNA is incubated for 1 min to 20 min, 2 min to 15 min, 5 min to 12 min, or 7 min to 10 min; and g) the step of treating comprises incubating the RNA at the conditions, wherein the incubating occurs in the presence of one or more proteolytic enzymes or other enzymatic compounds, and wherein the one or more proteolytic enzymes or other enzymatic compounds are inactivated during incubation.

11. The method of claim 10, wherein the step of treating occurs in the presence of a chelating agent, and wherein the chelating agent is EDTA.

12. The method according to claim 1, wherein the RNA is contacted with a solution that comprises ammonium sulfate to release the RNA from the anion exchange matrix.

13. The method of claim 12, wherein the solution has one or more of the following characteristics:

(i) the solution comprises ammonium sulfate at a concentration of 0.25 mM to 9 mM, from 0.5 mM to 9 mM, from 0.7 mM to 8 mM, from 1 mM to 7 mM, from 1.5 mM to 6 mM, from 1.75 mM to 5 mM or from 2 mM to 4 mM; or about 2.5 mM;

(ii) the solution has a pH of at least 9;

(iii) the solution has a pH in a range from 9 to 14, from 9.2 to 13.5, from 9.4 to 13, from 9.6 to 12.5, from 9.8 to 12.25, from 10 to 12 or 10.5 to 11.5;

(iv) the solution is aqueous;

(v) the solution comprises one or more alkali hydroxide salts, (vi) the solution comprises sodium hydroxide and/or potassium hydroxide;

(vii) the solution has an ionic strength of <100 mM;

(viii) the solution is buffered;

(ix) the solution comprises a chelating agent;

(x) the solution does not comprise non-complexed bi-valent cations, or does not comprise bi-valent cations at all;

(xi) the solution has a temperature of at least 70° C., at least 75° C., at least 80° C. or at least 85° C.; and (xii) the solution has a pH of at least 9 and wherein after contacting the RNA with the solution it is heated to a temperature of at least 70° C.

14. The method according to claim 1, wherein the anion exchange matrix has one or more of the following characteristics:

(i) it comprises anion exchange moieties that provide anion exchange groups, wherein the anion exchange moieties are selected from monoamines, diamines, polyamines, nitrogen-containing aromatic or aliphatic heterocyclic groups, cyclic amines, aromatic amines and heterocyclic amines;

(ii) it comprises anion exchange moieties that comprise at least one primary, secondary and/or tertiary amino group;

(iii) it is provided by a solid support that provides an anion exchange surface; and (iv) it is provided by magnetic particles.

15. The method of claim 1, wherein the pHis at least 9.

16. The method of claim 1, wherein the solution comprises ammonium sulfate at a concentration of 7 mM or less.

17. The method of claim 1, wherein the solution comprises ammonium sulfate at a concentration of 5 mM or less.

18. The method of claim 1, wherein the temperature is in a range from about 75° C. to 85° C.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: artificial sequence
<220> FEATURE:
<223> OTHER INFORMATION: human ribosomal DNA forward primer

<400> SEQUENCE: 1
gccgctagag gtgaaattct tg                                            22

<210> SEQ ID NO 2
<211> LENGTH: 21
<212> TYPE: DNA
<213> ORGANISM: artificial sequence
<220> FEATURE:
<223> OTHER INFORMATION: human ribosomal DNA reverse primer

<400> SEQUENCE: 2
cattcttggc aaatgctttc g                                             21

<210> SEQ ID NO 3
<211> LENGTH: 21
<212> TYPE: DNA
<213> ORGANISM: artificial sequence
<220> FEATURE:
<223> OTHER INFORMATION: human ribosomal DNA probe

<400> SEQUENCE: 3
accggcgcaa gacggaccag a                                             21

<210> SEQ ID NO 4
```

-continued

```
<211> LENGTH: 22
<212> TYPE: DNA
<213> ORGANISM: artificial sequence
<220> FEATURE:
<223> OTHER INFORMATION: human ribosomal DNA forward primer

<400> SEQUENCE: 4
gtcgctcgct cctctcctac tt                                            22

<210> SEQ ID NO 5
<211> LENGTH: 19
<212> TYPE: DNA
<213> ORGANISM: artificial sequence
<220> FEATURE:
<223> OTHER INFORMATION: human ribosomal DNA reverse primer

<400> SEQUENCE: 5
ggctgctggc accagactt                                               19

<210> SEQ ID NO 6
<211> LENGTH: 25
<212> TYPE: DNA
<213> ORGANISM: artificial sequence
<220> FEATURE:
<223> OTHER INFORMATION: human ribosomal DNA probe

<400> SEQUENCE: 6
ctaatacatg ccgacgggcg ctgac                                        25
```